US012295550B2

(12) United States Patent
Tilson et al.

(10) Patent No.: US 12,295,550 B2
(45) Date of Patent: May 13, 2025

(54) DYNAMICALLY RIGIDIZING OVERTUBE

(71) Applicant: NEPTUNE MEDICAL INC., Burlingame, CA (US)

(72) Inventors: Alexander Q. Tilson, Burlingame, CA (US); Garrett J. Gomes, San Mateo, CA (US); Stephen J. Morris, Sunnyvale, CA (US); Eugene F. Duval, Menlo Park, CA (US); Adam S. Wigginton, Sunnyvale, CA (US); Mark C. Scheeff, San Francisco, CA (US)

(73) Assignee: Neptune Medical Inc., Burlingame, CA (US)

( * ) Notice: Subject to any disclaimer, the term of this patent is extended or adjusted under 35 U.S.C. 154(b) by 198 days.

(21) Appl. No.: 16/631,473

(22) PCT Filed: Jul. 19, 2018

(86) PCT No.: PCT/US2018/042946
§ 371 (c)(1),
(2) Date: Jan. 16, 2020

(87) PCT Pub. No.: WO2019/018682
PCT Pub. Date: Jan. 24, 2019

(65) Prior Publication Data
US 2020/0178763 A1    Jun. 11, 2020

Related U.S. Application Data

(60) Provisional application No. 62/672,444, filed on May 16, 2018, provisional application No. 62/535,134, filed on Jul. 20, 2017.

(51) Int. Cl.
*A61B 1/00*        (2006.01)
*A61B 1/005*       (2006.01)
(Continued)

(52) U.S. Cl.
CPC ...... *A61B 1/00078* (2013.01); *A61B 1/00135* (2013.01); *A61B 1/0052* (2013.01);
(Continued)

(58) Field of Classification Search
CPC ............ A61B 1/00078; A61B 1/00135; A61B 1/0052; A61B 1/0055; A61B 1/0057; A61B 1/008; A61B 2034/301; A61M 25/0155
See application file for complete search history.

(56) References Cited

U.S. PATENT DOCUMENTS 2,268,321 A    12/1941   Flynn
2,767,705 A    10/1956   Moore
(Continued)

FOREIGN PATENT DOCUMENTS

AU    2013207571 B1    8/2013
CN       2613655 Y     4/2004
(Continued)

OTHER PUBLICATIONS

Entrada Colonic Overtube Product Brochure (Year: 2009).*
(Continued)

*Primary Examiner* — Anh Tuan T Nguyen
*Assistant Examiner* — Megan Elizabeth Monahan
(74) *Attorney, Agent, or Firm* — Shay Glenn LLP

(57) ABSTRACT

A rigidizing overtube includes an elongate flexible tube, one or more mounting elements attached to the flexible tube, and a plurality of engagers connected to the one or more mounting elements. The rigidizing overtube has a flexible configuration in which the plurality of engagers are configured to move relative to other engagers to accommodate bending of the flexible tube. The rigidizing overtube also has a rigid
(Continued)

configuration in which the plurality of engagers are fixed relative to other engagers to prevent the flexible tube from bending.

20 Claims, 72 Drawing Sheets

(51) Int. Cl.
*A61B 1/008* (2006.01)
*A61B 17/00* (2006.01)
*A61B 34/30* (2016.01)
*A61M 25/01* (2006.01)

(52) U.S. Cl.
CPC .......... *A61B 1/0055* (2013.01); *A61B 1/0057* (2013.01); *A61B 1/008* (2013.01); *A61B 2017/00318* (2013.01); *A61B 2034/301* (2016.02); *A61M 25/0155* (2013.01)

(56) References Cited

U.S. PATENT DOCUMENTS

| | | |
|---|---|---|
| 3,859,986 A | 1/1975 | Okada et al. |
| 3,998,216 A | 12/1976 | Hosono |
| 4,066,071 A | 1/1978 | Nagel |
| 4,141,364 A | 2/1979 | Schultze |
| 4,151,800 A | 5/1979 | Dotts et al. |
| 4,176,662 A | 12/1979 | Frazer |
| 4,425,919 A | 1/1984 | Alston, Jr. |
| 4,551,140 A | 11/1985 | Shinohara |
| 4,690,131 A | 9/1987 | Lyddy, Jr. et al. |
| 4,696,544 A | 9/1987 | Costella |
| 4,717,379 A | 1/1988 | Ekholmer |
| 4,794,412 A | 12/1988 | Casey et al. |
| 4,794,912 A | 1/1989 | Lia |
| 4,815,450 A | 3/1989 | Patel |
| 4,817,613 A | 4/1989 | Jaraczewski et al. |
| 4,890,602 A | 1/1990 | Hake |
| 4,893,613 A | 1/1990 | Hake |
| 4,913,369 A | 4/1990 | Lia et al. |
| 4,959,058 A | 9/1990 | Michelson |
| 4,961,738 A | 10/1990 | Mackin |
| 5,018,436 A | 5/1991 | Evangelista et al. |
| 5,019,121 A | 5/1991 | Krauter |
| 5,037,386 A | 8/1991 | Marcus et al. |
| 5,037,404 A | 8/1991 | Gold et al. |
| 5,105,819 A | 4/1992 | Wollschlager et al. |
| 5,123,421 A | 6/1992 | Sinofsky |
| 5,125,143 A | 6/1992 | Takahashi |
| 5,174,276 A | 12/1992 | Crockard |
| 5,188,595 A | 2/1993 | Jacobi |
| 5,193,525 A | 3/1993 | Silverstein et al. |
| 5,201,908 A | 4/1993 | Jones |
| 5,251,611 A | 10/1993 | Zehel et al. |
| 5,337,733 A | 8/1994 | Bauerfeind et al. |
| 5,360,440 A | 11/1994 | Andersen |
| 5,447,148 A | 9/1995 | Oneda et al. |
| 5,496,292 A | 3/1996 | Burnham |
| 5,531,685 A | 7/1996 | Hemmer et al. |
| 5,531,719 A | 7/1996 | Takahashi |
| 5,577,992 A | 11/1996 | Chiba et al. |
| 5,601,588 A | 2/1997 | Tonomura et al. |
| 5,603,991 A | 2/1997 | Kupiecki et al. |
| 5,607,435 A | 3/1997 | Sachdeva et al. |
| 5,624,381 A | 4/1997 | Kieturakis |
| 5,632,734 A | 5/1997 | Galel et al. |
| 5,662,587 A | 9/1997 | Grundfest et al. |
| 5,662,621 A | 9/1997 | Lafontaine |
| 5,746,692 A | 5/1998 | Bacich et al. |
| 5,749,828 A | 5/1998 | Solomon et al. |
| 5,759,151 A | 6/1998 | Sturges |
| 5,779,624 A | 7/1998 | Chang |
| 5,782,811 A | 7/1998 | Samson et al. |
| 5,823,961 A | 10/1998 | Fields et al. |
| 5,882,347 A | 3/1999 | Mouris Laan et al. |
| 5,891,112 A | 4/1999 | Samson |
| 5,891,114 A | 4/1999 | Chin et al. |
| 5,906,591 A | 5/1999 | Dario et al. |
| 5,916,145 A | 6/1999 | Chu et al. |
| 5,916,147 A | 6/1999 | Boury |
| 5,951,539 A | 9/1999 | Nita et al. |
| 5,976,074 A | 11/1999 | Moriyama |
| 6,090,099 A | 7/2000 | Samson et al. |
| 6,159,187 A | 12/2000 | Park et al. |
| 6,162,171 A | 12/2000 | Ng et al. |
| 6,165,123 A | 12/2000 | Thompson |
| 6,179,776 B1 | 1/2001 | Adams et al. |
| 6,190,357 B1 | 2/2001 | Ferrari et al. |
| 6,217,565 B1 | 4/2001 | Cohen |
| 6,296,644 B1 | 10/2001 | Surat et al. |
| 6,309,346 B1 | 10/2001 | Farhadi |
| 6,352,503 B1 | 3/2002 | Matsu et al. |
| 6,364,878 B1 | 4/2002 | Hall |
| 6,368,315 B1 | 4/2002 | Gillis et al. |
| 6,468,203 B2 | 10/2002 | Belson |
| 6,485,409 B1 | 11/2002 | Voloshin et al. |
| 6,503,225 B1 | 1/2003 | Kirsch et al. |
| 6,517,477 B1 | 2/2003 | Wendlandt |
| 6,547,724 B1 | 4/2003 | Soble et al. |
| 6,572,538 B2 | 6/2003 | Takase |
| 6,572,590 B1 | 6/2003 | Stevens et al. |
| 6,579,277 B1 | 6/2003 | Rabiner et al. |
| 6,610,007 B2 | 8/2003 | Beison et al. |
| 6,612,982 B1 | 9/2003 | Ouchi |
| 6,616,628 B2 | 9/2003 | Hayzelden |
| 6,620,126 B2 | 9/2003 | Unsworth et al. |
| 6,623,424 B2 | 9/2003 | Hayakawa et al. |
| 6,712,832 B2 | 3/2004 | Shah |
| 6,726,677 B1 | 4/2004 | Flaherty et al. |
| 6,730,020 B2 | 5/2004 | Peng et al. |
| 6,780,151 B2 | 8/2004 | Grabover et al. |
| 6,783,491 B2 | 8/2004 | Saadat et al. |
| 6,790,173 B2 | 9/2004 | Saadat et al. |
| 6,793,621 B2 | 9/2004 | Butler et al. |
| 6,793,661 B2 | 9/2004 | Hamilton et al. |
| 6,800,056 B2 | 10/2004 | Tartaglia et al. |
| 6,869,393 B2 | 3/2005 | Butler |
| 6,899,673 B2 | 5/2005 | Ogura et al. |
| 6,911,004 B2 | 6/2005 | Kim et al. |
| 6,923,754 B2 | 8/2005 | Lubock |
| 6,960,162 B2 | 11/2005 | Saadat et al. |
| 6,974,411 B2 | 12/2005 | Belson |
| 6,984,203 B2 | 1/2006 | Tartaglia et al. |
| 7,060,199 B2 | 6/2006 | Woydt et al. |
| 7,172,552 B2 | 2/2007 | Wendlandt |
| 7,214,230 B2 | 5/2007 | Brock et al. |
| 7,288,101 B2 | 10/2007 | Deem et al. |
| 7,291,127 B2 | 11/2007 | Eidenschink |
| 7,365,509 B2 | 4/2008 | Park et al. |
| 7,438,712 B2 | 10/2008 | Chouinard |
| 7,511,733 B2 | 3/2009 | Takizawa et al. |
| 7,537,562 B2 | 5/2009 | Takano |
| 7,559,916 B2 | 7/2009 | Smith et al. |
| 7,591,782 B2 | 9/2009 | Fujikura |
| 7,598,652 B2 | 10/2009 | Kornbluh et al. |
| 7,695,428 B2 | 4/2010 | Machida |
| 7,736,323 B2 | 6/2010 | Von Weymarn-Scharli |
| 7,749,196 B2 | 7/2010 | Osborne et al. |
| 7,837,615 B2 | 11/2010 | Le et al. |
| 7,850,725 B2 | 12/2010 | Vardi et al. |
| 7,901,347 B2 | 3/2011 | Sekiguchi et al. |
| 7,909,755 B2 | 3/2011 | Itoi |
| 7,918,819 B2 | 4/2011 | Karmarkar et al. |
| 7,918,845 B2 | 4/2011 | Saadat et al. |
| 7,931,661 B2 | 4/2011 | Saadat et al. |
| 7,935,047 B2 | 5/2011 | Yoshida et al. |
| 7,947,000 B2 | 5/2011 | Vargas et al. |
| 7,957,790 B2 | 6/2011 | Kleen |
| 7,970,455 B2 | 6/2011 | Zilberstein et al. |
| 7,988,621 B2 | 8/2011 | Smith et al. |
| 8,047,236 B2 | 11/2011 | Perry |
| 8,075,476 B2 | 12/2011 | Vargas |
| 8,092,374 B2 | 1/2012 | Smith et al. |

(56) References Cited

U.S. PATENT DOCUMENTS

| | | |
|---|---|---|
| 8,109,953 B1 | 2/2012 | King, III et al. |
| 8,123,739 B2 | 2/2012 | McQueen et al. |
| 8,125,755 B2 | 2/2012 | Garcia et al. |
| 8,192,422 B2 | 6/2012 | Zubiate et al. |
| 8,206,287 B2 | 6/2012 | Matsuo |
| 8,226,548 B2 | 7/2012 | Kucklick |
| 8,241,299 B2 | 8/2012 | Hibner |
| 8,246,575 B2 | 8/2012 | Viola |
| 8,257,257 B2 | 9/2012 | Takizawa et al. |
| 8,262,677 B2 | 9/2012 | Goto |
| 8,298,161 B2 * | 10/2012 | Vargas ............ A61B 17/00234 600/587 |
| 8,313,014 B2 | 11/2012 | Bettuchi |
| 8,361,090 B2 | 1/2013 | Belson |
| 8,366,606 B2 | 2/2013 | Watanabe et al. |
| 8,388,519 B2 | 3/2013 | Garcia et al. |
| 8,439,825 B2 | 5/2013 | Sekiguchi |
| 8,460,179 B2 | 6/2013 | Ikeda et al. |
| 8,485,968 B2 | 7/2013 | Weimer et al. |
| 8,496,648 B2 | 7/2013 | Rogers |
| 8,506,479 B2 | 8/2013 | Piskun et al. |
| 8,517,923 B2 | 8/2013 | Belson et al. |
| 8,545,491 B2 | 10/2013 | Abboud et al. |
| 8,550,989 B2 | 10/2013 | Dohl et al. |
| 8,556,804 B2 | 10/2013 | Smith et al. |
| 8,663,096 B2 | 3/2014 | Viola |
| 8,663,196 B2 | 3/2014 | Kassab et al. |
| 8,708,894 B2 | 4/2014 | Smith |
| 8,721,530 B2 | 5/2014 | Ohline et al. |
| 8,753,312 B2 | 6/2014 | Bowe et al. |
| 8,777,844 B1 | 7/2014 | Sadanand |
| 8,920,369 B2 | 12/2014 | Salahieh et al. |
| 8,969,639 B2 | 3/2015 | Xu et al. |
| 9,011,318 B2 | 4/2015 | Choset et al. |
| 9,066,655 B2 | 6/2015 | Stefanchik et al. |
| 9,114,228 B2 | 8/2015 | Zook et al. |
| 9,125,653 B2 | 9/2015 | Kovach |
| 9,155,451 B2 | 10/2015 | Smith et al. |
| 9,192,284 B2 | 11/2015 | Hirsch et al. |
| 9,192,288 B2 | 11/2015 | Okaniwa |
| 9,211,140 B2 | 12/2015 | Lauryssen et al. |
| 9,220,398 B2 | 12/2015 | Woodley et al. |
| 9,226,825 B2 | 1/2016 | Starksen et al. |
| 9,241,611 B2 | 1/2016 | Konno |
| 9,254,123 B2 | 2/2016 | Alvarez et al. |
| 9,295,511 B2 | 3/2016 | Smith et al. |
| 9,333,287 B2 | 5/2016 | Nitsan et al. |
| 9,358,073 B2 | 6/2016 | Piligian et al. |
| 9,364,955 B2 | 6/2016 | Oyola et al. |
| 9,386,910 B2 | 7/2016 | West |
| 9,498,108 B1 | 11/2016 | Lombardi |
| 9,498,198 B2 | 11/2016 | Hu et al. |
| 9,505,125 B2 | 11/2016 | Zubiate et al. |
| 9,585,546 B2 | 3/2017 | Surti et al. |
| 9,610,068 B2 | 4/2017 | Kappel et al. |
| 9,649,473 B2 | 5/2017 | Gregorich et al. |
| 9,763,562 B2 | 9/2017 | Avitsian et al. |
| 9,814,372 B2 | 11/2017 | Smith et al. |
| 9,913,570 B2 | 3/2018 | Kucharski et al. |
| 9,937,324 B2 | 4/2018 | Kim et al. |
| 9,993,142 B2 | 6/2018 | Salman et al. |
| 10,092,291 B2 | 10/2018 | Voegele et al. |
| 10,307,042 B2 | 6/2019 | Lombardi |
| 10,463,495 B2 | 11/2019 | Rogers et al. |
| 11,006,975 B1 | 5/2021 | Cohen et al. |
| 11,554,248 B1 | 1/2023 | Tilson et al. |
| 2001/0041881 A1 | 11/2001 | Sarge et al. |
| 2002/0107478 A1 | 8/2002 | Wendlandt |
| 2002/0161355 A1 | 10/2002 | Wollschlager |
| 2003/0023259 A1 | 1/2003 | Dubrul et al. |
| 2003/0035048 A1 | 2/2003 | Shipp |
| 2003/0036748 A1 | 2/2003 | Cooper et al. |
| 2003/0083546 A1 | 5/2003 | Butler et al. |
| 2003/0122374 A1 | 7/2003 | Ouchi et al. |
| 2003/0153866 A1 | 8/2003 | Long et al. |
| 2003/0208220 A1 | 11/2003 | Worley et al. |
| 2003/0216691 A1 | 11/2003 | Jacobson |
| 2003/0225379 A1 | 12/2003 | Schaffer et al. |
| 2004/0019252 A1 | 1/2004 | Hirata |
| 2004/0044350 A1 | 3/2004 | Martin et al. |
| 2004/0092960 A1 | 5/2004 | Abrams et al. |
| 2004/0186349 A1 | 9/2004 | Ewers et al. |
| 2004/0186350 A1 | 9/2004 | Brenneman et al. |
| 2004/0242958 A1 | 12/2004 | Fujikawa et al. |
| 2004/0243227 A1 | 12/2004 | Starksen et al. |
| 2004/0260236 A1 | 12/2004 | Manning et al. |
| 2005/0005363 A1 | 1/2005 | Giori et al. |
| 2005/0010237 A1 | 1/2005 | Niazi |
| 2005/0085829 A1 | 4/2005 | Kraemer et al. |
| 2005/0165275 A1 | 7/2005 | Von Felten et al. |
| 2005/0165366 A1 | 7/2005 | Brustad et al. |
| 2005/0203340 A1 | 9/2005 | Butler et al. |
| 2005/0261581 A1 | 11/2005 | Hughes et al. |
| 2005/0272974 A1 | 12/2005 | Iddan |
| 2005/0277966 A1 | 12/2005 | Ewers et al. |
| 2006/0041188 A1 | 2/2006 | Dirusso et al. |
| 2006/0047183 A1 | 3/2006 | Park |
| 2006/0058582 A1 | 3/2006 | Maahs et al. |
| 2006/0063973 A1 | 3/2006 | Makower et al. |
| 2006/0106285 A1 | 5/2006 | Boulais et al. |
| 2006/0129130 A1 | 6/2006 | Tal et al. |
| 2006/0192465 A1 | 8/2006 | Kornbluh et al. |
| 2006/0199999 A1 | 9/2006 | Ikeda et al. |
| 2006/0235458 A1 | 10/2006 | Belson |
| 2006/0258906 A1 | 11/2006 | Binmoeller |
| 2006/0264707 A1 | 11/2006 | Kinney |
| 2006/0264821 A1 | 11/2006 | Vo et al. |
| 2006/0287666 A1 | 12/2006 | Saadat et al. |
| 2007/0015965 A1 | 1/2007 | Cox et al. |
| 2007/0038025 A1 | 2/2007 | Yoshida |
| 2007/0045504 A1 | 3/2007 | Wollschlager |
| 2007/0088367 A1 | 4/2007 | Von Weymarn-Scharli |
| 2007/0100414 A1 | 5/2007 | Licata et al. |
| 2007/0106302 A1 | 5/2007 | Ortiz |
| 2007/0118015 A1 | 5/2007 | Wendlandt |
| 2007/0135803 A1 | 6/2007 | Belson |
| 2007/0156018 A1 | 7/2007 | Krauter et al. |
| 2007/0219411 A1 | 9/2007 | Dejima et al. |
| 2007/0239252 A1 | 10/2007 | Hopkins et al. |
| 2007/0250113 A1 | 10/2007 | Hegeman et al. |
| 2007/0250149 A1 | 10/2007 | Oepen et al. |
| 2007/0255101 A1 | 11/2007 | Bar Or |
| 2007/0260121 A1 | 11/2007 | Bakos et al. |
| 2007/0282358 A1 | 12/2007 | Remiszewski et al. |
| 2008/0051635 A1 | 2/2008 | Tanaka et al. |
| 2008/0058722 A1 | 3/2008 | Oepen et al. |
| 2008/0091073 A1 | 4/2008 | Park |
| 2008/0103440 A1 | 5/2008 | Ferren et al. |
| 2008/0139887 A1 | 6/2008 | Fitzpatrick |
| 2008/0172037 A1 | 7/2008 | Huang et al. |
| 2008/0188928 A1 | 8/2008 | Salahieh et al. |
| 2008/0200762 A1 | 8/2008 | Stokes et al. |
| 2008/0214893 A1 | 9/2008 | Tartaglia et al. |
| 2008/0234546 A1 | 9/2008 | Kawano et al. |
| 2008/0242928 A1 | 10/2008 | Kawano et al. |
| 2008/0249362 A1 | 10/2008 | Jiang et al. |
| 2008/0262300 A1 | 10/2008 | Ewers et al. |
| 2008/0275299 A1 | 11/2008 | Park |
| 2009/0023983 A1 | 1/2009 | Stefanchik |
| 2009/0048483 A1 | 2/2009 | Yamamoto |
| 2009/0062611 A1 | 3/2009 | Toyama |
| 2009/0062837 A1 | 3/2009 | Gasche et al. |
| 2009/0062872 A1 | 3/2009 | Chin et al. |
| 2009/0112063 A1 | 4/2009 | Bakos et al. |
| 2009/0131752 A1 | 5/2009 | Park |
| 2009/0157068 A1 | 6/2009 | Kallel et al. |
| 2009/0187163 A1 | 7/2009 | Uihlein |
| 2009/0240202 A1 | 9/2009 | Drasier et al. |
| 2009/0248041 A1 | 10/2009 | Williams et al. |
| 2009/0259200 A1 | 10/2009 | Lampropoulos et al. |
| 2009/0264704 A1 | 10/2009 | Shtul |
| 2010/0010308 A1 | 1/2010 | Braun et al. |
| 2010/0010437 A1 | 1/2010 | Miles et al. |
| 2010/0010504 A1 | 1/2010 | Simaan et al. |

(56) References Cited

U.S. PATENT DOCUMENTS

| | | |
|---|---|---|
| 2010/0016663 A1 | 1/2010 | Maisch et al. |
| 2010/0036363 A1 | 2/2010 | Watanabe et al. |
| 2010/0069712 A1 | 3/2010 | Yamaya |
| 2010/0069716 A1 | 3/2010 | Chin et al. |
| 2010/0076451 A1* | 3/2010 | Zwolinski .............. A61B 1/005 606/1 |
| 2010/0087711 A1 | 4/2010 | Edwards |
| 2010/0137686 A1 | 6/2010 | Meron et al. |
| 2010/0145151 A1 | 6/2010 | Fukunaga et al. |
| 2010/0160735 A1 | 6/2010 | Bakos |
| 2010/0185172 A1 | 7/2010 | Fabro |
| 2010/0204546 A1 | 8/2010 | Hassidov et al. |
| 2010/0268025 A1 | 10/2010 | Belson |
| 2010/0331625 A1 | 12/2010 | Rosemurgy et al. |
| 2010/0331820 A1 | 12/2010 | Prisco et al. |
| 2011/0015729 A1 | 1/2011 | Jimenez et al. |
| 2011/0023888 A1 | 2/2011 | Vazales et al. |
| 2011/0040282 A1 | 2/2011 | Uihlein |
| 2011/0046442 A1 | 2/2011 | Matsushita |
| 2011/0049282 A1 | 3/2011 | Danielsson |
| 2011/0054253 A1 | 3/2011 | Jordá Albiñana et al. |
| 2011/0087070 A1 | 4/2011 | Tilson et al. |
| 2011/0237888 A1 | 9/2011 | Matsushita |
| 2011/0245611 A1 | 10/2011 | Yeh et al. |
| 2011/0282149 A1 | 11/2011 | Vargas et al. |
| 2011/0288553 A1 | 11/2011 | Jansen et al. |
| 2011/0301414 A1 | 12/2011 | Hotto et al. |
| 2011/0306950 A1 | 12/2011 | Cucin |
| 2011/0319714 A1 | 12/2011 | Roelle et al. |
| 2012/0004676 A1 | 1/2012 | Vargas |
| 2012/0022329 A1 | 1/2012 | Wagh et al. |
| 2012/0041291 A1 | 2/2012 | Ferren et al. |
| 2012/0095548 A1 | 4/2012 | Gregorich et al. |
| 2012/0108902 A1 | 5/2012 | Frassica et al. |
| 2012/0130173 A1 | 5/2012 | Lutze et al. |
| 2012/0143005 A1 | 6/2012 | Yeh et al. |
| 2012/0165607 A1 | 6/2012 | Ashida et al. |
| 2012/0165792 A1 | 6/2012 | Ortiz et al. |
| 2012/0172651 A1 | 7/2012 | Cutrer |
| 2012/0209062 A1 | 8/2012 | Qiao |
| 2012/0277528 A1 | 11/2012 | Qiao |
| 2012/0277729 A1 | 11/2012 | Melsheimer |
| 2013/0131641 A1 | 5/2013 | Jimenez et al. |
| 2013/0190565 A1 | 7/2013 | Gora et al. |
| 2013/0274553 A1 | 10/2013 | Piskun |
| 2013/0338440 A1 | 12/2013 | Sinai et al. |
| 2014/0005683 A1 | 1/2014 | Stand et al. |
| 2014/0073853 A1 | 3/2014 | Swisher et al. |
| 2014/0081169 A1 | 3/2014 | Gerding et al. |
| 2014/0088459 A1 | 3/2014 | Roush et al. |
| 2014/0142393 A1 | 5/2014 | Piskun et al. |
| 2014/0155702 A1 | 6/2014 | Tilson et al. |
| 2014/0155783 A1 | 6/2014 | Starksen et al. |
| 2014/0188054 A1 | 7/2014 | Iijima et al. |
| 2014/0234600 A1 | 8/2014 | Wang et al. |
| 2014/0243873 A1 | 8/2014 | Franklin |
| 2014/0275860 A1 | 9/2014 | Rottenberg et al. |
| 2014/0276601 A1 | 9/2014 | Edward |
| 2014/0276642 A1 | 9/2014 | Cully et al. |
| 2014/0343358 A1 | 11/2014 | Hameed et al. |
| 2014/0371764 A1 | 12/2014 | Oyola et al. |
| 2015/0018616 A1 | 1/2015 | Kumoyama |
| 2015/0038919 A1 | 2/2015 | Bramwell et al. |
| 2015/0073216 A1 | 3/2015 | Papay |
| 2015/0073409 A1 | 3/2015 | Watson et al. |
| 2015/0094656 A1 | 4/2015 | Salahieh et al. |
| 2015/0119640 A1 | 4/2015 | Reydel |
| 2015/0126814 A1 | 5/2015 | Mesallum et al. |
| 2015/0133729 A1 | 5/2015 | Reydel |
| 2015/0142013 A1 | 5/2015 | Tanner et al. |
| 2015/0148602 A1 | 5/2015 | Hill et al. |
| 2015/0148606 A1 | 5/2015 | Rottenberg et al. |
| 2015/0164314 A1 | 6/2015 | Peterson |
| 2015/0216589 A1* | 8/2015 | Wittenberger .... A61M 25/0147 604/95.04 |
| 2015/0342608 A1 | 12/2015 | Hernandez |
| 2015/0369325 A1 | 12/2015 | Bureau et al. |
| 2016/0007832 A1 | 1/2016 | Shimada |
| 2016/0015259 A1 | 1/2016 | Mody et al. |
| 2016/0058268 A1 | 3/2016 | Salman et al. |
| 2016/0066773 A1 | 3/2016 | Cooper et al. |
| 2016/0096004 A1 | 4/2016 | Gerrans et al. |
| 2016/0129547 A1 | 5/2016 | Duescher et al. |
| 2016/0136393 A1 | 5/2016 | Tsai et al. |
| 2016/0174829 A1 | 6/2016 | Reydel |
| 2016/0198935 A1 | 7/2016 | Choi et al. |
| 2016/0270870 A1 | 9/2016 | Kowshik |
| 2016/0287059 A1 | 10/2016 | Ha et al. |
| 2016/0324412 A1 | 11/2016 | Hassidov et al. |
| 2017/0156567 A1* | 6/2017 | Kaneko ................ A61B 1/0011 |
| 2017/0157363 A1 | 6/2017 | Barrish et al. |
| 2017/0340862 A1 | 11/2017 | Calabrese et al. |
| 2017/0360281 A1 | 12/2017 | Ponsky |
| 2018/0015257 A1 | 1/2018 | Krolik et al. |
| 2018/0064366 A1 | 3/2018 | Sweeney et al. |
| 2018/0085559 A1 | 3/2018 | Laby et al. |
| 2018/0132705 A1 | 5/2018 | Higuchi |
| 2018/0184885 A1 | 7/2018 | St. George |
| 2018/0249893 A1 | 9/2018 | Yeung et al. |
| 2018/0263469 A1 | 9/2018 | Okaniwa et al. |
| 2018/0264239 A1 | 9/2018 | Piskun |
| 2018/0271354 A1 | 9/2018 | Tilson et al. |
| 2018/0289925 A1 | 10/2018 | Palmer |
| 2018/0326197 A1 | 11/2018 | McArthur et al. |
| 2018/0361116 A1 | 12/2018 | Quick et al. |
| 2018/0374603 A1 | 12/2018 | Greenwood |
| 2019/0046012 A1 | 2/2019 | Ikeda |
| 2019/0223710 A1 | 7/2019 | Tilson et al. |
| 2020/0100653 A1 | 4/2020 | Nakamura |
| 2020/0171276 A1 | 6/2020 | Onozuka |
| 2020/0315429 A1 | 10/2020 | Russo et al. |
| 2020/0315433 A1 | 10/2020 | Axon et al. |
| 2020/0383677 A1 | 12/2020 | Piligian et al. |
| 2021/0030260 A1 | 2/2021 | Julian et al. |
| 2021/0137366 A1 | 5/2021 | Tilson et al. |
| 2021/0138187 A1 | 5/2021 | Tilson et al. |
| 2023/0001134 A1 | 1/2023 | Tilson et al. |
| 2023/0014281 A1 | 1/2023 | Tilson et al. |
| 2023/0338702 A1 | 10/2023 | Tilson et al. |
| 2024/0188805 A1 | 6/2024 | Tilson et al. |

FOREIGN PATENT DOCUMENTS

| | | |
|---|---|---|
| CN | 1706349 A | 12/2005 |
| CN | 1732855 A | 2/2006 |
| CN | 1806770 A | 7/2006 |
| CN | 1861011 A | 11/2006 |
| CN | 101119765 A | 2/2008 |
| CN | 101129255 A | 2/2008 |
| CN | 101888872 A | 11/2010 |
| CN | 102137628 A | 7/2011 |
| CN | 201899767 U | 7/2011 |
| CN | 102711585 A | 10/2012 |
| CN | 102872519 A | 1/2013 |
| CN | 103384500 A | 11/2013 |
| CN | 104168860 A | 11/2014 |
| CN | 104287684 B | 3/2016 |
| CN | 105759418 A | 7/2016 |
| CN | 105813536 A | 7/2016 |
| CN | 105832279 A | 8/2016 |
| CN | 106137397 A | 11/2016 |
| CN | 106455929 A | 2/2017 |
| CN | 106488744 A | 3/2017 |
| CN | 106659367 A | 5/2017 |
| CN | 106823102 A | 6/2017 |
| CN | 107296584 A | 10/2017 |
| CN | 107697631 A | 2/2018 |
| DE | 102005039601 A1 | 2/2007 |
| EP | 401129 A1 | 12/1990 |
| EP | 0941743 A2 | 9/1999 |
| EP | 1662972 A2 | 6/2006 |
| EP | 1695657 A1 | 8/2006 |
| EP | 1487318 B1 | 3/2008 |
| EP | 2016914 A2 | 1/2009 |

(56) References Cited

FOREIGN PATENT DOCUMENTS

| | | |
|---|---|---|
| EP | 1499227 B1 | 10/2010 |
| EP | 2258322 A2 | 12/2010 |
| EP | 2364637 A1 | 9/2011 |
| EP | 2368481 A1 | 9/2011 |
| EP | 2368483 A1 | 9/2011 |
| EP | 3256052 A1 | 12/2017 |
| EP | 2604175 B1 | 11/2019 |
| GB | 2482355 A | 10/2010 |
| GB | 2497544 A | 6/2013 |
| JP | H05220102 A | 8/1993 |
| JP | H05293077 A | 11/1993 |
| JP | H0644503 U | 6/1994 |
| JP | 2002125921 A | 5/2002 |
| JP | 2003501197 A | 1/2003 |
| JP | 2005152300 A | 6/2005 |
| JP | 2005323778 A | 11/2005 |
| JP | 03965108 B2 | 8/2007 |
| JP | 2009506839 A | 2/2009 |
| JP | 2009507617 A | 2/2009 |
| JP | 2009061173 A | 3/2009 |
| JP | 2010000360 A | 1/2010 |
| JP | 2011194126 A | 10/2011 |
| JP | 2012183232 A | 9/2012 |
| JP | 2013176465 A | 9/2013 |
| JP | 2014124475 A | 7/2014 |
| JP | 2015525609 A | 9/2015 |
| JP | 2018500054 A | 1/2018 |
| JP | 2018514350 A | 6/2018 |
| JP | 2018537229 A | 12/2018 |
| KR | 10-2015-0131502 A | 11/2015 |
| KR | 20180053852 A | 5/2018 |
| WO | WO97/43941 A1 | 11/1997 |
| WO | WO99/053827 A1 | 10/1999 |
| WO | WO03/013348 A1 | 2/2003 |
| WO | WO2005/110199 A1 | 11/2005 |
| WO | WO2005/110200 A1 | 11/2005 |
| WO | WO2007/035931 A2 | 3/2007 |
| WO | WO2008/041809 A1 | 4/2008 |
| WO | WO2008/122969 A1 | 10/2008 |
| WO | WO2008/122997 A1 | 10/2008 |
| WO | WO2009/154192 A1 | 12/2009 |
| WO | WO2011/018147 A1 | 2/2011 |
| WO | WO2011/018157 A1 | 2/2011 |
| WO | WO2011/148172 A2 | 12/2011 |
| WO | WO2012/054480 A2 | 4/2012 |
| WO | WO2012/080947 A1 | 6/2012 |
| WO | WO2012/122288 A2 | 9/2012 |
| WO | WO2016/034598 A1 | 3/2016 |
| WO | WO2017/041052 A1 | 3/2017 |
| WO | WO2018/035452 A1 | 8/2017 |
| WO | WO2019/018682 A1 | 1/2019 |
| WO | WO2019/054867 A1 | 3/2019 |
| WO | WO2019/160865 A1 | 8/2019 |
| WO | WO2019/232354 A1 | 12/2019 |
| WO | WO2020/018934 A1 | 1/2020 |

OTHER PUBLICATIONS

Filip et al. Design, Implementation, and Testing of Miniature Self-Stabilizing Capsule Endoscope with wireless image transmission Capabilities. (Year: 2011).*

Tilson et al.; U.S. Appl. No. 17/604,203 entitled "Dynamically rigidizing composite medical structures," filed Oct. 15, 2021.

Tilson et al.; U.S. Appl. No. 17/644,758 entitled "Device for endoscopic advancement through the small intestine," filed Dec. 16, 2021.

Loeve et al.; Endoscope Shaft-Rigidity Control Mechanism: "Forguide"; IEEE Trans. On Biomed. Eng.; 59(2); pp. 542-551; Feb. 2012.

Shah et al.; Magnetic Imaging of Colonoscopy: An Audit of Looping, Accuracy and Ancillary maneuvers; Gastrointest. Endosc.; 52(1); pp. 1-8; Jul. 1, 2000.

Simi et al.; Design, Fabrication, and Testing of a Capsule With Hybrid Locomotion for Gastrointestinal Tract Exploration; IEEE/ASME Trans on Mechatronics; 15(2); pp. 170-x; Apr. 2010.

Valdastri et al.; Advanced Technologies for Gastrointestinal Endoscopy; Annu. Rev. Biomed. Eng.; 14; pp. 397-429; May 2012.

Zhao et al.; Development of a variable stiffness over tube based on low-melting-point-alloy for endoscopic surgery; J. Med. Devices; 10(2); 8 pages; May 12, 2016.

Tilson et al.; U.S. Appl. No. 17/493,785 entitled "Dynamically rigidizing composite medical structures," filed Oct. 4, 2021.

Tilson et al.; U.S. Appl. No. 17/448,188 entitled "Device and method for enhanced visualization of the small intestine," filed Sep. 20, 2021.

Loeve et al.; Vacuum packed particles as flexible endoscope guides with controllable rigidity; Granular Matter; 12(6); pp. 543-554; Jun. 24, 2010.

Gomes et al.; U.S. Appl. No. 18/044,027 entitled "Dynamically rigidizing guiderail and methods of use," filed Mar. 3, 2023.

Dow, Dow white paper: Can you estimate modulus from durometer hardness for silicones: Yes, but you only roughly and you must choose your modulus carefully!; 5 pages; retrieved from the internet (https://www.dow.com/content/dam/doc/documents/en-us/tech-art/11/11-37/11-3716-01-durometer-hardness-for-silicones.pdf) on Jan. 18, 2023.

Lopez et al.; U.S. Appl. No. 17/995,294 entitled "Layered walls for rigidizing devices," filed Sep. 30, 2022.

Scheeff et al.; U.S. Appl. No. 18/000,062 entitled "Rigidizing devices," filed Nov. 28, 2022.

Tilson et al.; U.S. Appl. No. 18/325,974 entitled "Endscope sheath apparatuses," filed May 30, 2023.

Tilson et al.; U.S. Appl. No. 18/325,979 entitled "Apparatuses and methods for determining if an endscope is contaminated," filed May 30, 2023.

Tilson et al.; U.S. Appl. No. 18/325,990 entitled "Multi-lumen port adapter mainfold devices and methods of use," filed May 30, 2023.

Gomes et al.; U.S. Appl. No. 18/263,517 entitled "Devices and methods to prevent inadvertent motion of dynamically rigidizing apparatuses," filed Jul. 28, 2023.

Bearing Works; PTFE Datasheet; 2 pages; Jan. 21, 2021 retrieved from the internet (https://www.bearingworks.com/uploaded-assets/pdfs/retainers/ptfe-datasheet.pdf) on Nov. 10, 2023.

Mayinger et al.; Disposable-sheath, flexible gastroscope system versus standard gastroscopes: a prospective, randomized trial; Gastrointestinal Endoscopy; 50(4); pp. 461-467; Oct. 1999.

Rothstein et al.; Disposable, sheathed, flexible sigmoidoscopy: a prospective, multicenter, randomized trial; Gastrointestinal Endoscopy; 41(6); pp. 566-572; Jun. 1995.

Sardinha et al.; Efficiency and productivity of a sheathed fiberoptic sigmoidoscope compared with a conventional sigmoidoscope; Diseases of the Colon and Rectum; 40(10); pp. 1248-1253; Oct. 1997.

Lopez et al.; U.S. Appl. No. 18/334,555 entitled "Layered walls for rididizing devices," filed Jun. 14, 2023.

Tilson et al.; U.S. Appl. No. 18/262,904 entitled "Large diameter hemostasis valves," filed Jul. 25, 2023.

Tilson et al.; U.S. Appl. No. 18/235,719 entitled "External working channels," filed Aug. 18, 2023.

Tanner et al.; U.S. Appl. No. 18/550,123 entitled "Control of robotic dynamically rigidizing composite medical structures," filed Sep. 11, 2023.

Gomes et al.; U.S. Appl. No. 18/837,186 entitled "Dynamically rigidizing composite medical structure," filed Aug. 8, 2024.

Tilson et al.; U.S. Appl. No. 18/858,743 entitled "Managing and manipulating a long length robotic endoscope," filed Oct. 21, 2024.

Witte et al.; U.S. Appl. No. 18/829,229 entitled "Pressure rigidization apparatuses and methods," filed Sep. 9, 2024.

Gomes et al.; U.S. Appl. No. 18/806,692 entitled "Devices and methods to prevent inadvertent motion of dynamically rigidizing apparatuses," filed Aug. 15, 2024.

Tilson et al.; U.S. Appl. No. 18/902,916 entitled "Methods of attaching a rigidizing sheath to an endoscope," filed Sep. 30, 2024.

Devengenzo et al.; U.S. Appl. No. 18/902,906 entitled "Telescoping robot," filed Sep. 30, 2024.

Tilson et al.; U.S. Appl. No. 18/809,322 entitled "Rigidizing overtube," filed Aug. 19, 2024.

Tilson et al.; U.S. Appl. No. 18/810,458 entitled "Rigidizing overtube," filed Aug. 20, 2024.

(56) References Cited

OTHER PUBLICATIONS

Mayinger et al.; Disposable protection for flexible gastroenterologie endoscopy: prospective comparative evaluation of a new gastroscopy system (Endosheath) compared to the standard fiberglass gastroscope; (English Abstract Only); Zeitschrift Fur Gastrenterologia; 36(6); pp. 501-507; Jun. 1998 (Eng Abs only).

Lopez et al.; U.S. Appl. No. 18/723,414 entitled "Methods and apparatuses for reducing curvature of a colon," filed Jun. 21, 2024.

Gomes et al.; U.S. Appl. No. 18/723,413 entitled "Obturator with stiff distal cannula engagement region," filed Jun. 21, 2024.

Morris et al.; U.S. Appl. No. 18/727,032 entitled "Reconfigurable rigidizing structures," filed Jul. 5, 2024.

Tilson et al.; U.S. Appl. No. 18/592,516 entitled "Device and method for enhanced visualization of the small intestine," filed Feb. 29, 2024.

Tilson et al.; U.S. Appl. No. 18/660,205 entitled "Device and method for enhanced visualiztion of the small intestine," filed May 9, 2024.

Tilson et al.; U.S. Appl. No. 18/751,188 entitled "Rigidzing overtube," filed Jun. 21, 2024.

Tilson et al.; U.S. Appl. No. 18/780,429 entitled "Device for endoscopic advancement through the small intestine," filed Jul. 22, 2024.

Eisler et al.; U.S. Appl. No. 18/852,419 entitled "Rigidizing aspiration systems and methods," filed Sep. 27, 2024.

Ferrante et al.; U.S. Appl. No. 18/851,053 entitled "Methods and apparatuses for navigating using a pair of rigidizing devices," filed Sep. 25, 2024.

Tilson et al.; U.S. Appl. No. 18/908,776 entitled "Methods of attaching a rigidizing sheath to an endoscope," filed Oct. 7, 2024.

\* cited by examiner

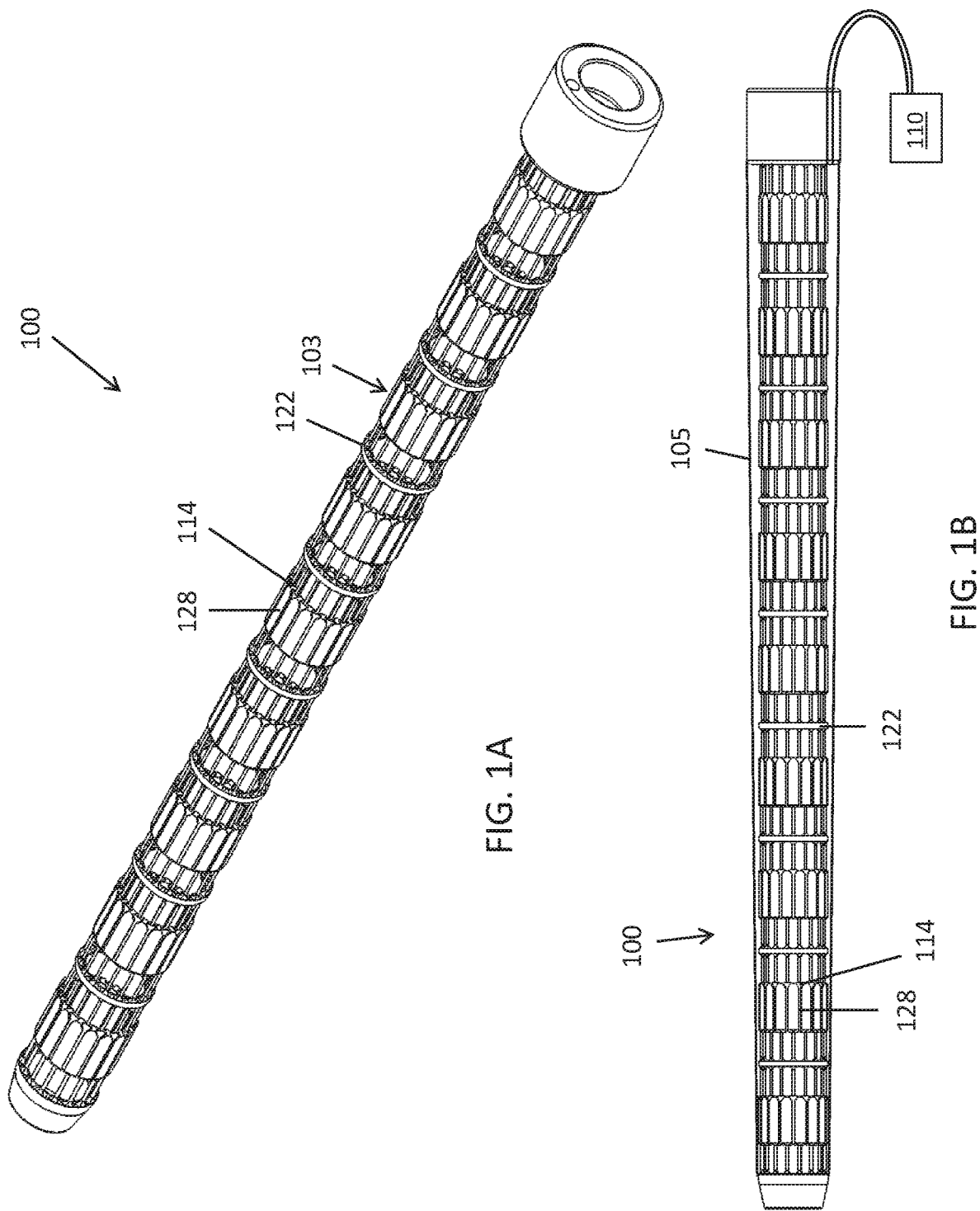

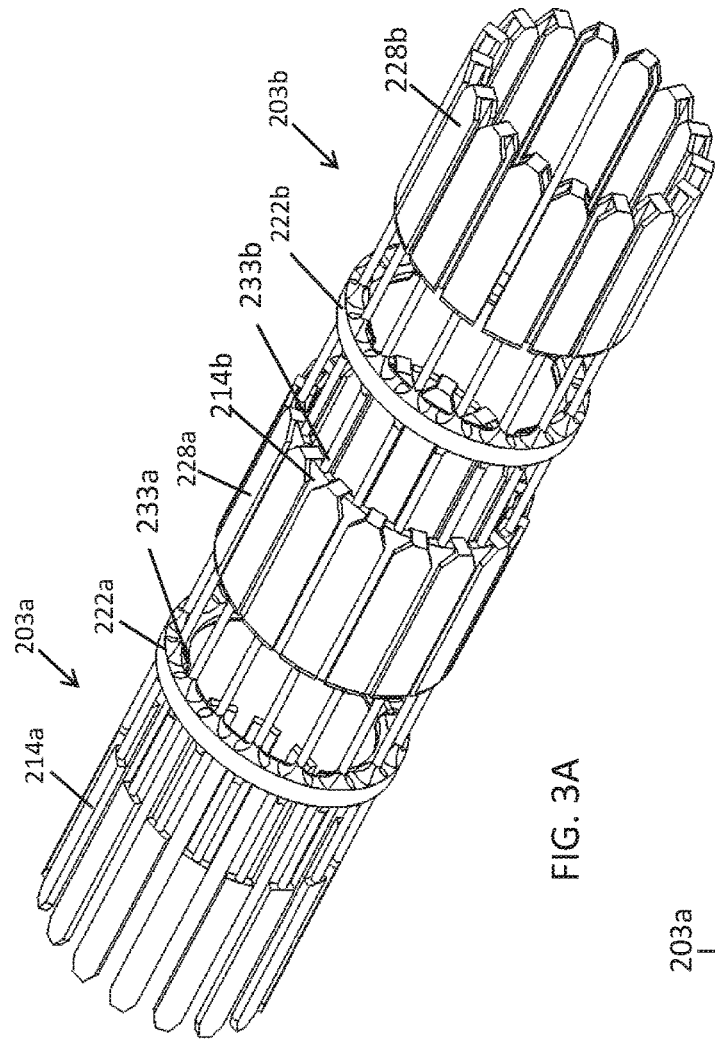
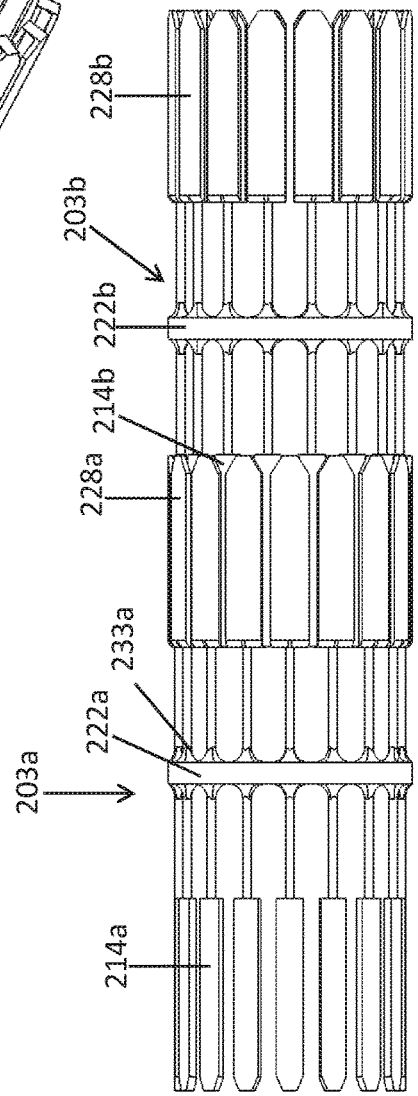
FIG. 3A
FIG. 3B

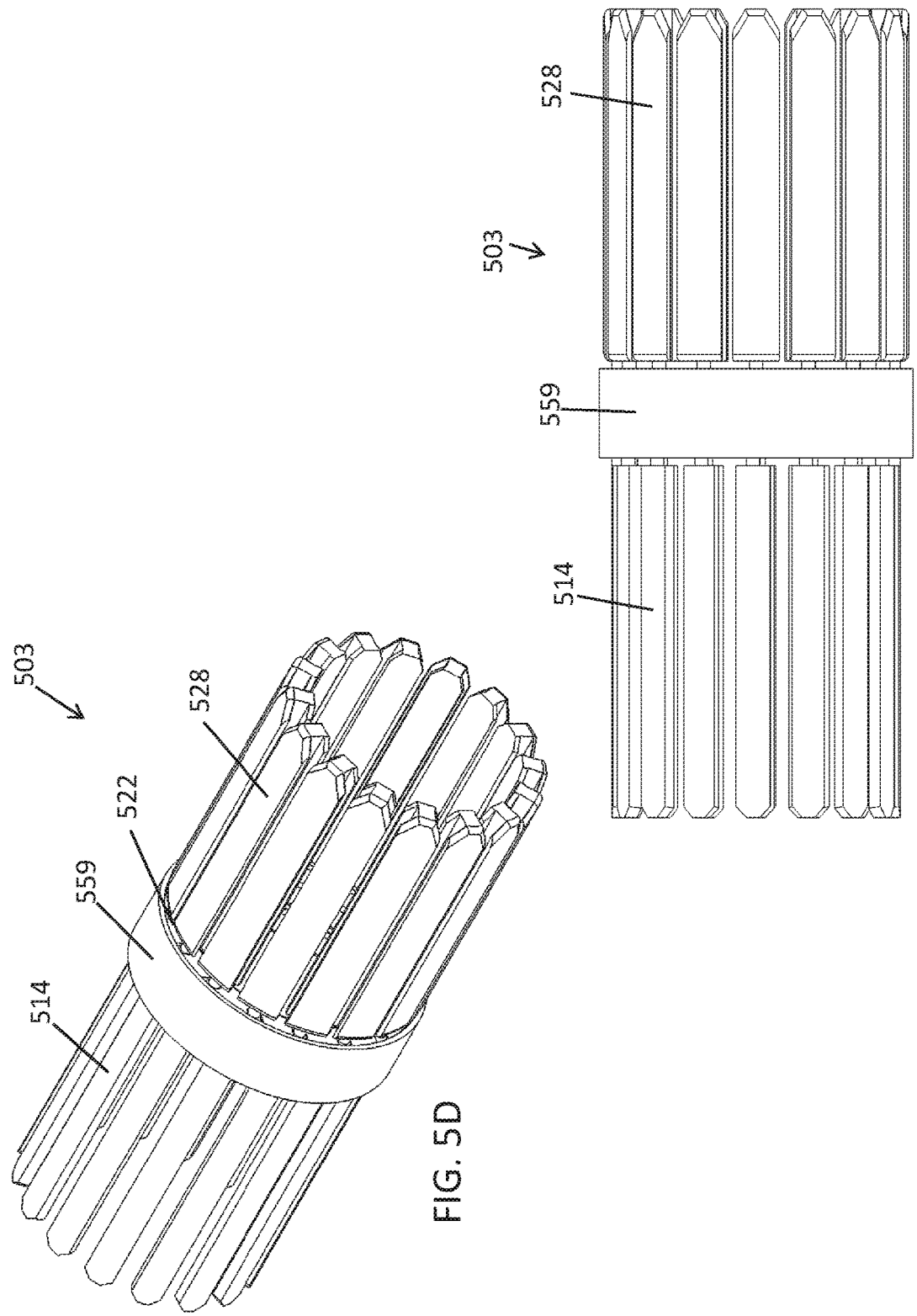

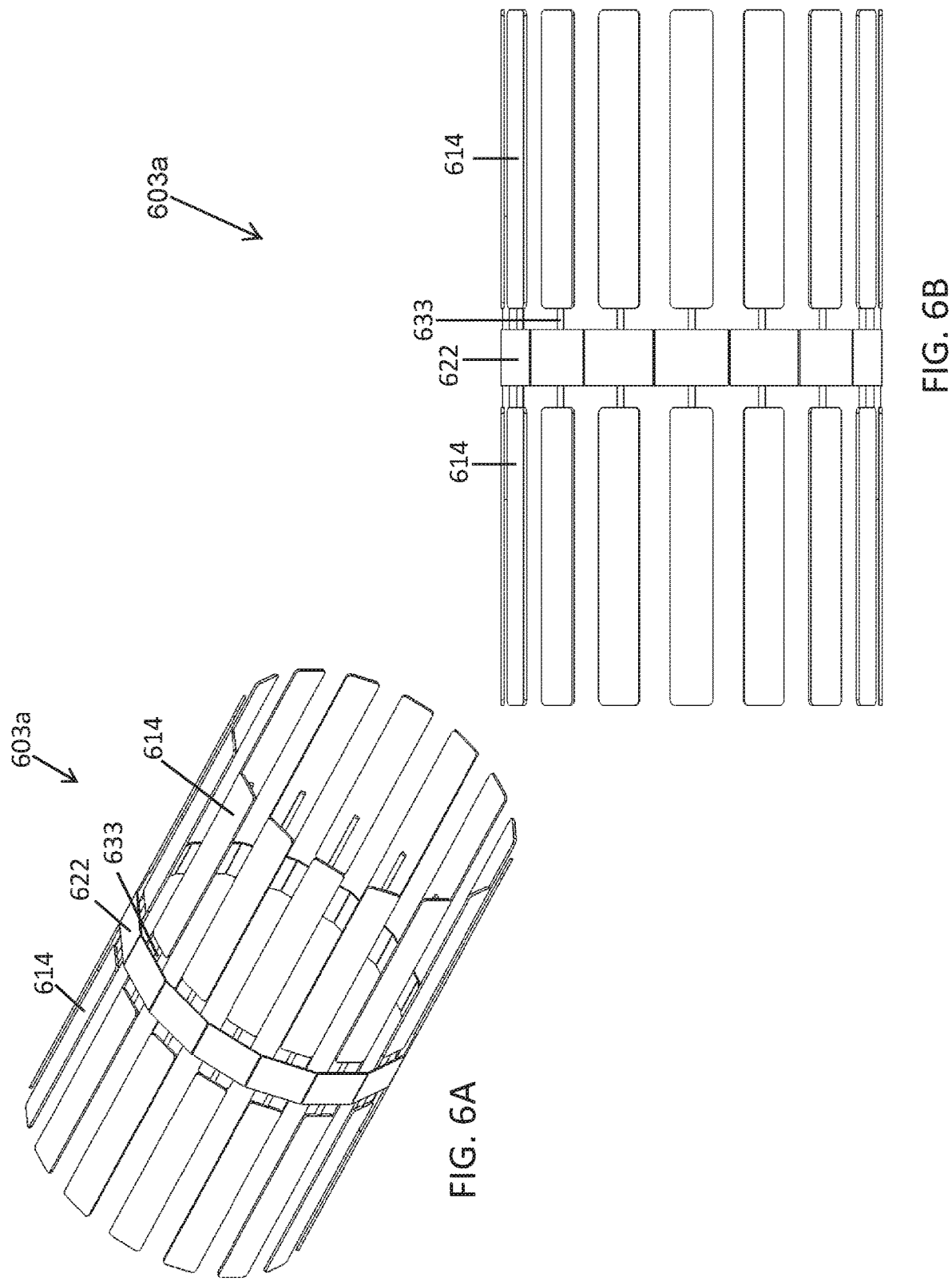

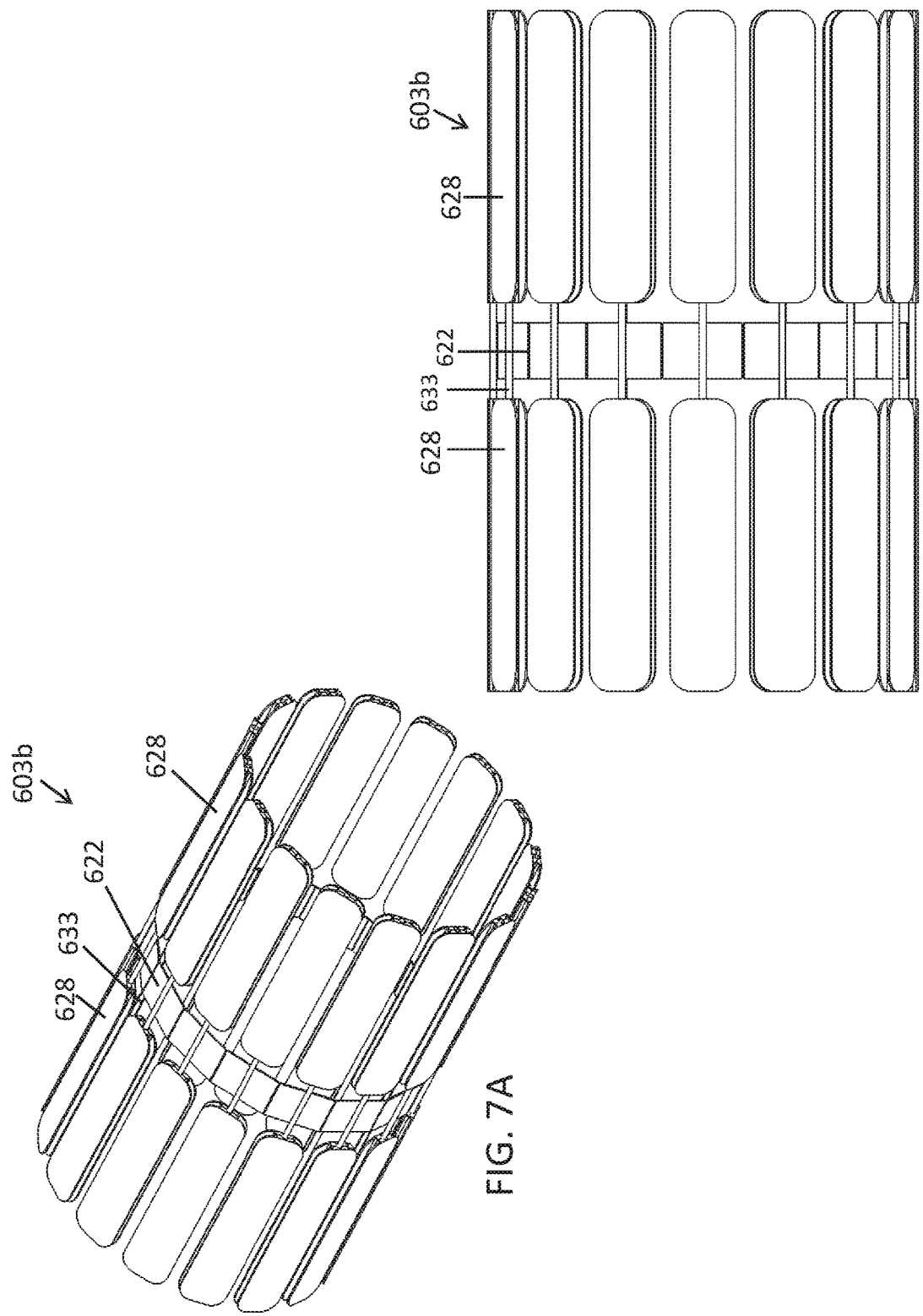

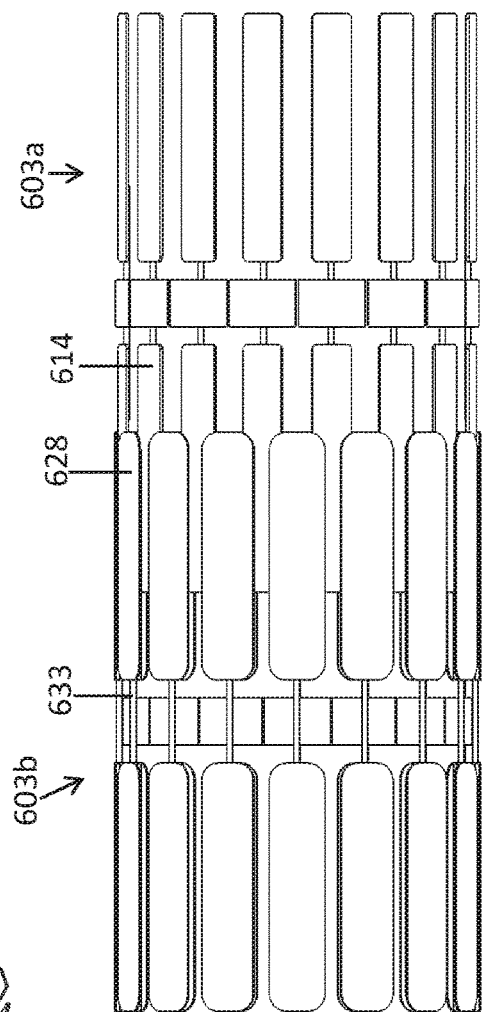
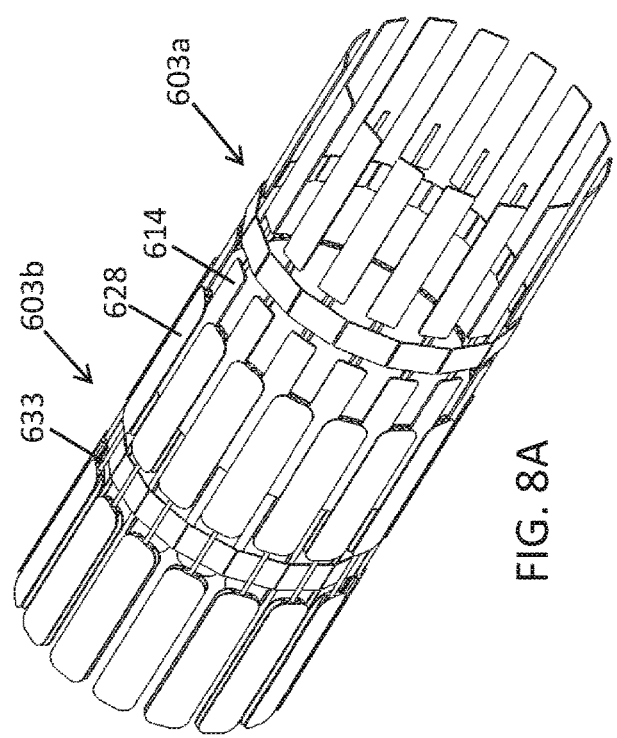
FIG. 8A
FIG. 8B

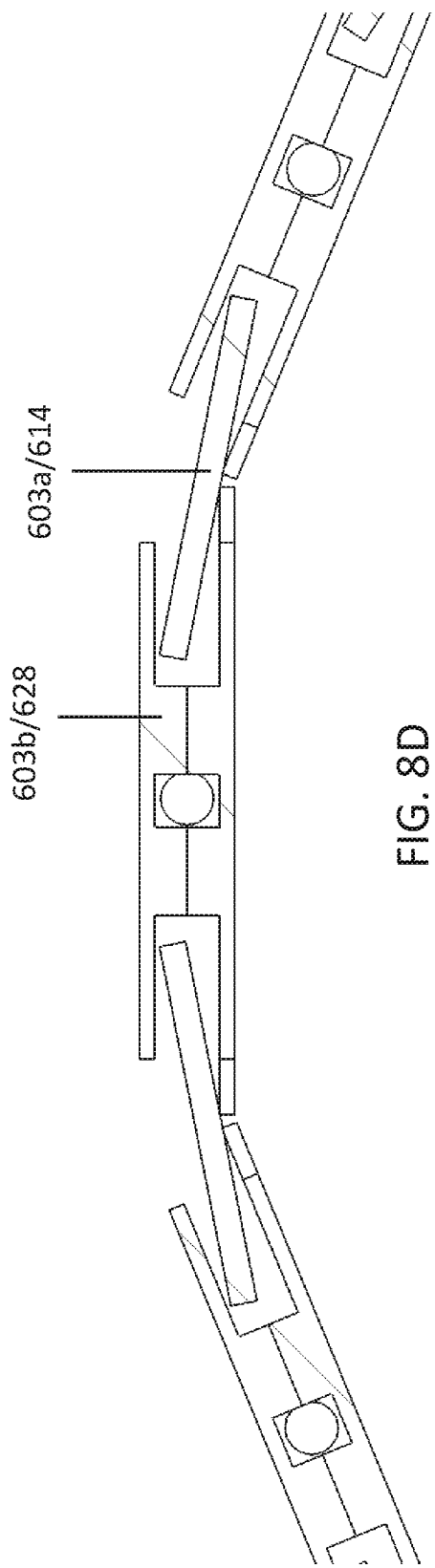

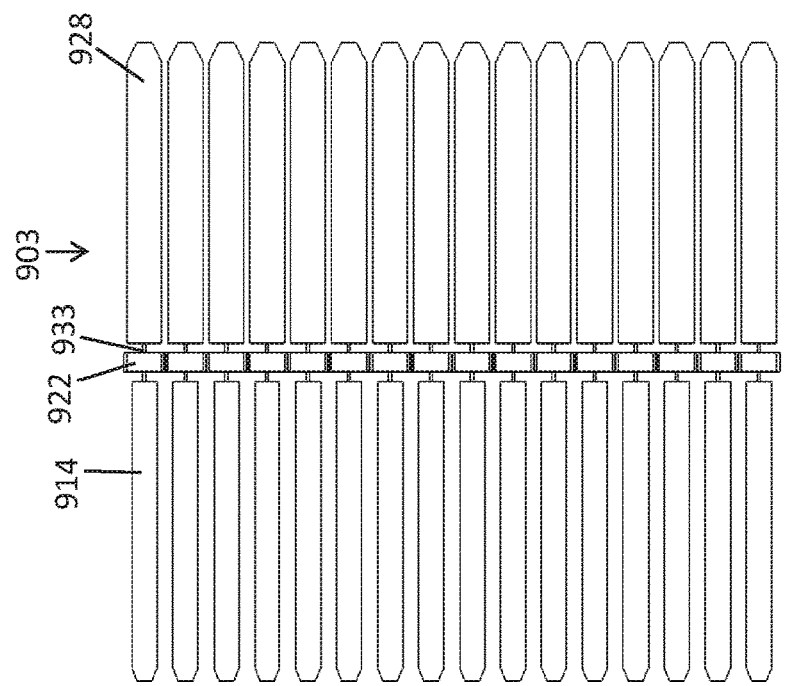
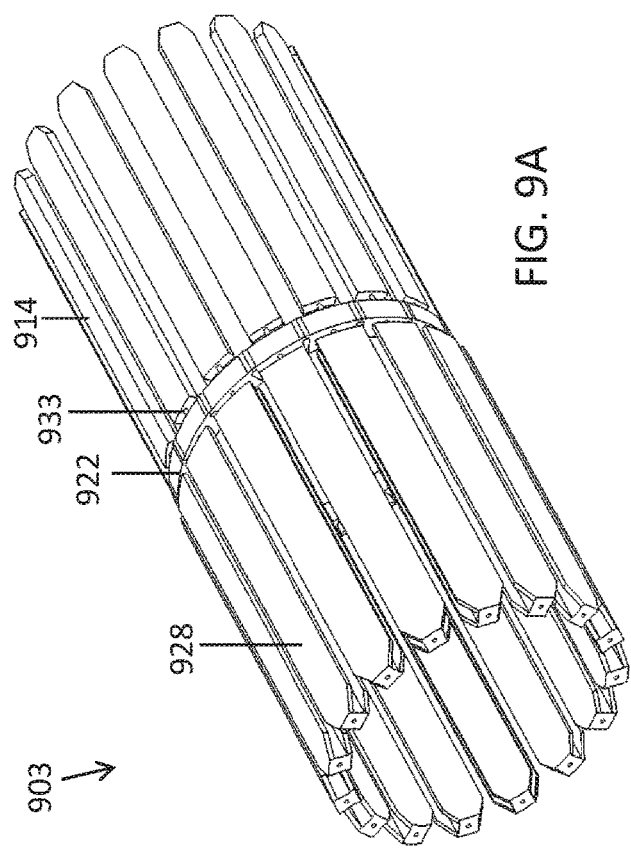
FIG. 9A
FIG. 9B

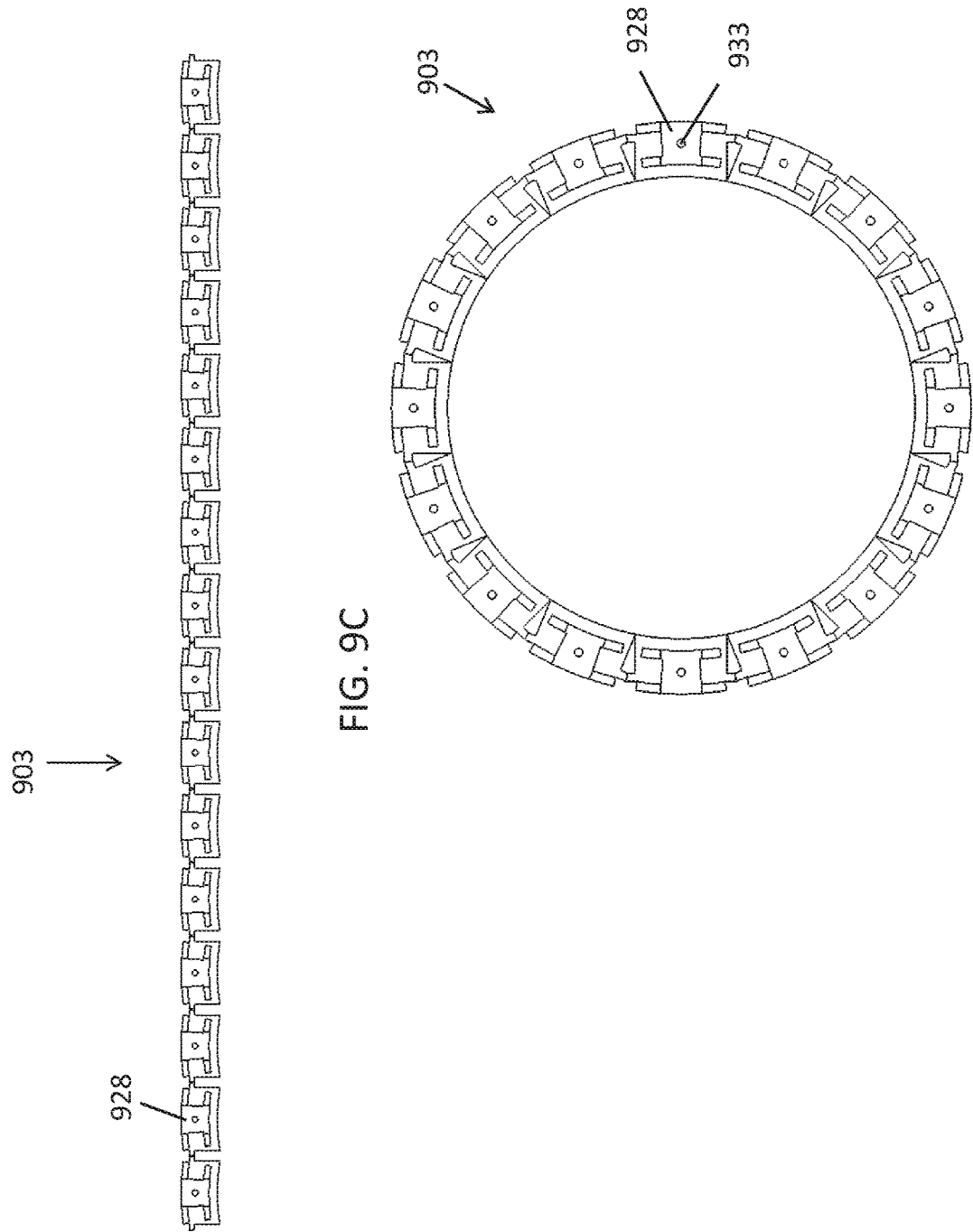

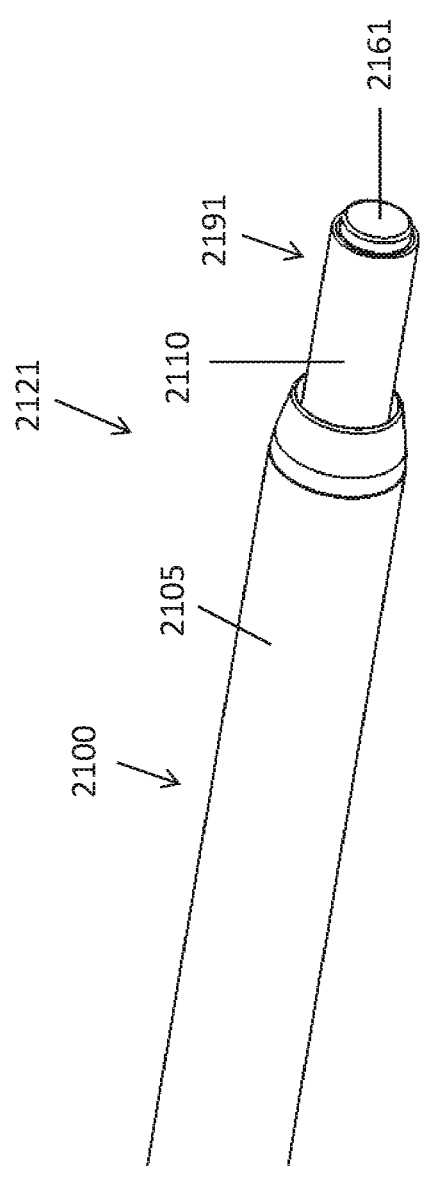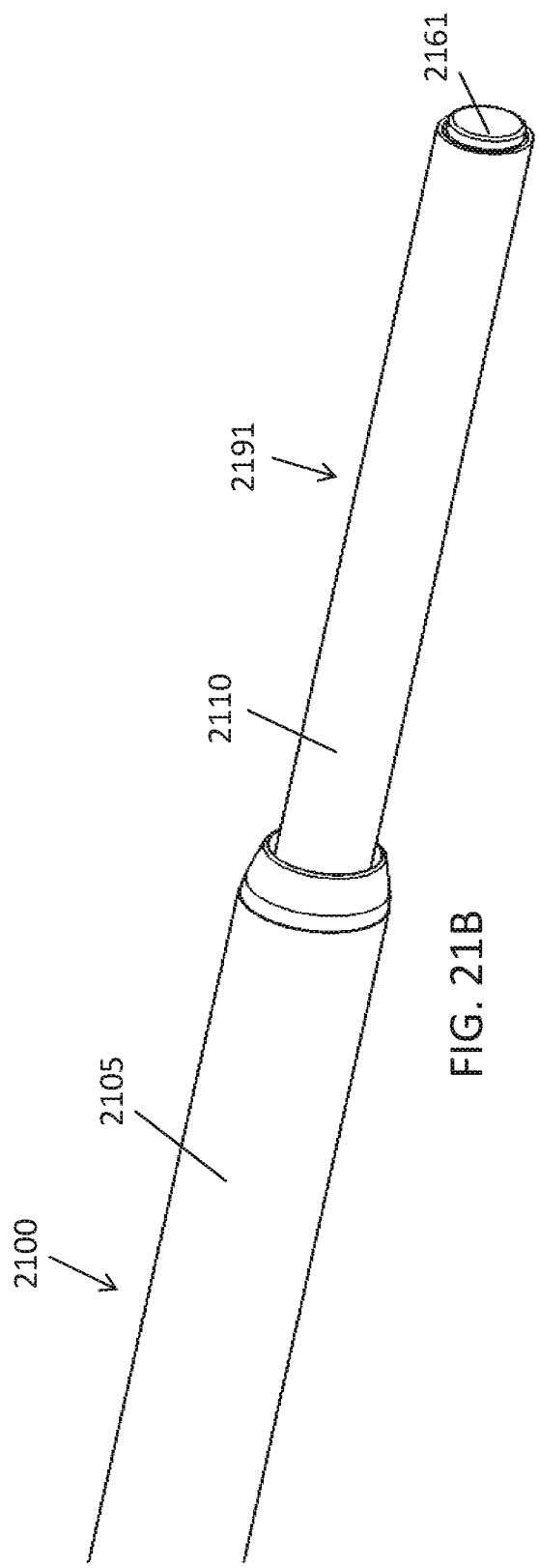
FIG. 21A
FIG. 21B

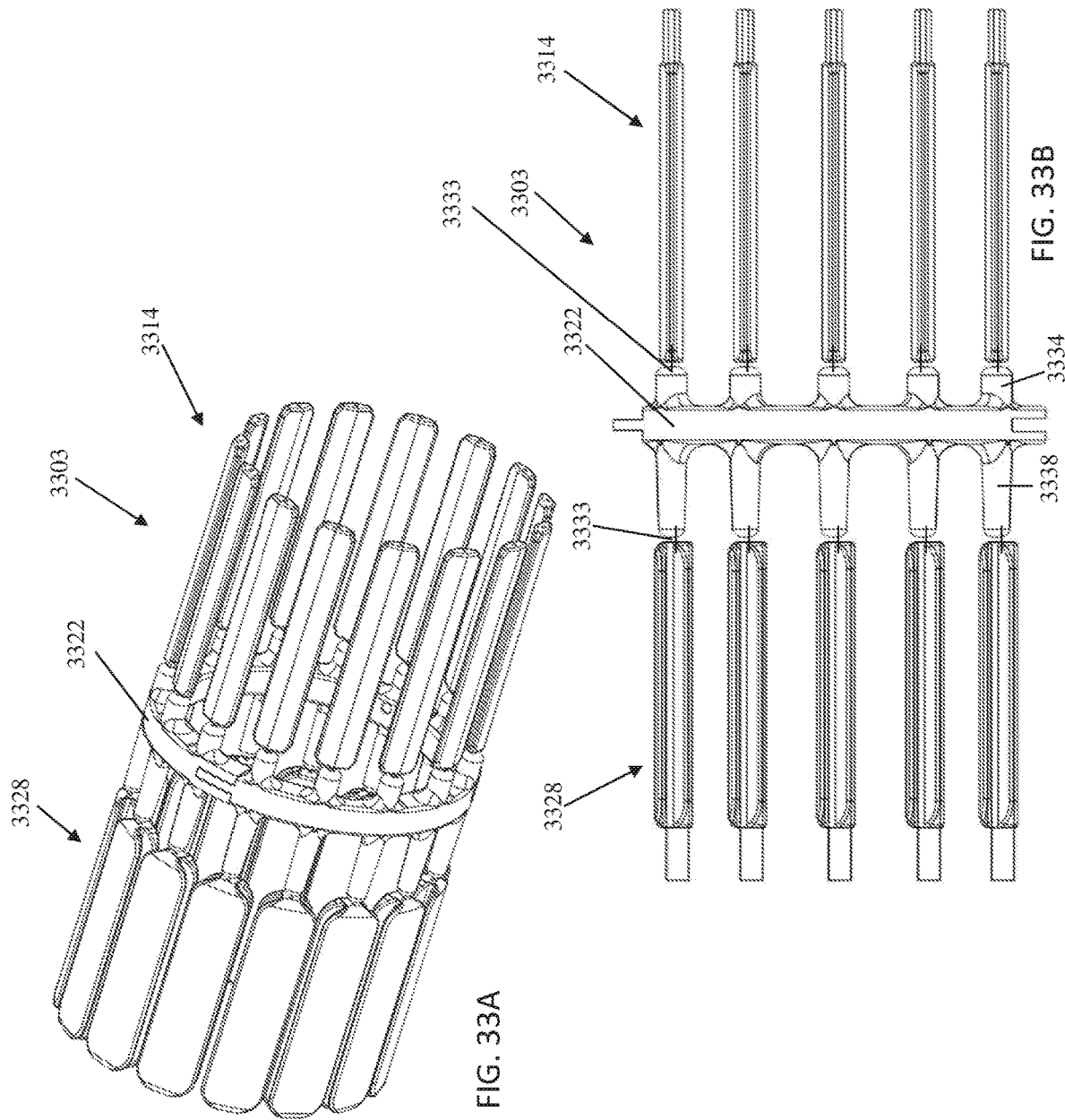

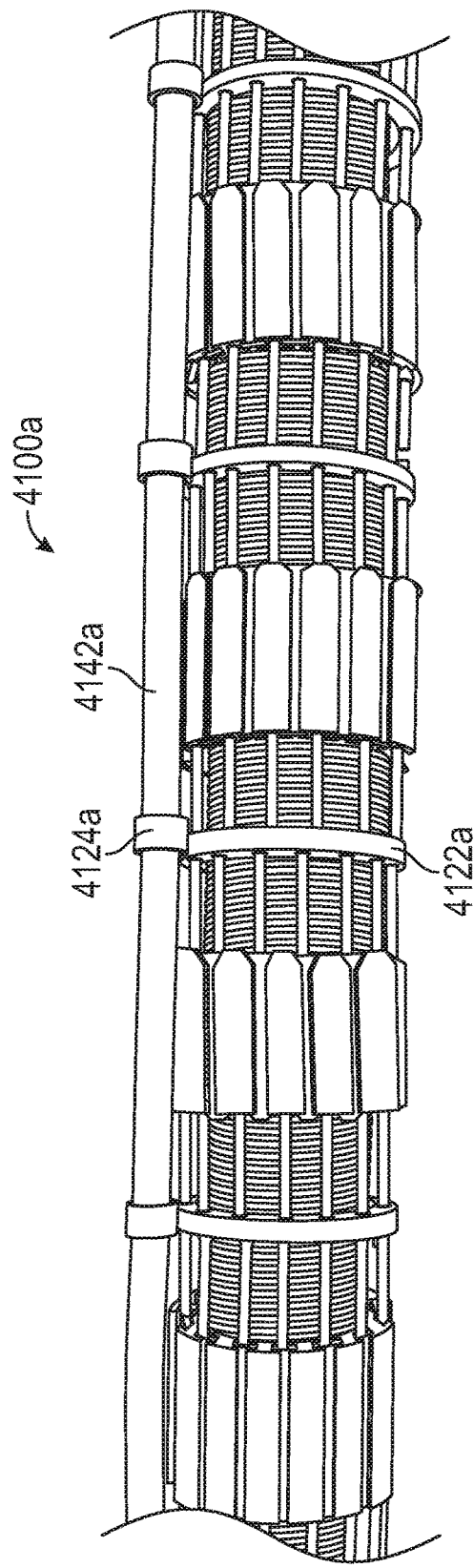
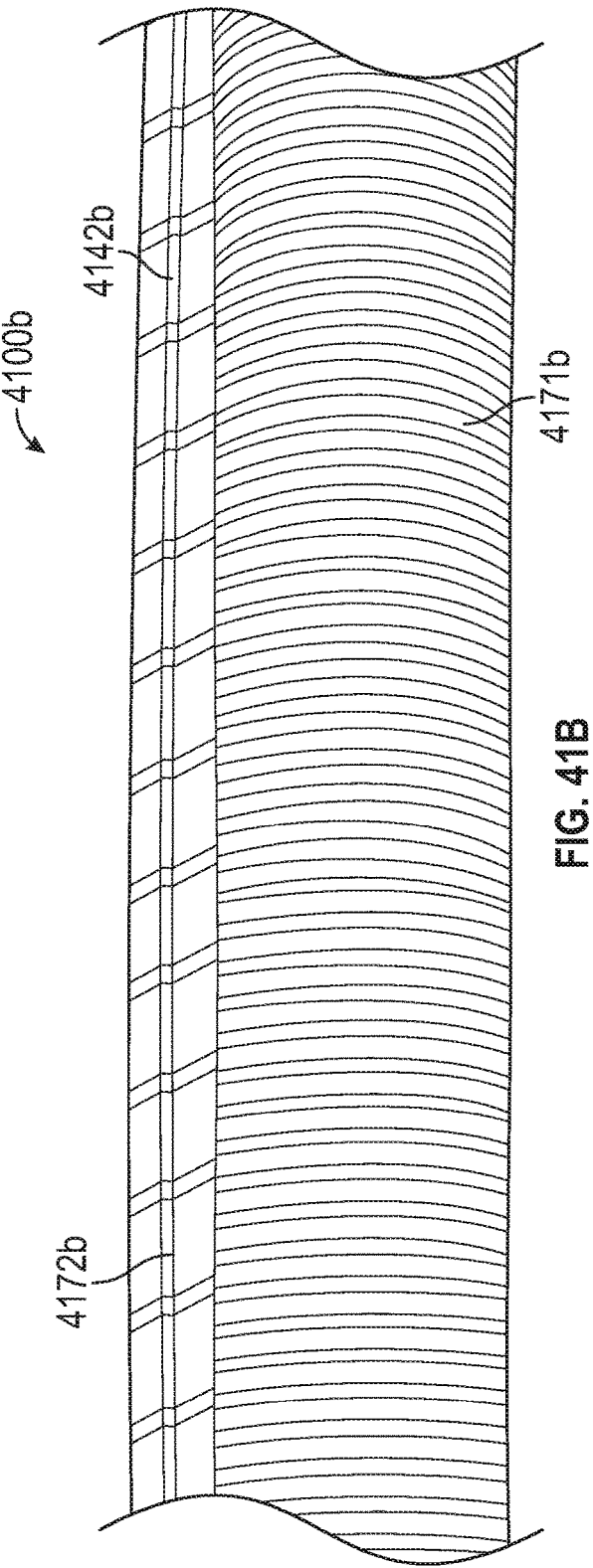
FIG. 41A
FIG. 41B

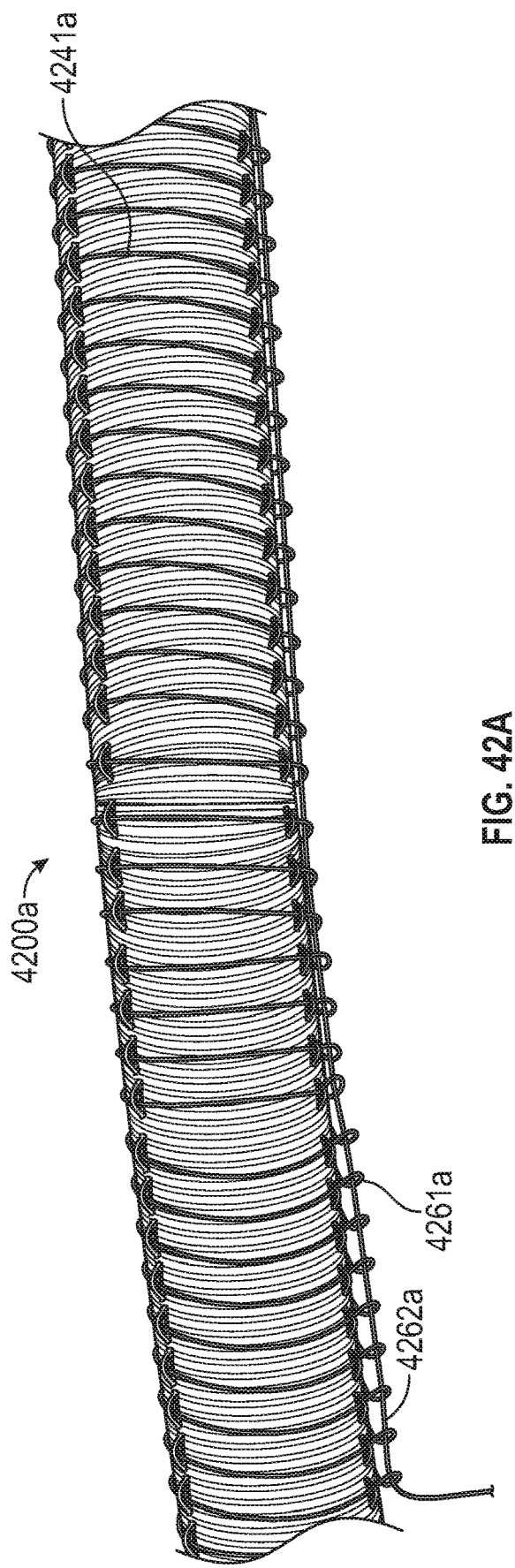
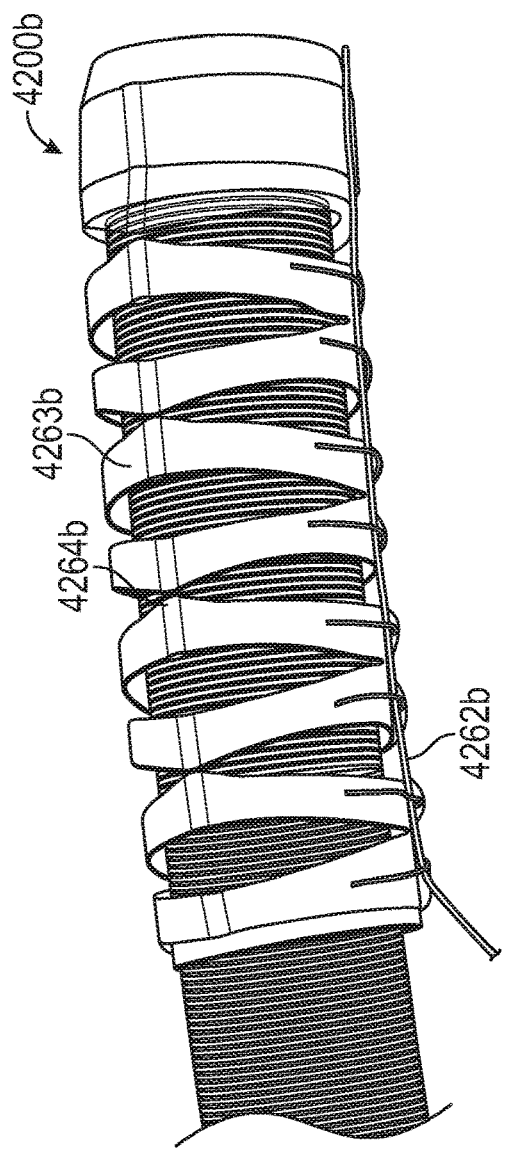
FIG. 42A
FIG. 42B

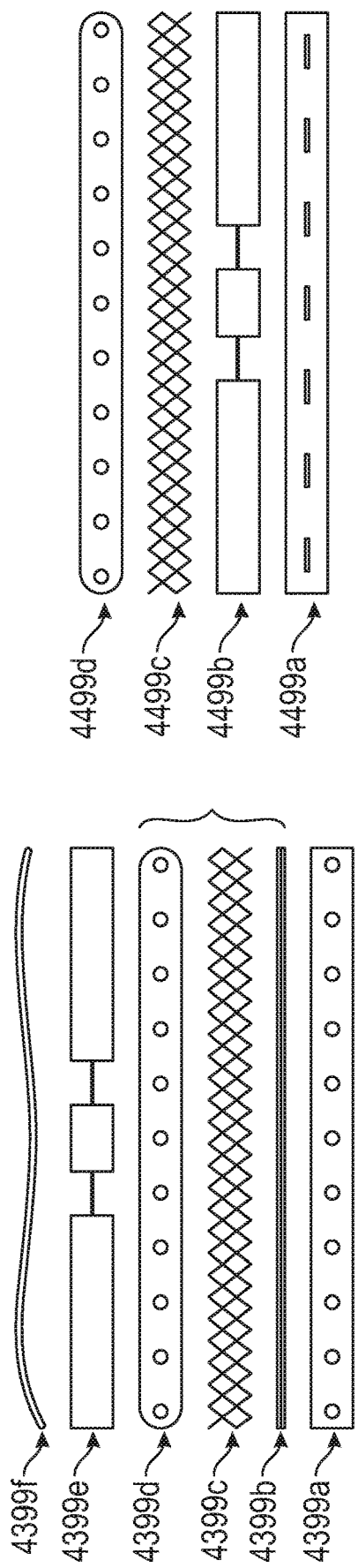
FIG. 43
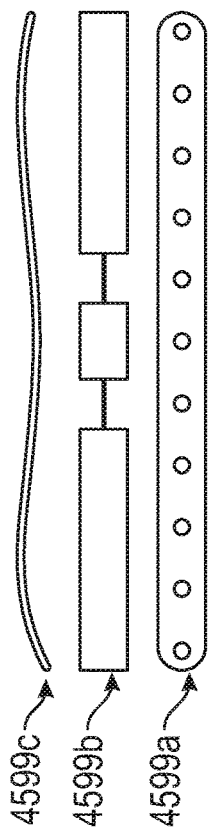
FIG. 44
FIG. 45

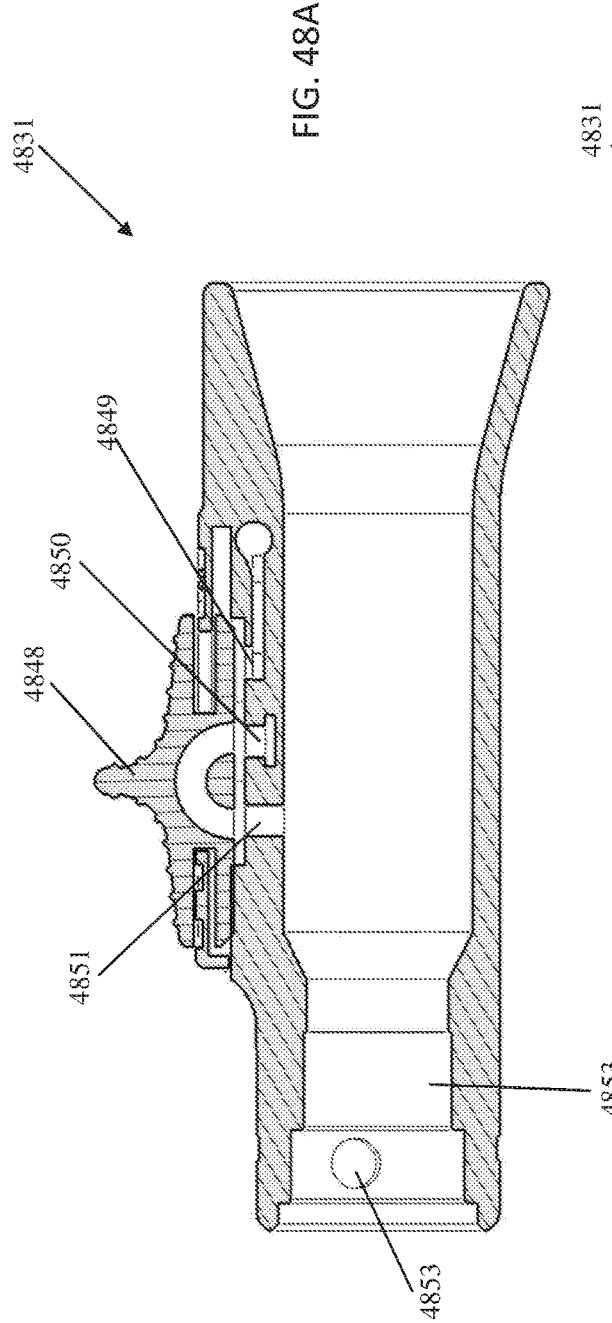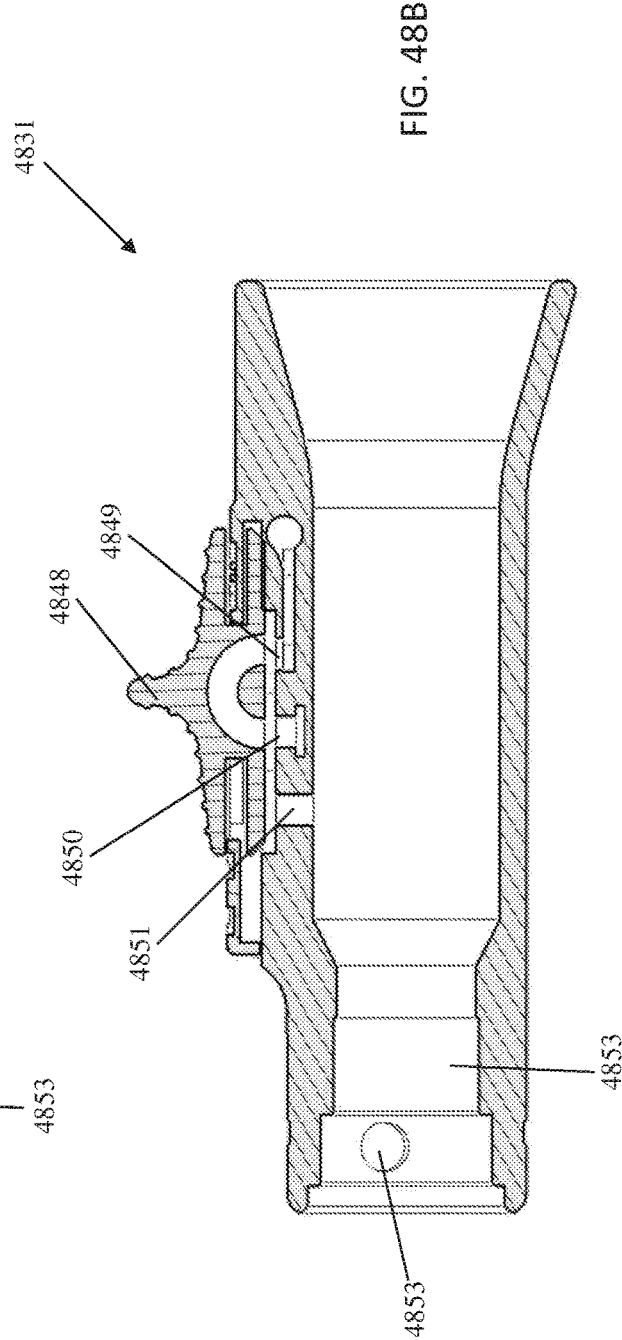

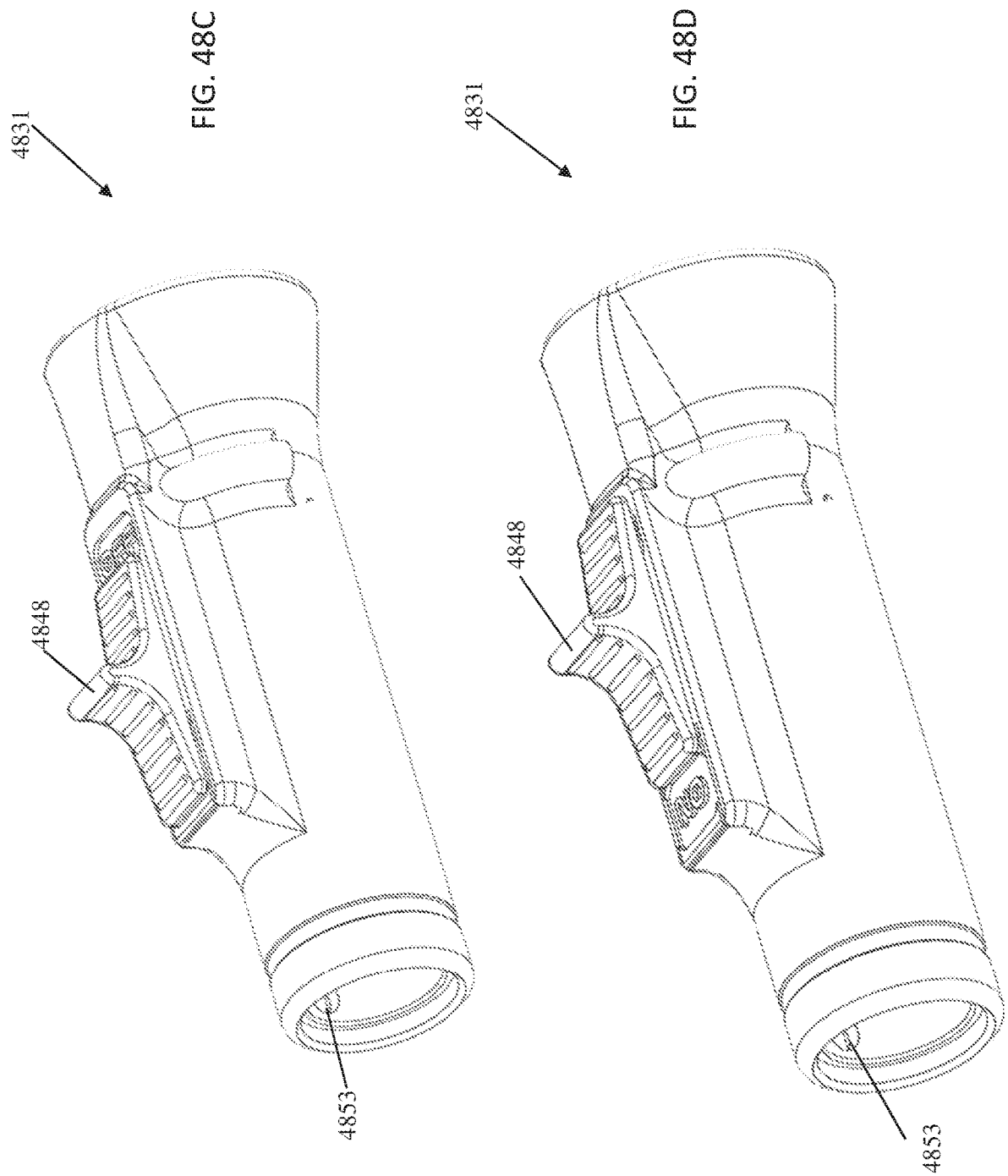

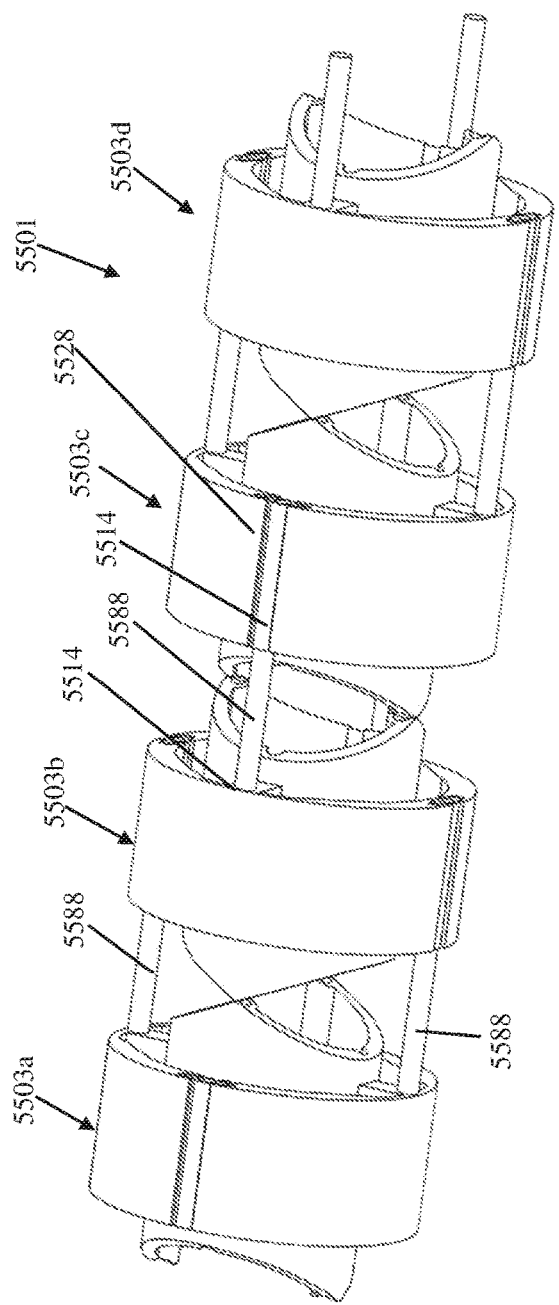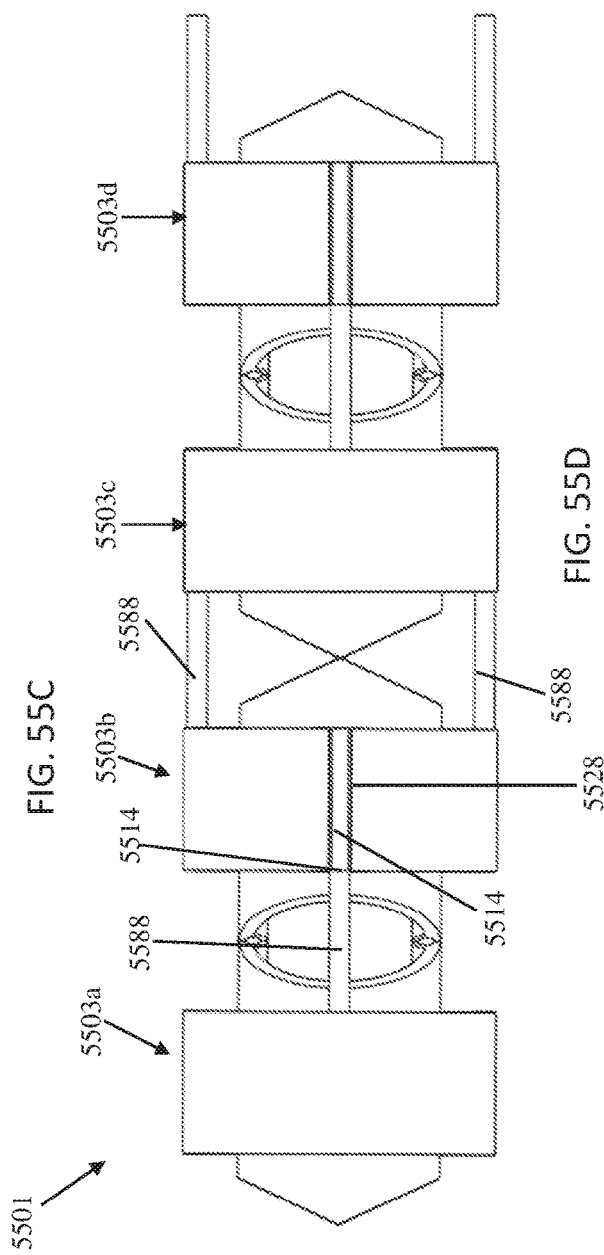

DYNAMICALLY RIGIDIZING OVERTUBE

CROSS REFERENCE TO RELATED APPLICATIONS

This application claims priority to U.S. Provisional Application No. 62/535,134, filed Jul. 20, 2017, titled "DYNAMICALLY RIGIDIZING OVERTUBE" and U.S. Provisional Application No. 62/672,444, filed May 16, 2018, titled "DYNAMICALLY RIGIDIZING OVERTUBE", the entireties of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

During endoscopic procedures, the endoscope can curve or loop through the vessel, making further advancement of the scope difficult. Such looping is a known clinical challenge for endoscopy. Indeed, one study found that looping occurred in 91 of 100 patients undergoing colonoscopy [Shah et al, "Magnetic Imaging of Colonoscopy: An Audit of Looping, Accuracy and Ancillary maneuvers." *Gastrointest Endosc* 2000; 52: 1-8]. Looping prolongs the procedure and can cause pain to the patient because it can stretch the vessel wall and the mesentery. Furthermore, looping leads to an increased incidence of perforations. In severe cases of looping, complete colonoscopies are impossible since looping stretches the length of the colon and the colonoscope is not long enough to reach the end. Looping is an impediment to precise tip control, denying the user the coveted one-to-one motion relationship between the handle and the endoscope tip. Such problems commonly occur across a wide range of endoscopic procedures, including colonoscopy, esophagogastroduodenoscopy (EGD), enteroscopy, endoscopic retrograde cholangiopancreatography (ERCP), recently developed interventional endoscopy procedures (including ESD (Endoscopic Submucosal Dissection) and EMR (Endoscopic Mucosal Resection)), robotic flexible endoscopy, and during NOTES (Natural Orifice Transluminal Endoscopic Surgery) procedures. Accordingly, there is a need for an endoscopic device that helps prevent looping and enables superior tip precision and control.

SUMMARY OF THE DISCLOSURE

Described herein are devices that can dynamically transition from a configuration of high flexibility to a configuration of high rigidity to help guide a medical device, such as an endoscope, through tortuous body lumens or within other bodily spaces.

In general, in one embodiment, a rigidizing overtube includes an elongate flexible tube, one or more mounting elements attached to the flexible tube, and a plurality of engagers connected to the one or more mounting elements. The rigidizing overtube has a flexible configuration in which the plurality of engagers are configured to move relative to other engagers to accommodate bending of the flexible tube. The rigidizing overtube has a rigid configuration in which the plurality of engagers are fixed relative to other engagers to prevent the flexible tube from bending.

This and other embodiments can include one or more of the following features. The rigidizing overtube can further include an outer layer positioned around the plurality of engagers. The overtube can be configured to attach to a source of vacuum such that application of vacuum transitions the rigidizing overtube from the flexible configuration to the rigid configuration. The plurality of engagers can be connected to the one or more mounting elements with a plurality of pivoting elements, each pivoting element connected to an engager. The plurality of pivoting elements can be ball and socket pivots, wires or cables, or narrow and thin extensions of the male and female engagers. Each of the plurality of engagers can be connected to a mounting element with an extensions and wire pivot. The extensions from each mounting ring can be longer on a first side of the mounting ring than on a second side of the mounting ring. The plurality of engagers can include a plurality of male engagers and a plurality of female engagers. The plurality of male engagers and plurality of female engagers can be positioned in an alternating arrangement around a circumference of the rigidizing overtube. The plurality of male engagers and plurality of female engagers can be positioned in an alternating arrangement along a longitudinal axis of the rigidizing overtube. The male engagers can have a double-wedge shaped cross section. An angle from a first side of the wedge to a second side of the wedge can be 20°-40°. The female engagers can have an I-shaped cross section. Inner surfaces of the I-shape can be angled at 10°-20°. The overtube can further include a plurality of motion stops configured to prevent the female engagers and male engagers from disengaging with one another when pulled apart axially.

In general, in one embodiment, a rigidizing overtube includes an elongate flexible tube, one or more mounting elements attached to the flexible tube, a plurality of female engagers connected to the one or more mounting elements, and a plurality of male engagers connected to the one or more mounting elements. The rigidizing overtube has a flexible configuration in which the plurality of male engagers are configured to move axially within and relative to the plurality of female engagers to accommodate bending of the flexible tube. The rigidizing overtube has a rigid configuration in which the plurality of male engagers are fixed relative to the female engagers to prevent the flexible tube from bending.

This and other embodiments can include one or more of the following features. The rigidizing overtube can further include an outer layer positioned around the plurality of male and female engagers. The overtube can be configured to attach to a source of vacuum such that application of vacuum transitions the rigidizing overtube from the flexible configuration to the rigid configuration. The plurality of male and female engagers can be connected to the one or more mounting elements with a plurality of pivoting elements, each pivoting element connected to one of the male or female engagers. The plurality of pivoting elements can be ball and socket elements, wires, or narrow and thin extensions of the male or female engagers. Each of the plurality of male and female engagers can be connected to one of the one or more mounting elements with an extensions and wire pivot. The extensions from each mounting ring can be longer on a first side of the mounting ring than a second side of the mounting ring. The plurality of male engagers and plurality of female engagers can be positioned in an alternating arrangement around a circumference of the rigidizing overtube. The plurality of male engagers and plurality of female engagers can be positioned in an alternating arrangement along a longitudinal axis of the rigidizing overtube. The male engagers can have a double wedge-shaped cross section. An angle from a first side of the wedge to a second side of the wedge can be 20°-40°. The female engagers can have an I-shaped cross section. Inner surfaces of the I-shape can be angled at 10°-20°. The overtube can further include a plurality of motion stops configured to prevent the female engagers and male engagers from disengaging with one another when pulled apart axially. The male engagers or the female engagers can include serrations thereon.

In general, in one embodiment, a rigidizing overtube includes an elongate flexible tube, one or more mounting elements attached to the flexible tube, and a plurality of first engagers connected to the one or more mounting elements through a plurality of pivoting mechanisms. The rigidizing overtube has a flexible configuration in which the plurality of engagers are configured to pivot about the pivoting mechanism to accommodate bending of the flexible tube. The rigidizing overtube has a rigid configuration in which plurality of engagers engage one another and prevent the flexible tube from bending.

This and other embodiments can include one or more of the following features. The rigidizing overtube can further include an outer layer positioned around the plurality of engagers. The overtube can be configured to attach to a source of vacuum such that application of vacuum transitions the rigidizing overtube from the flexible configuration to the rigid configuration. The plurality of pivoting mechanisms can be ball and socket elements, wires or cables, or narrow and thin extensions of the male or female engagers. The plurality of pivoting mechanisms can be wires, and the mounting elements can further include a plurality of extensions thereon, each extension extending from a wire of a pivoting mechanism to the mounting ring. Each pivoting mechanism can allow for pivoting of the first and second engagers at an angle of up to 30 degrees.

In general, in one embodiment, a method of advancing a medical device through a body lumen includes: (1) inserting an overtube having an elongate flexible tube and a plurality of engagers mounted thereto into the body lumen while the overtube is in a flexible configuration such that the plurality of engagers move axially relative to or pivot relative to one another as the flexible tube bends; and (2) when the overtube has reached a desired location in the body lumen, activating a vacuum over the plurality of engagers to transition the overtube into a rigid configuration such that movement or pivoting of the engagers is prevented and the flexible tube is prevented from bending.

This and other embodiments can include one or more of the following features. The method can further include passing a medical device through the overtube while the overtube is in the rigid configuration.

In general, in one embodiment, a rigidizing overtube includes a plurality of linkages and a plurality of tensile members. Each tensile member extends between neighboring linkages. Each linkage is connected together at one or more pivot points. The rigidizing overtube has a flexible configuration in which each tensile member is fixed relative to a first linkage and movable relative to a second linkage so as to allow pivoting between the first and second linkages. The rigidizing overtube has a rigid configuration in which each tensile member is fixed relative to the first and second linkages so as to prevent pivoting between the first and second linkages.

This and other embodiments can include one or more of the following features. The rigidizing overtube can further include an inner layer and an outer layer sandwiching the plurality of linkages therebetween. The overtube can be configured to attach to a source of vacuum such that application of vacuum transitions the rigidizing overtube from the flexible configuration to the rigid configuration. Each tensile member can include a first end that is movable with respect to a first of the neighboring linkages when the overtube is in the rigid configuration and a second end that is fixed with respect to a second of the neighboring linkages. The first end can include a male engager that is configured to move relative to a female engager of the second linkage.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1D show an exemplary embodiment of a dynamically rigidizing overtube.

FIGS. 3A-3C show connection of several of the linkages of FIGS. 2A-2C together.

FIGS. 5A-5E show an exemplary linkage of a dynamically rigidizing overtube including a ball and socket pivot.

FIGS. 6A-6B show another exemplary linkage of a dynamically rigidizing overtube that includes only male engagers.

FIGS. 7A-7B show another exemplary linkage of a dynamically rigidizing overtube that includes only female engagers.

FIGS. 8A-8D show connection of the linkages of FIGS. 6A-6B and 7A-7B together.

FIGS. 9A-9E show another exemplary embodiment of a dynamically rigidizing overtube.

FIGS. 21A-21D show a mother-daughter arrangement of a rigidizing overtube and a rigidizing scope.

FIGS. 33A-33D show another embodiment of a linkage of a dynamically rigidizing overtube.

FIGS. 41A-41D show exemplary embodiments of dynamically rigidizing overtubes with built-in working channels.

FIGS. 42A-42B show exemplary steering mechanisms for a dynamically rigidizing overtube.

FIGS. 43-47 show exemplary layered walls of a dynamically rigidizing overtube.

FIGS. 48A-48D show another exemplary handle for use with a dynamically rigidizing overtube.

FIGS. 55A-55E show another exemplary dynamically rigidizing system that includes extendable locking pivots.

DETAILED DESCRIPTION

Figure 1C:
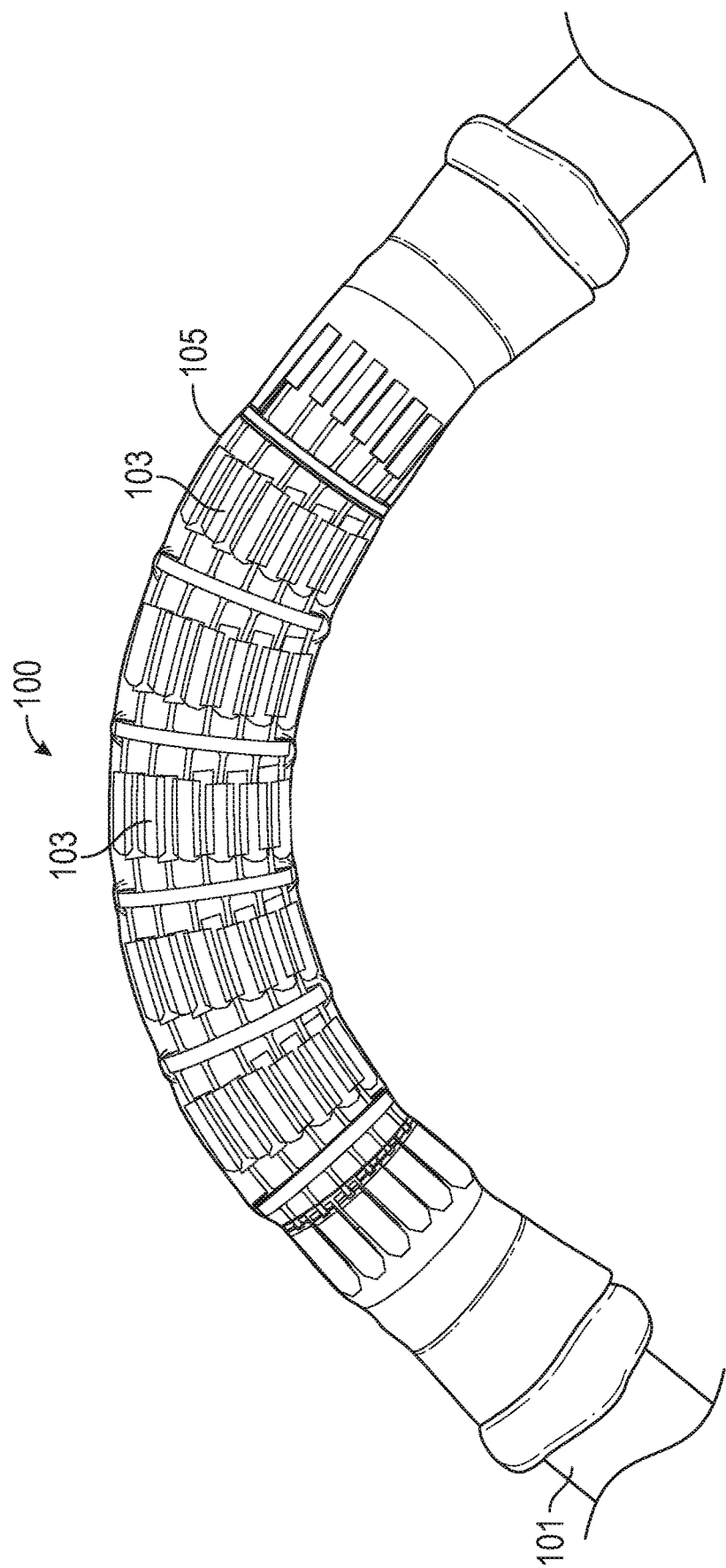
Figure 1D:
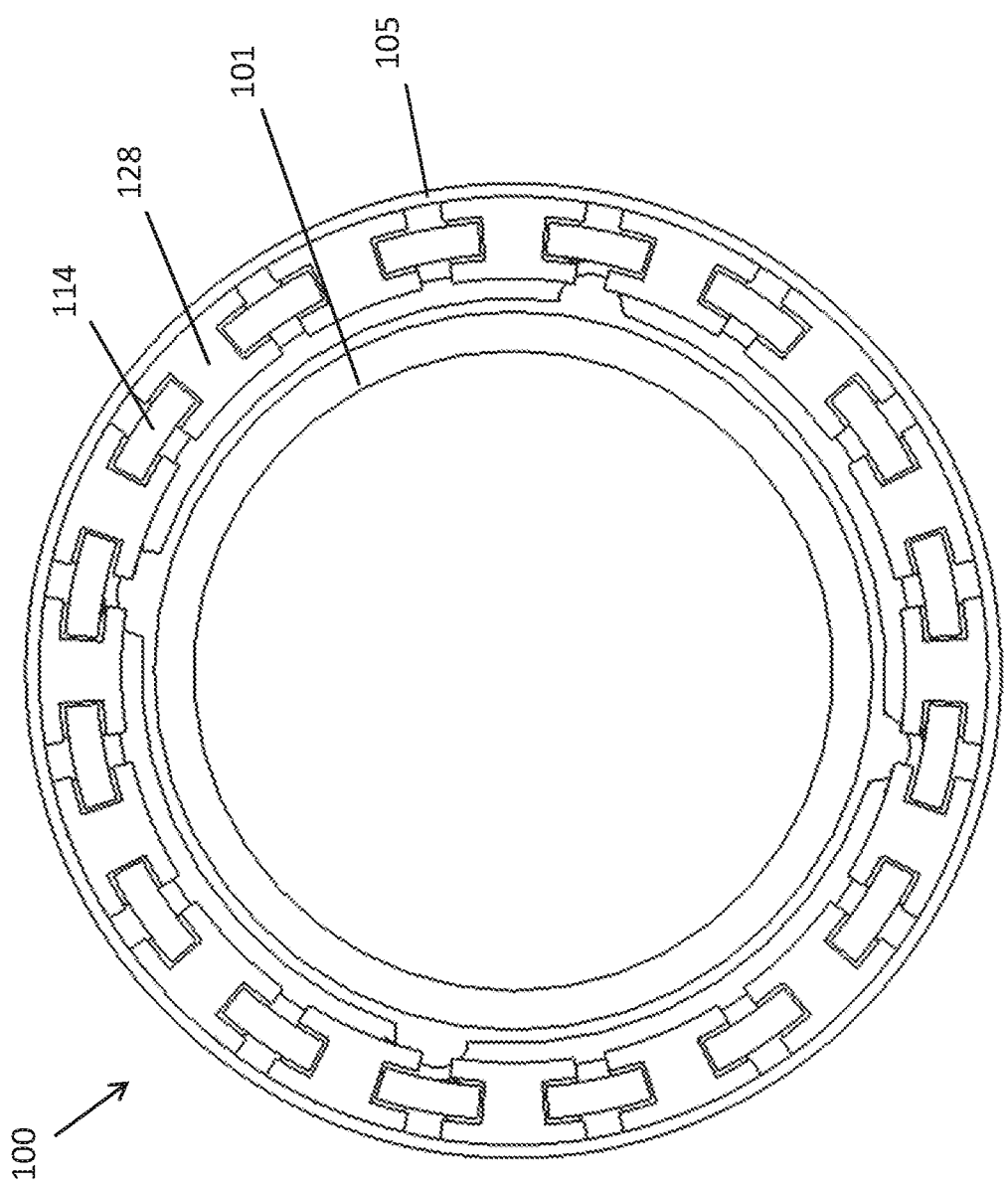

In general, described herein are overtubes that are configured to aid in transporting an endoscope through a curved or looped vessel. In general, the overtubes described herein are long, thin, and hollow and can transition quickly from a flexible configuration (i.e., one that is relaxed, limp, floppy) to a rigid configuration (i.e., one that is stiff). The overtubes can transition from the flexible configuration to the rigid configuration, for example, by applying a vacuum to the overtube.

The overtubes described herein provide rigidization for devices, including catheters, sheaths, endoscopes, laparoscopic instruments or robotic surgical equipment. The overtubes can function as a separate add-on device or can be integrated into the body of the catheters, sheaths, endoscopes laparoscopic instruments or robotic surgical equipment.

The stiffness of the overtubes described herein can increase from 2 fold to over 30 fold, for instance 10-fold, or 20-fold, when transitioned from the flexible configuration to the rigid configuration Referring to FIGS. 1A-1D, in one embodiment, an overtube 100 can be connected to a vacuum pump 110. Further, the overtube 100 can include an inner tube 101 having a plurality of interconnectable links 103 extending thereover. The links 103 can include a series of female engagers 128 and a series of male engagers 114 configured to engage with one another. Further, the links 103 can each include a mounting ring 122 from which the engagers 128, 114 extend. The mounting ring 122 can be bonded or fixed to the inner tube 101, which can in turn fix the ends of the engagers 128, 114 that are attached to the mounting ring 122 relative to the inner tube. The ends of the engagers 128, 114 not bonded to the ring 122 (i.e., the free ends of the engagers 128, 114) can remain free to move axially relative to one another as the inner tube 101 bends. An outer layer 105 can be sealed over the top of the overtube 100. The outer layer 105 can provide a sealed area around the links 103. When the vacuum pump 110 is activated, vacuum is created between the outer layer 105 and the inner tube 101, thereby transitioning from a flexible configuration to a rigid configuration, as further described below.

Figure 2A:
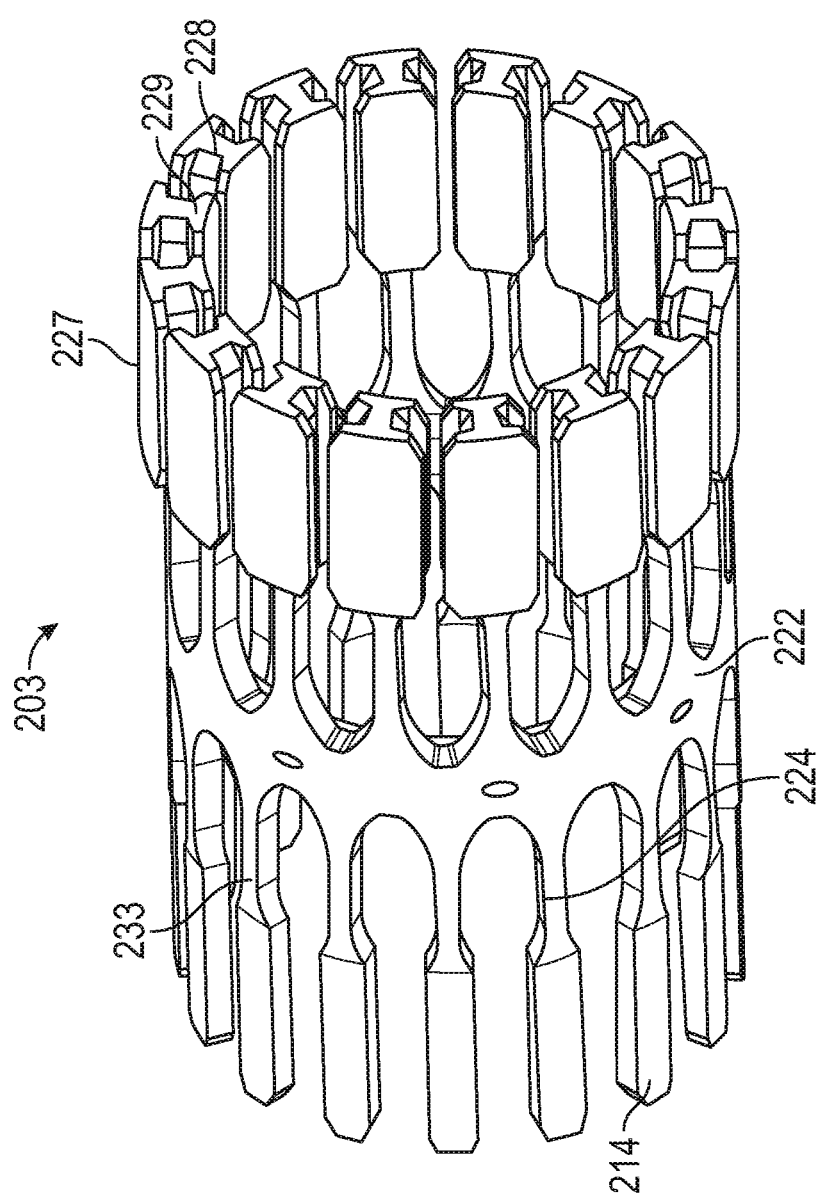
FIGS. 2A-C show an exemplary embodiment of a linkage of a dynamically rigidizing overtube.
Figure 2B:
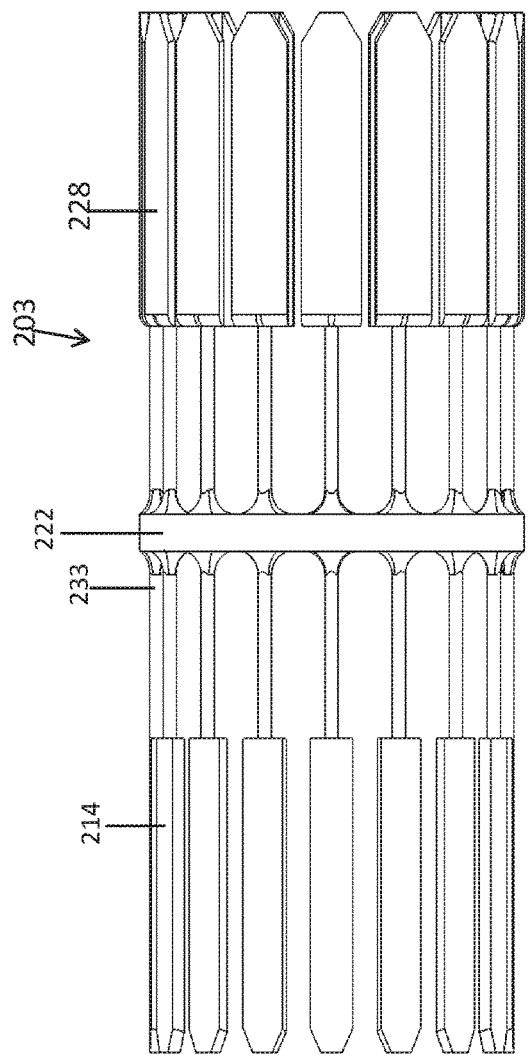
Figure 2C:
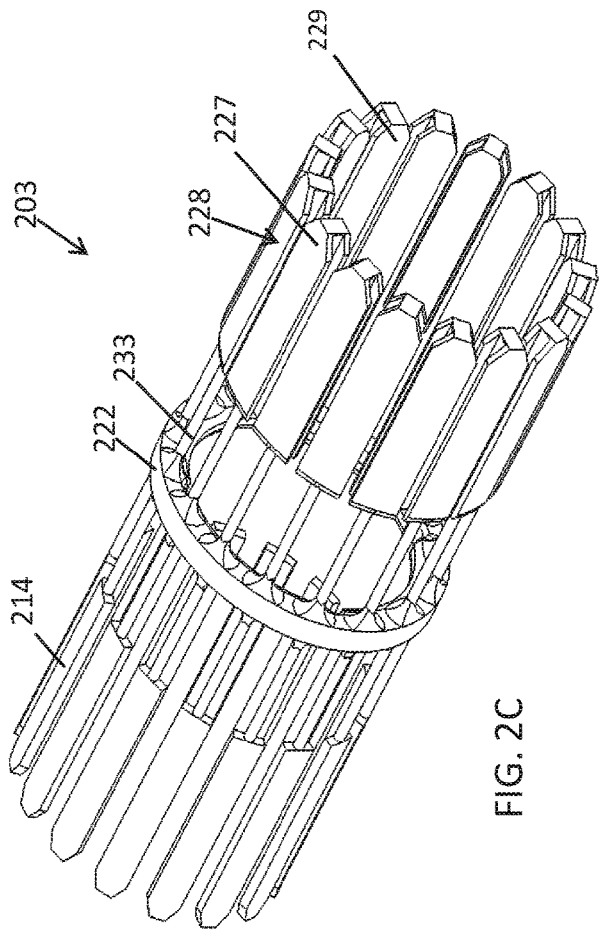

An exemplary embodiment of a link 203 (which can be used as link 103) is shown in FIGS. 2A-2C. The link 203 includes a mounting ring 222 having male engagers 214 and female engagers 228 extending therefrom. The male engagers 214 can be, for example, narrow and thin extensions from the mounting ring 222. The female engagers 228 each include an outer flange 227 and inner flange 229 configured to fit a male engager 214 therebetween. There can be a plurality of female engagers 228 and male engagers 214 positioned around the circumference of the link 203 and extending from each mounting ring 222. In some embodiments, there are between 10 and 20 engagers 214, 228, e.g., 16 engagers 214, 228 extending around the circumference of the link 203. Further, each male engager 214 and female engager 228 can be attached to the mounting ring 222 through a pivot mechanism 233, e.g., a narrow piece of material that provides for flexibility of the engagers 214, 228 relative to the ring 222. The pivot mechanism 233 can allow for pivoting at angles of up to 30 degrees, such as 5-20 degrees, such as approximately 10 degrees. In some embodiments, each link 203 can be from a single piece of material, such as a molded polymer.

Figure 3C:
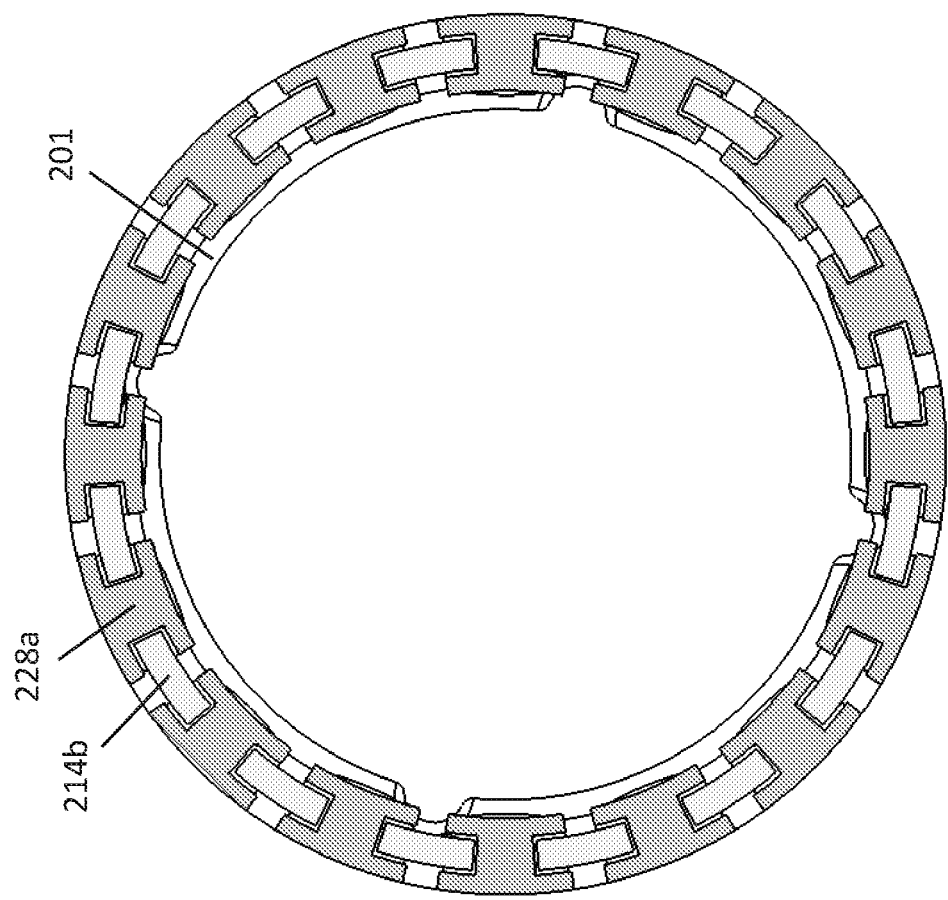

Referring to FIGS. 3A-3C, the links 203*a,b* can be configured to engage with one another. That is, the male engagers 214 and female engagers 228 can be arranged in an alternating pattern around the circumference of the overtube such that each male engager 214 is held in place by two neighboring female engagers 228. Further, the male engager 214 can move axially within the female engager 228. As the inner tube bends along the longitudinal axis, the pivot mechanisms 233 can provide pivoting of the male and female engagers 214, 228. Simultaneously, the male and female engagers 214, 228 can move axially with respect to one another to follow the bend of the inner tube 201.

Figure 4A:
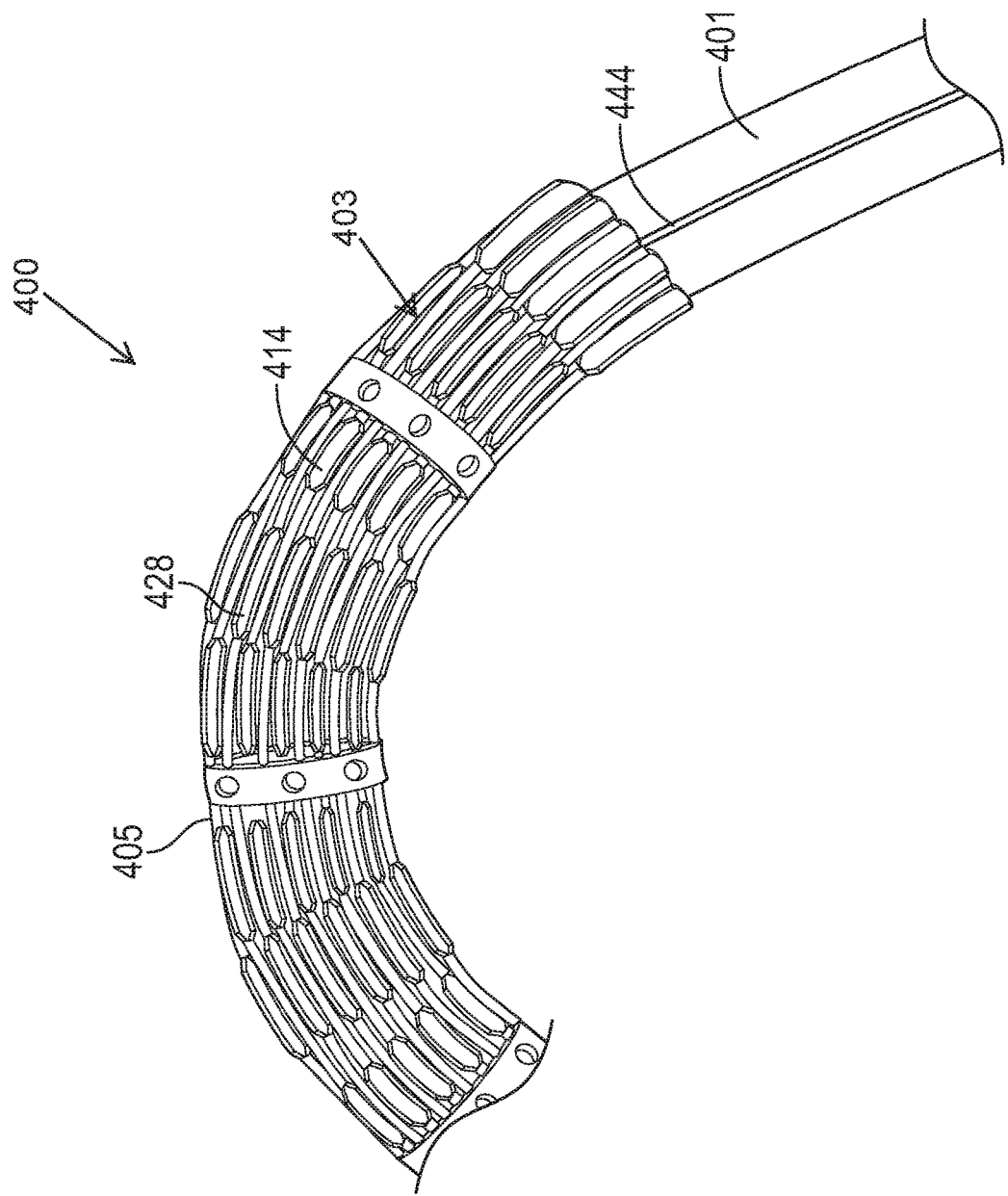
FIGS. 4A-4B show bending of a dynamically rigidizing overtube.
Figure 4B:
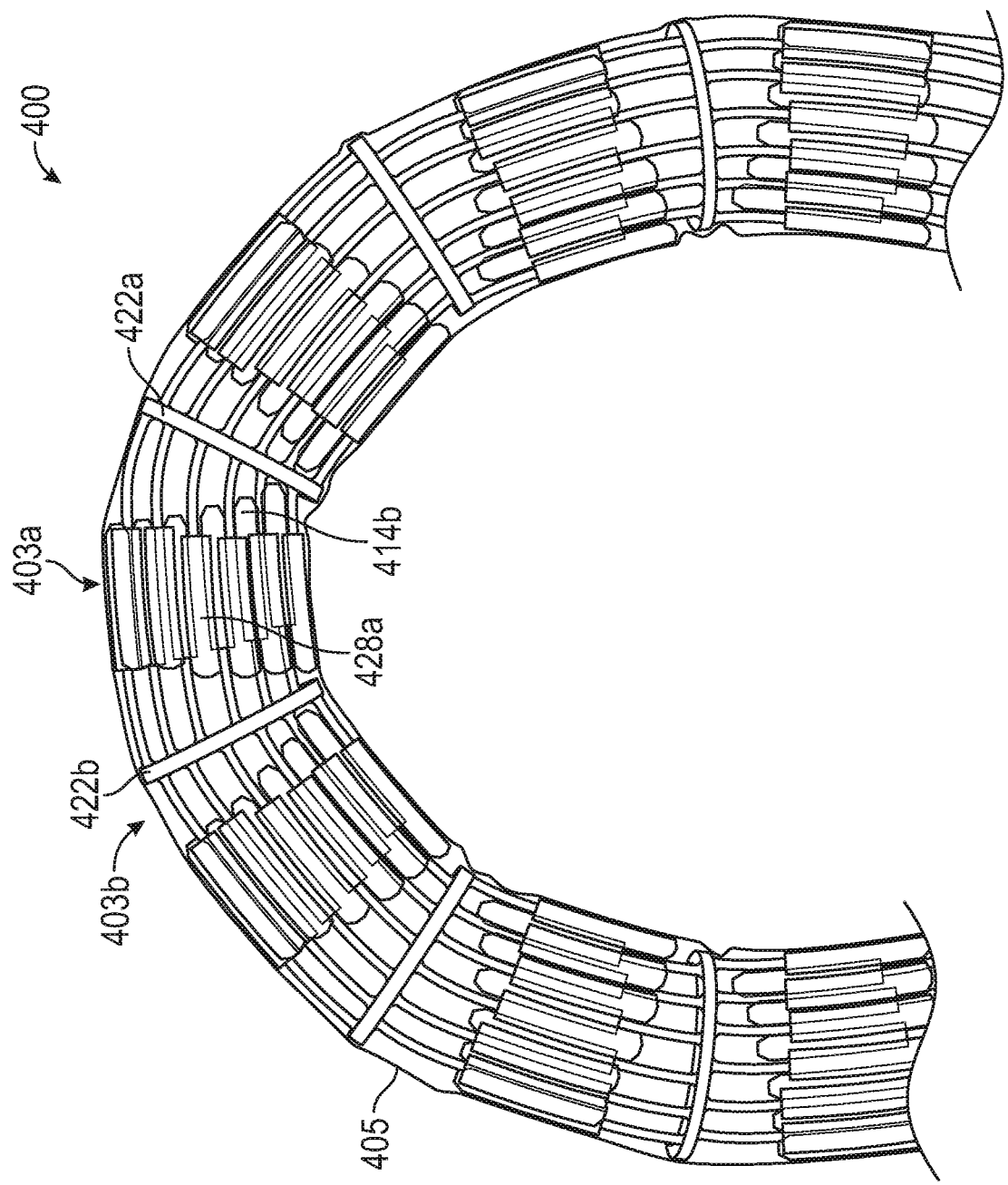

As shown in FIGS. 4A-4B, when the inner tube 401 bends, the free ends of the male engagers 414 that are positioned on the outside of the curved portion can move further axially out of the associated female engagers 428 while the free ends of the male engagers 414 that are on the inside of the curved portion can move further axially into the associate female engagers 428, thereby allowing the links 403a,b to follow the bend (or radius of curvature) of the inner tube 401. Thus, the unengaged length of each engager 428, 414 (i.e., the length of each engager that does not engage or mate with neighboring engagers) dynamically varies as the inner tube 401 bends (from a neutral set position when the tube is straight to a longer length when the engagers are on the outer axis as the tube is bent and a shorter length when the engagers are on the inner axis as the tube is bent). Further, the outer and inner flanges of the female engagers 428 advantageously extend circumferentially over at least a portion of the male engagers 414 so as to prevent the free ends of the male engagers 414 from popping out of the female engagers 428, thereby helping to keep the engagers 414, 428 substantially radially flush with the inner tube 401 (i.e., the engagers 414, 428 stay substantially in-plane as the inner tube 401 bends). Further, the pivots can advantageously supply high axial stiffness in both tension and compression, and resist shear loads, while simultaneously offering low bending force. The engagers 414, 428 can substantially conform to the bends of the inner tube 401.

As is further shown in FIGS. 4A-4B, the outer layer 405 can be sealed over the chain of links 403. A vacuum input line 444 can extend from the layer 405. When a vacuum is pulled under the layer 405, the layer 405 can be suctioned down or constricted over the connected links 403, causing the links 403 to radially constrict to become fixed or locked in place relative to one another. As a result, the overtube 400 can go from a flexible configuration to a rigid configuration when vacuum is pulled (thereby fixing the overtube in the configuration that the overtube was in just prior to application of the vacuum). As it is rigidized, it does so in the shape it was in before vacuum was applied, i.e., it does not straighten, bend, or otherwise substantially modify its shape. Upon release of the vacuum, the links 403 can unlock relative to one another and again move so as to allow bending of the overtube 400. Again, as it is made more flexible through the release of vacuum, it does so in the shape it was in before the vacuum was release, i.e., it does not straighten, bend, or otherwise substantially modify its shape. Thus, the overtube 400 (and any overtube described herein) can transition from a flexible, less-stiff configuration to a rigid configuration of higher stiffness by increasing friction between the links (e.g., by applying vacuum). In some embodiments, the space between the layer 405 and inner tube 401 and/or links 403 is filled with a gas in the flexible configuration, and the gas is removed in the rigid configuration.

Figure 5A:
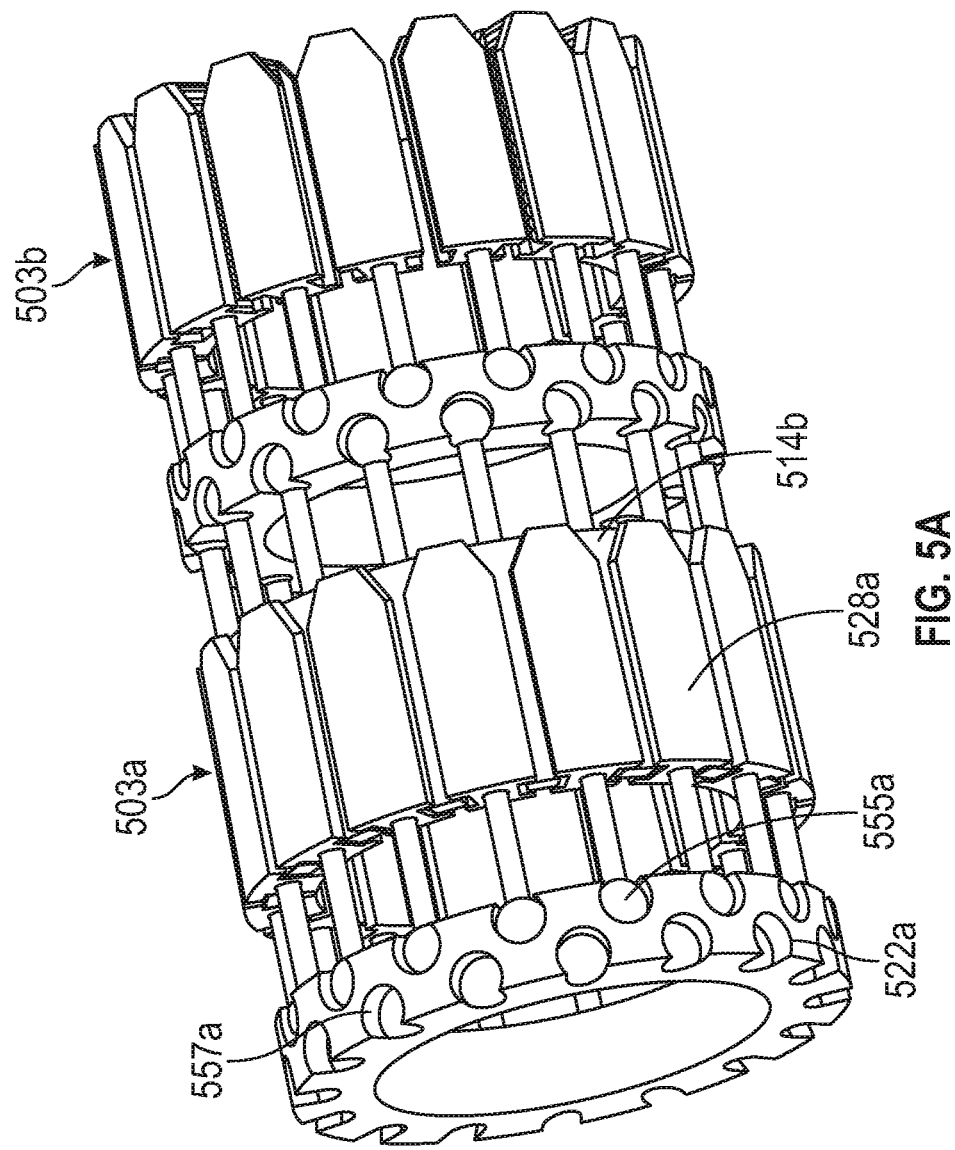
Figure 5B:
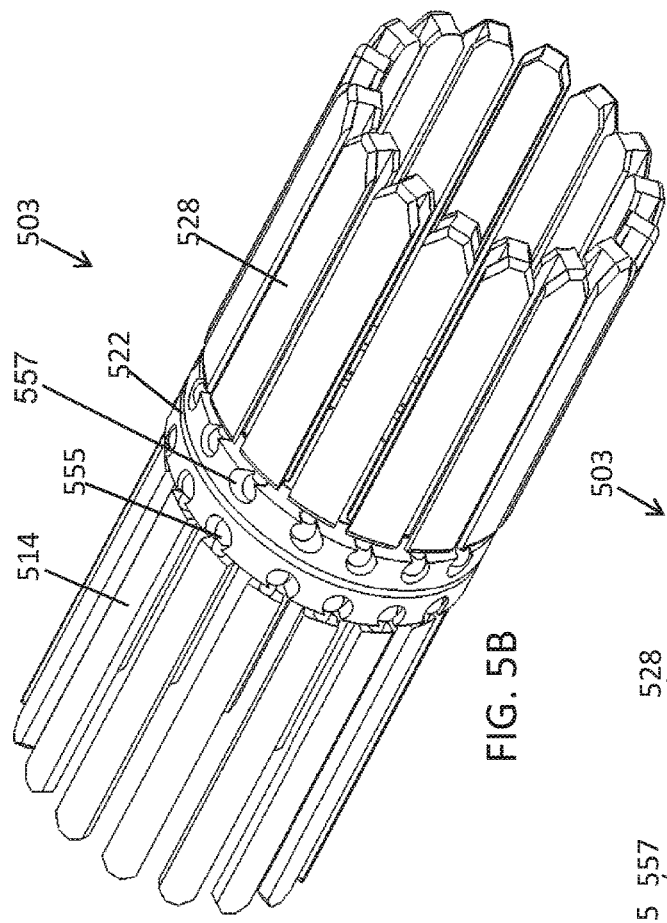
Figure 5C:
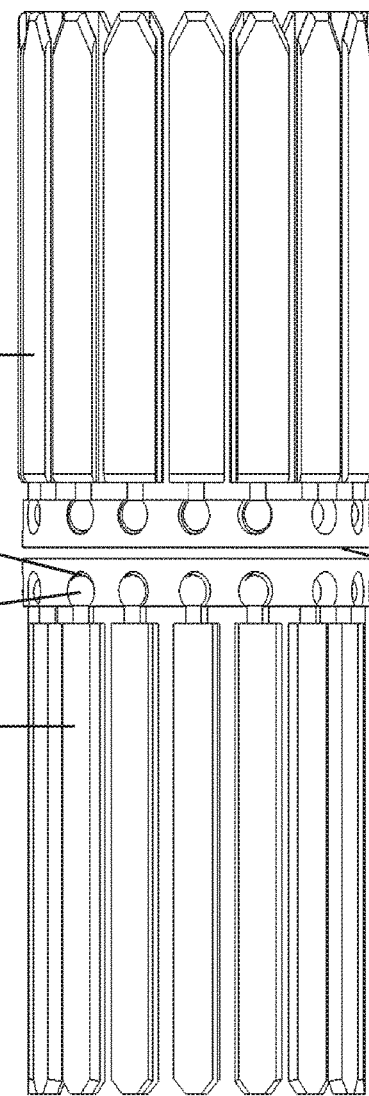
Figure 8C:
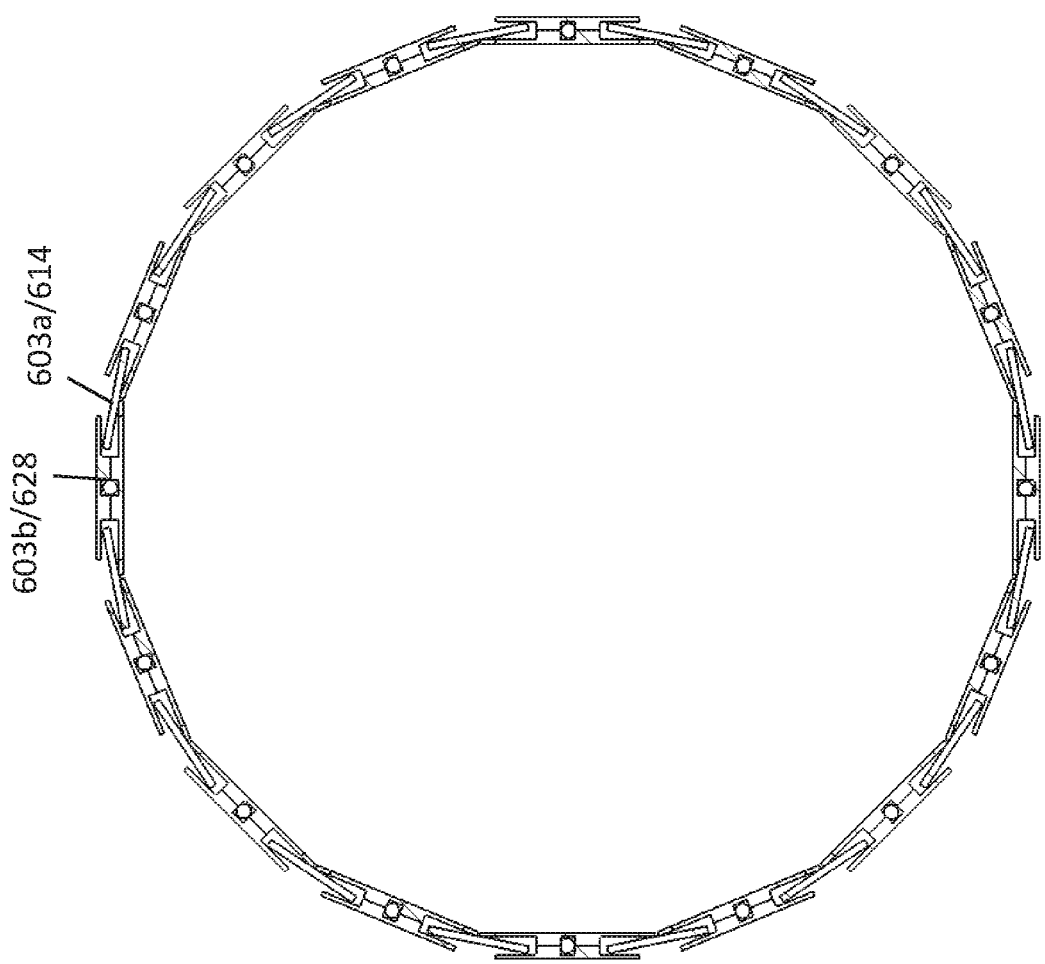
Figure 9E:
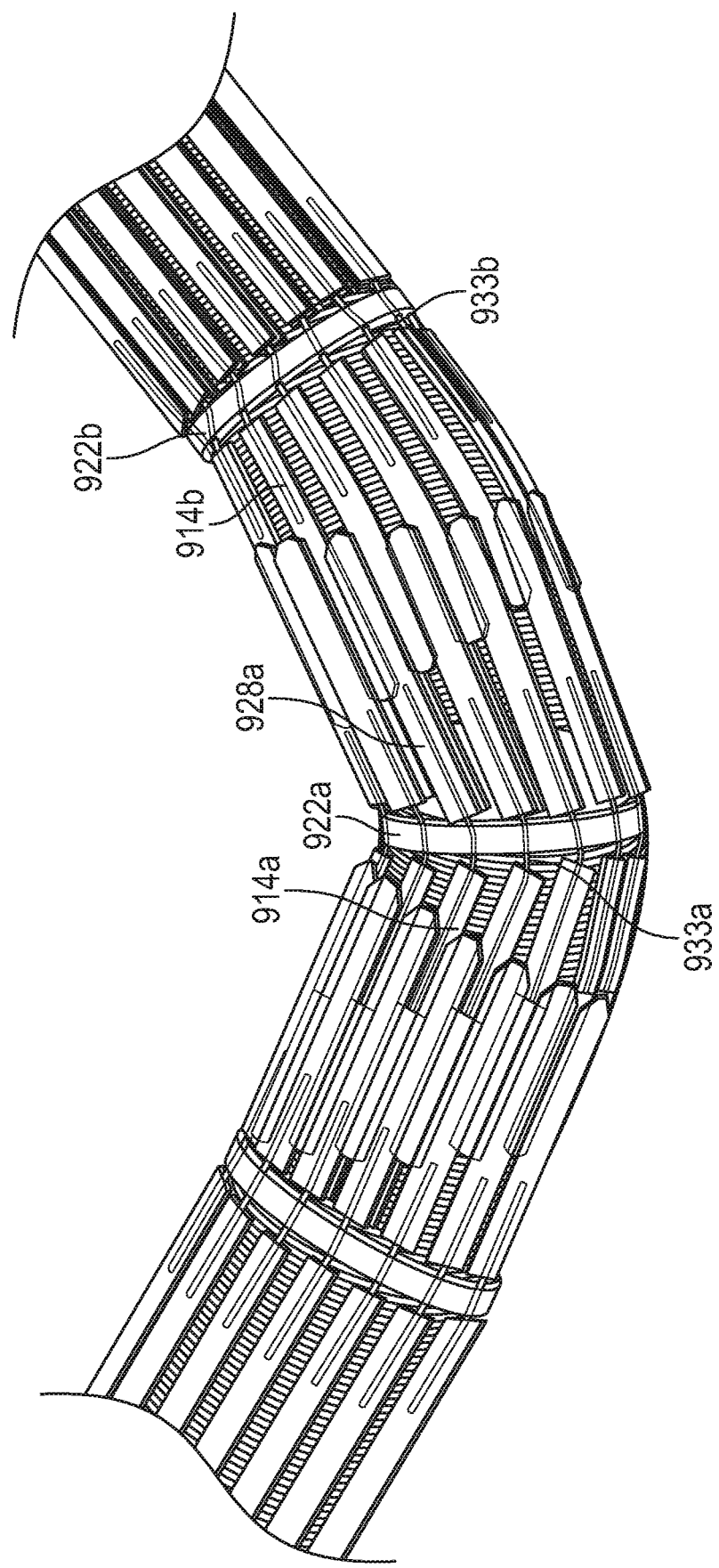

Another embodiment of a link 503 (or links 503a,b) for use with any of the overtubes described herein is shown in FIGS. 5A-5E. The link 503 is similar to link 203 except that it includes a ball and socket joint mechanism. That is, each link 503 includes a mounting ring 522 having a plurality of sockets 557 extending circumferentially therearound. The female engagers 528 and male engagers 514 each include balls 555 on the end thereof configured to fit and pivot within the respective socket 557. As shown in FIGS. 5D-5E, the mounting ring 522 can include a protective sealing ring 559 thereover to hold each of the balls 555 within the sockets 557. In some embodiments, the link 503 can be made of a molded polymer.

Another embodiment of links 603a, 603b are shown in FIGS. 6A-8D. In this embodiment, link 603a includes mounting ring 622 with a plurality of male engagers 614 extending from either end. Link 603b includes mounting ring 622 with a plurality of female engagers 628 extending from either end. Thus, rather than including both male and female engagers, the link 603a (or only link described herein) can include only male engagers 614 while the neighboring link 603b can include female engagers 628 configured to engage therewith. In some embodiments, the engagers 614, 628 can be made of a metal sheet. Further, a wire pivot 633 can connect the engagers 614, 628 to the ring 622. This wire pivot 633 advantageously enables high tensile stiffness. The length of the wire pivot 633 can be short (for example, 0.25 mm, 0.5 mm, 1 mm, 1.5 mm), allowing it to exhibit high compression and tensile stiffness and high resistance to shear loads while also providing the requisite low bending force that enables the overtube to deliver a low baseline bending stiffness/high flexibility. Exemplary wire pivots include a 0.008" diameter s.s. cable, 0.012" diameter s.s. wire, 0.025" diameter plastic, or 0.006" nitinol wire.

Another embodiment of a link 903 is shown in FIGS. 9A-9E. In this embodiment, the link includes a mounting ring 922 with wire pivots 933 extending therefrom. Male and female engagers 914, 928, respectively, are molded over the wire pivot 933 while leaving some of the wire pivot 933 exposed near each mounting ring 922. For high stiffness, thin walls, and high mold flow, LCP (liquid crystal polymer) can be used for the engagers 914, 928, which can be overmolded onto the pivots 933 (e.g., the cables of the pivots). The engagers 914, 928 can also be made of other plastics of high modulus such as mineral filled grades, PEEK, or ultem. Frictionally enhancing materials can also be used to preferentially lock mating engagers, with frictional coefficients of 0.6, 0.8, 1, or greater.

Figure 33D:
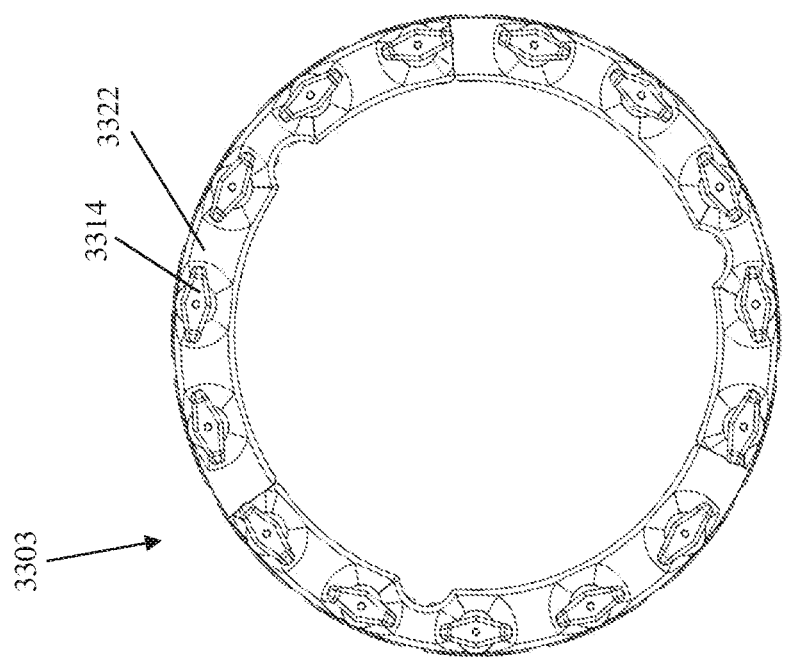
Figure 33C:
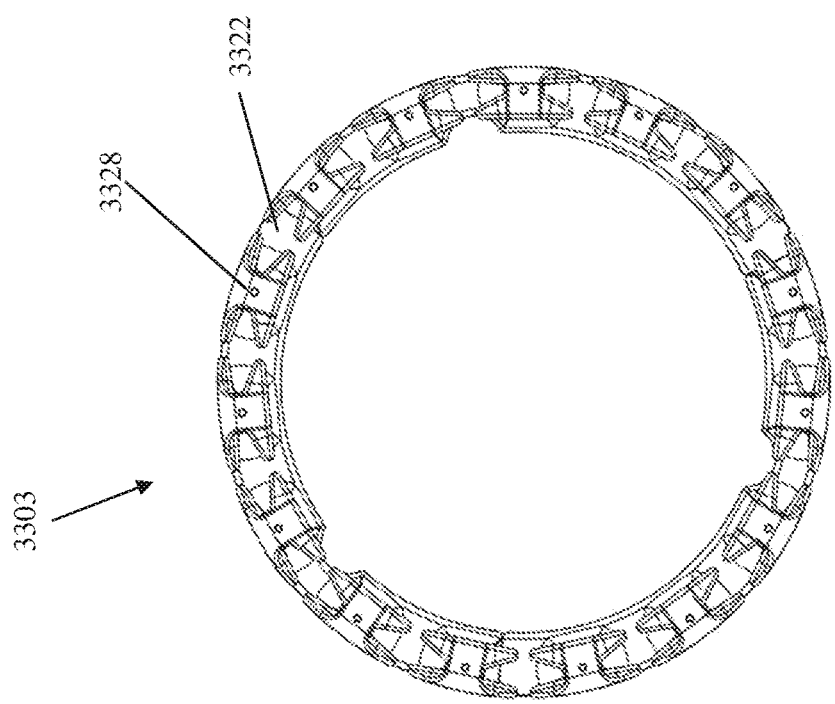

Another embodiment of a link 3303 is shown in FIGS. 33A-35C. As shown in FIGS. 33A-33B, the link 3303 includes a mounting ring 3322 from which a series of male engagers 3314 and female engagers 3328 extend. The mounting ring 3322 can be made, for example, of a material such as polycarbonate, Rezilient, or Ixef. The engagers 3314, 3328 can be connected to the ring 3322 by wire pivots 3333. The wire pivots 3333 can be, for example, wire cable with a diameter of 0.005" to 0.010", such as 0.008". Further, extensions 3334, 3338 can extend from the ring 3322 to the wire pivots 3333. The length of exposed pivot 3333 can be 0.005"-0.015", such as approximately 0.010". Further, the extensions 3334, 3338 can advantageously help move the pivots 3333 away from the ring 3322, which can reduce faceting and reduce the tendency of the of the engagers 3314, 3328 to bottom out on the neighboring ring. The extensions 3334, 3338 can be longer on one side of the ring 6222 on the other. Having the extensions longer on one side than the other further reduces the tendency of the engagers 3314, 3328 to bottom out on the neighboring ring. For example, the extensions 3338 on the female side can be longer than the extensions 3334 on the male side. Any of the extensions 3334, 3338 (such as the longer extensions 3338) can be tapered from the ring 3322 towards the wire pivots 3333 (e.g., tapered at 1-8 degrees, such as 4 degrees). Further, the extensions 3334, 3338 can be configured to flex a pre-determined amount, to aid in pivoting of the engagers 3314, 3328 and bending of the device while still being stiff enough to resist buckling.

Figure 34A:
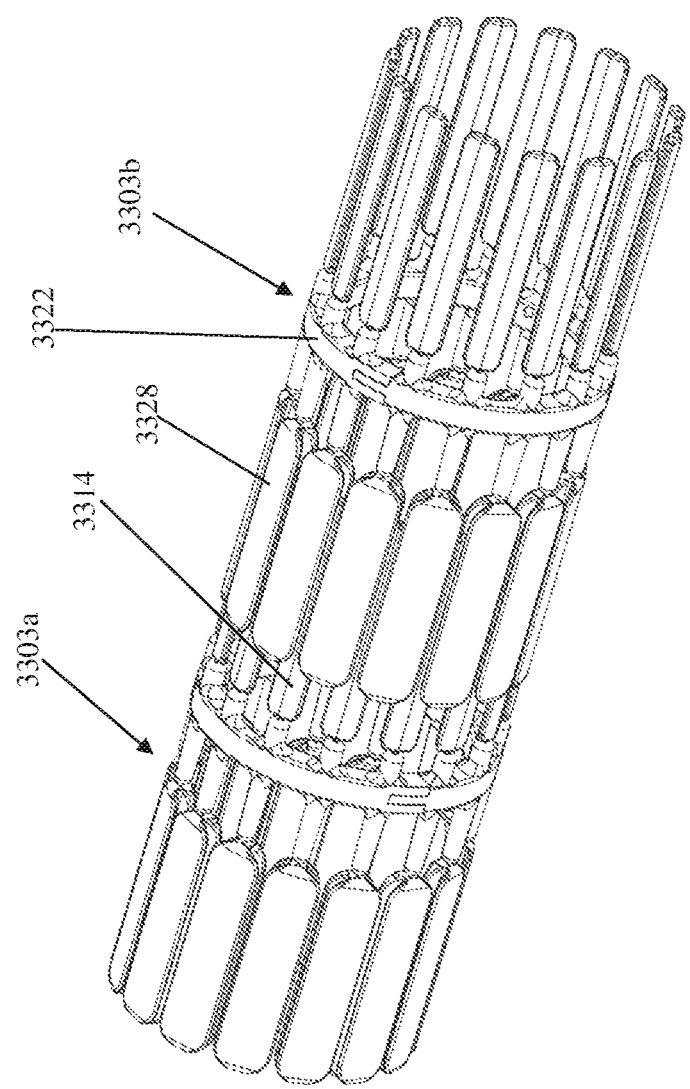
FIGS. 34A-34C show two linkages similar to those shown in FIGS. 33A-33D engaged with one another.
Figure 34B:
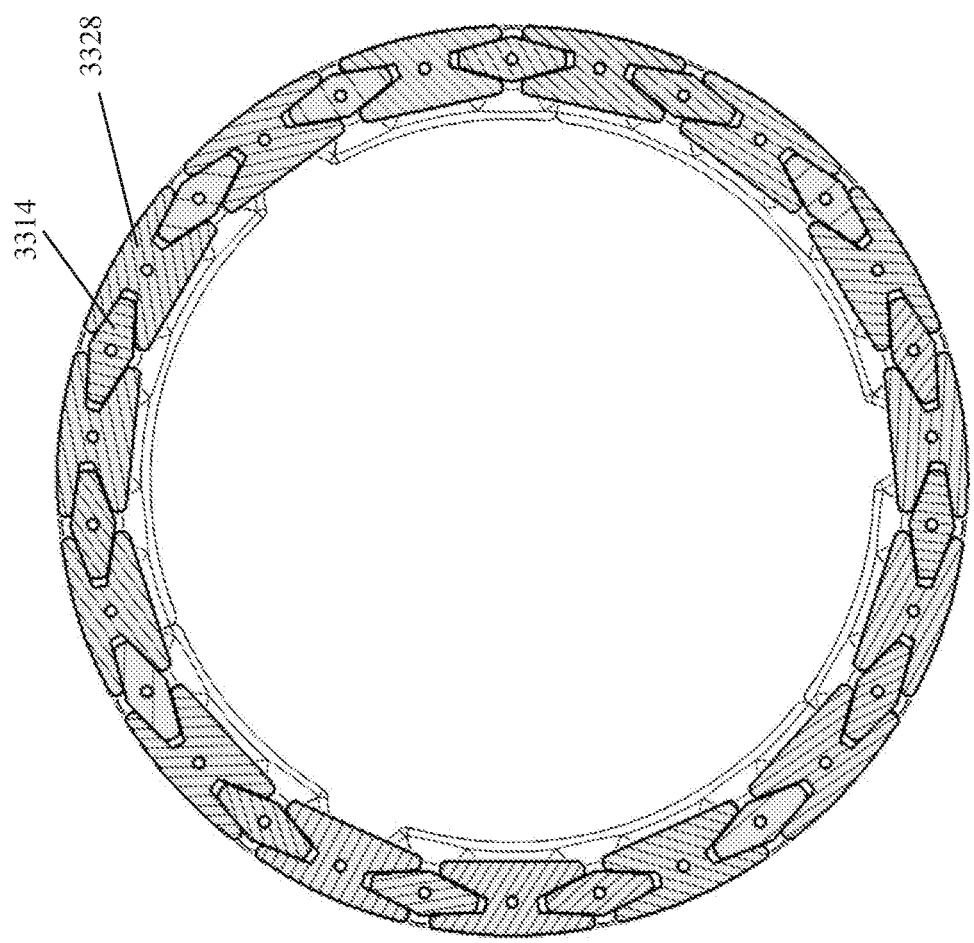
Figure 34C:
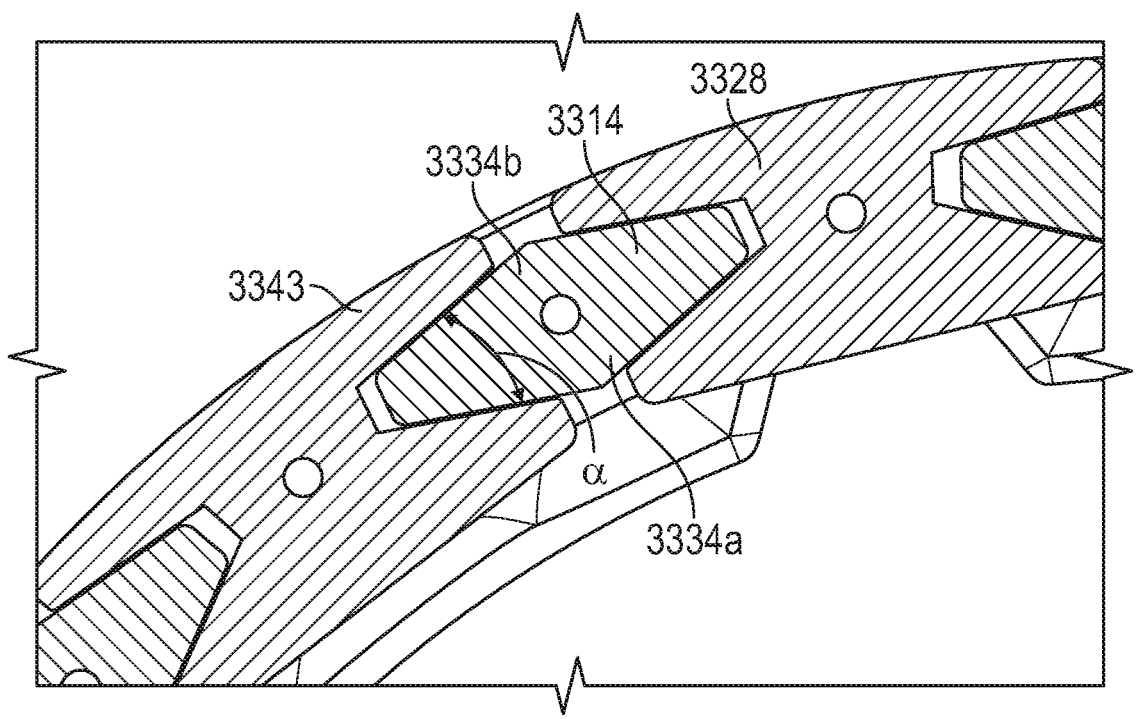

Referring to FIGS. 34A-34E, the male engagers 3314 of one link 3303a can engage with the female engagers 3328 of the neighboring link 3303b. The pitch of the links (i.e., between neighboring rings 3322) can be 0.5"-1.5", such as approximately 1". Further, the male engagers 3314 can be tapered on either side to as to form double-sided wedges. As shown in FIG. 34C, each wedge can form an angle α of 10°-40°, such as 25°-35°, such as approximately 30°. In some embodiments, the inner surface 3334a and outer surface 3334b of the male engager 3314 can be symmetric while in other embodiments, the two surfaces 3334a,b can be asymmetric. The female engagers 3328 can be shaped as I-beams, and each of the I-beam inner surfaces 3343 of the female engagers 3328 can be tapered (e.g., at 12.5°-17.5°, such as 15°) to match the taper of the male engagers 3314. Having the male and female engagers 3314, 3328 with tapers at the recited angle range can advantageously provide strong engagement between the engagers 3314, 3328 while allowing the engagers 3314, 3328 to slide relative to one another. That is, if the angle is too small, the engaged links 3303a,b may engage well, but may self-lock even when vacuum is removed and therefore not slide well. If the angle is too large or steep, then the links 3303a,b may slide well relative to one another, but may not engage well even under vacuum.

In a further embodiment, the female engager 3328 can have a single I-beam flange on the outermost flange with the inner-most surface being accomplished by the outside surface of the coil wound tube, and the male engager can be commensurately adapted to provide rigidization by being clamped against the coil wound tube instead of the inner I-beam flange.

Further, the engagers 3314, 3328 can have a maximum thickness, for example, of 0.04", such as 0.035" and a width of 0.5"-1.0", such as 0.8". The (E)(I) (elastic modulus times moment of inertia) defines a beam stiffness. The elastic modulus E can be between 200,000 psi and 600,000 psi, such as about 400,000 psi. An (E)(I) within this range for the engagers of the specified size can advantageously ensure that the engagers 3314, 3328 are flexible enough to allow deflection under vacuum to allow for alignment while being stiff enough to allow them to slide freely when not under vacuum.

Figure 35B:
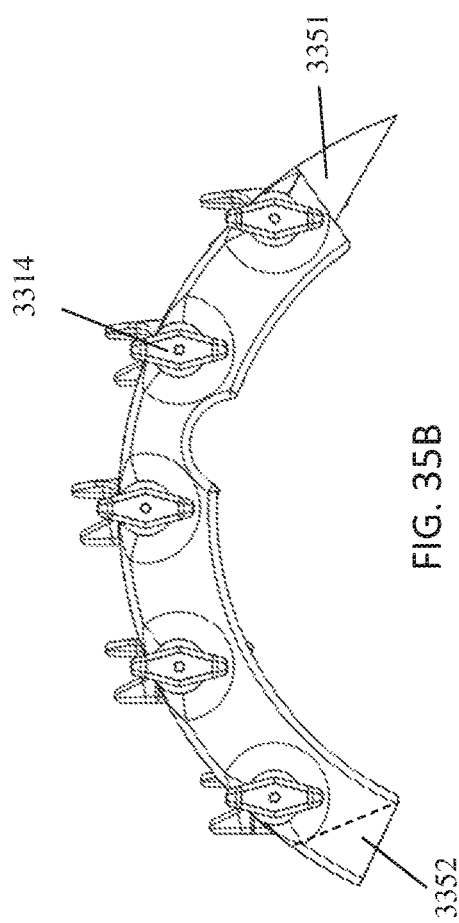
FIGS. 35A-35C show an exemplary method of manufacturing a linkage.
Figure 35C:
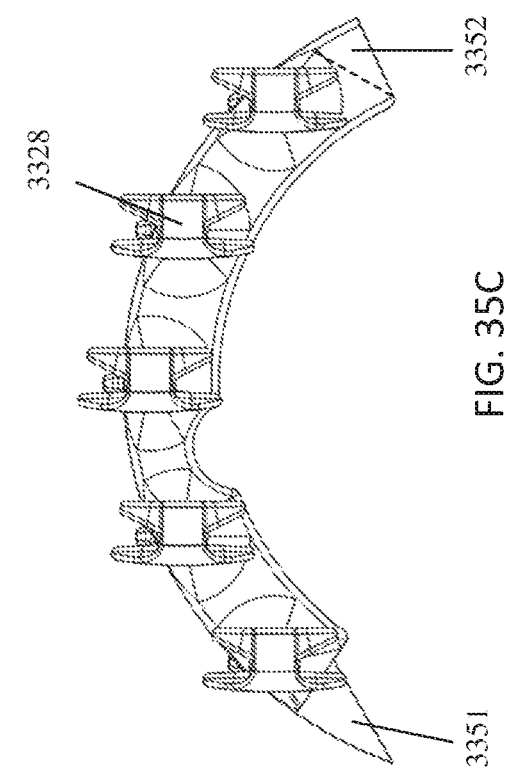
Figure 35A:
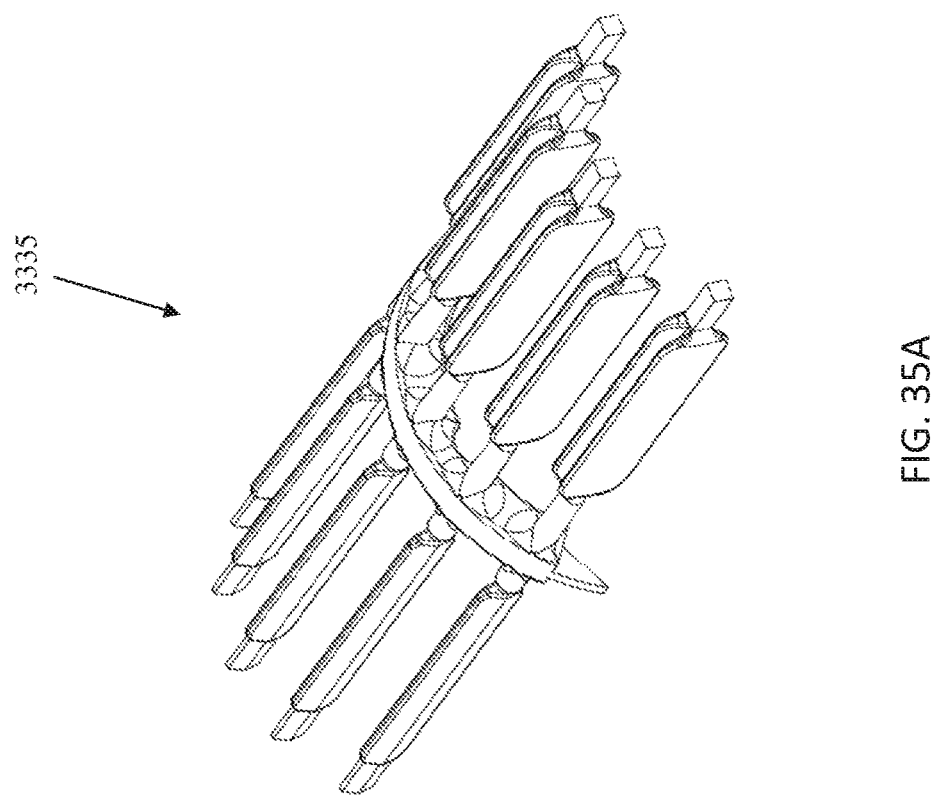

Referring to FIGS. 35A-35C, in some embodiments, the links 3303 can be manufactured by molding the links. For example, each link 3303 can be molded as three separate sections 3335 (e.g., each section extending 120° around the circumference of the entire link). Further, each engager 3314, 3328 can be aligned vertically during manufacturing to ease the molding process. Once molded, the engagers 3314, 3328 can be rotated (along the wire pivots) such that each inner surface is orthogonal to a line passing through the center of the link. Each section 3335 can be connected together (e.g., through a tongue 3351 and notch 3352 connection mechanism).

In some embodiments, the entire link 3303 can be molded from a single material. In other embodiments, the link 3303 can be dual-shot such that the ring 3322 can be made from a different material than the engagers 3314, 3328. There can be 12-18 male engagers 3314 extending circumferentially around each link, such as 14-16 engagers 3314, such as 15 engagers 3314. Similarly, there can be 12-18 female engagers 3328 extending circumferentially around each link, such as 14-16 engagers 3328, such as 15 engagers 3328. Having a number of engagers 3314, 3328 within the range ensures good shear performance while maintaining strong bending grip.

Figure 10:
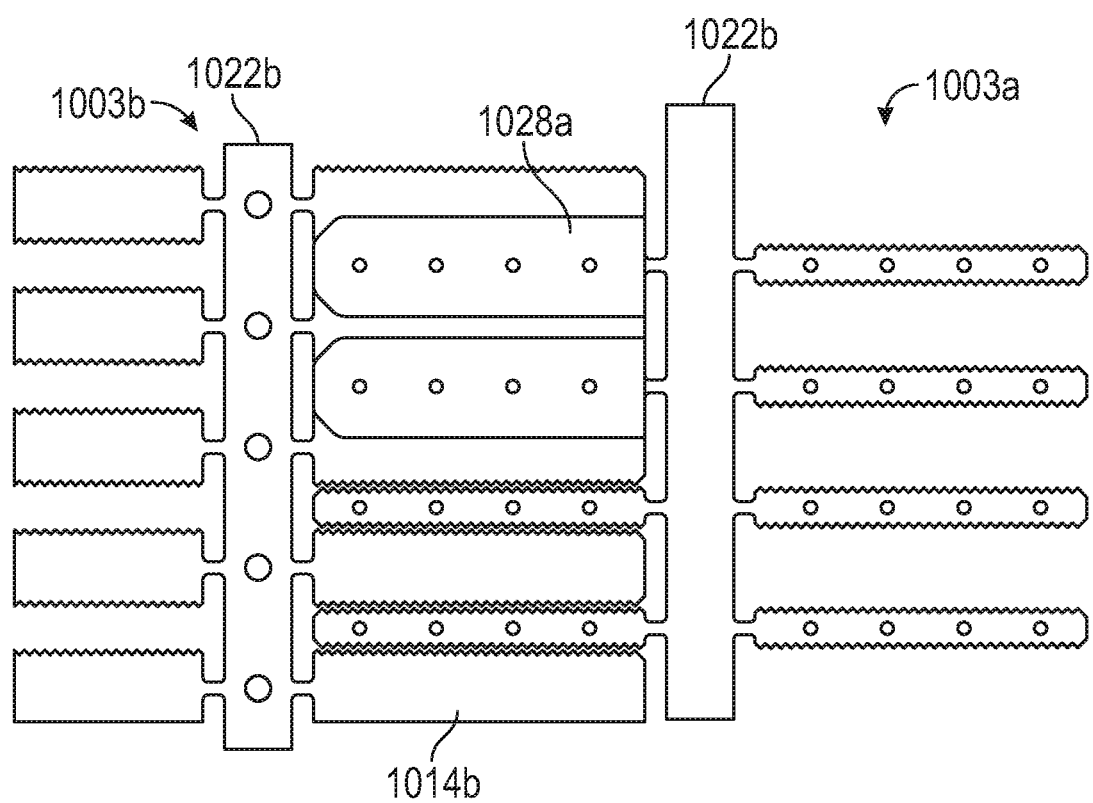
FIG. 10 shows another exemplary embodiment of linkages of a dynamically rigidizing overtube, in which serrated engagers are created from a sheet structure.

Another embodiment of engaged links 1003a,b is shown in FIG. 10. In this embodiment, a single link 1003a,b includes only male or female engagers 1014b, 1028a (though the link can be designed to include both male and female engagers as described elsewhere). As shown, the female engagers 1028 can include a plurality of serrations on an inner section thereof (the top and bottom flanges are shown removed on some engagers 1028 for clarity) that are configured to interlock with serrations on the male engagers 1014. In some embodiments, the links 1003a,b can be made out of a metal sheet. In other embodiments, the links 1003a,b can be laser cut, waterjet cut, stamped, EDM cut, or photochemically etched. Further, thickness of the links can be in the range of 0.004" to 0.010".

Figure 11:
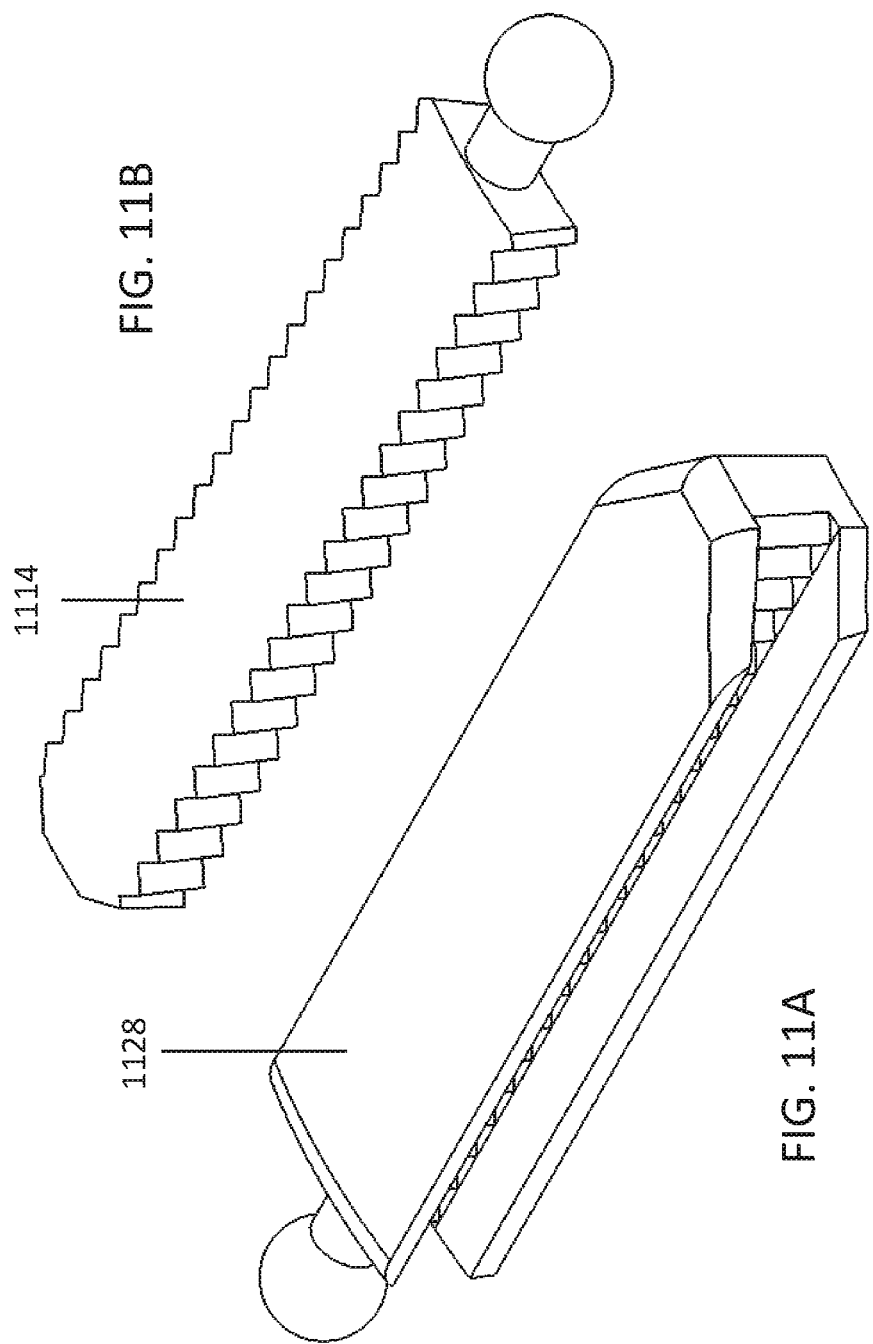
FIGS. 11A-11B show serrations on ball and socket engagers of a dynamically rigidizing overtube.
Figure 29D:
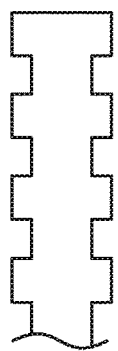
FIGS. 29A-29G show engagers with various serrations thereon.
Figure 29C:
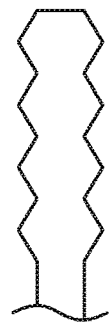
Figure 29B:
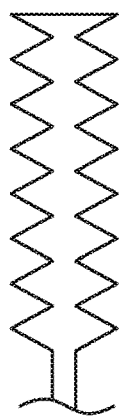
Figure 29A:
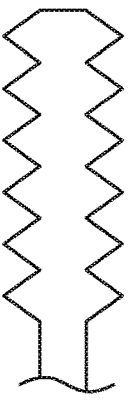
Figure 29G:
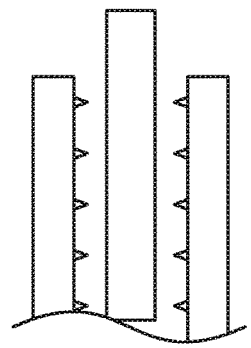
Figure 29F:
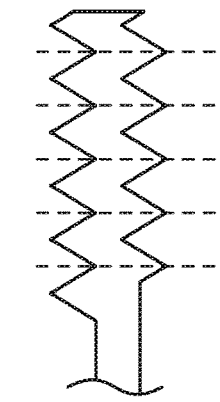
Figure 29E:
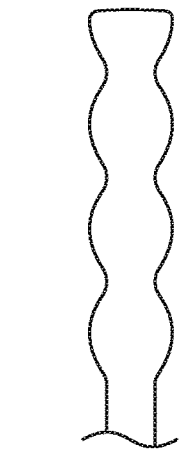

Similar serrated male and female engagers 1114, 1128 are shown in FIGS. 11A-11B, respectively. In this embodiment, the male and female engagers 1114, 1128 each include a ball joint that can be connected with sockets as described with respect to other embodiments above. Additionally, FIGS. 29A-29G show various embodiments of serrations (FIG. 29A shows serrations with an intermediate angle, FIG. 29B show serrations with a steep angle, FIG. 29C show serrations at a shallow angle, FIG. 29D shows orthogonal (shear) serrations, FIG. 29E shows curved or wavy serrations, FIG. 29F shows offset serrations, and FIG. 29G shows micro-embedded serrations for added friction).

Figure 12:
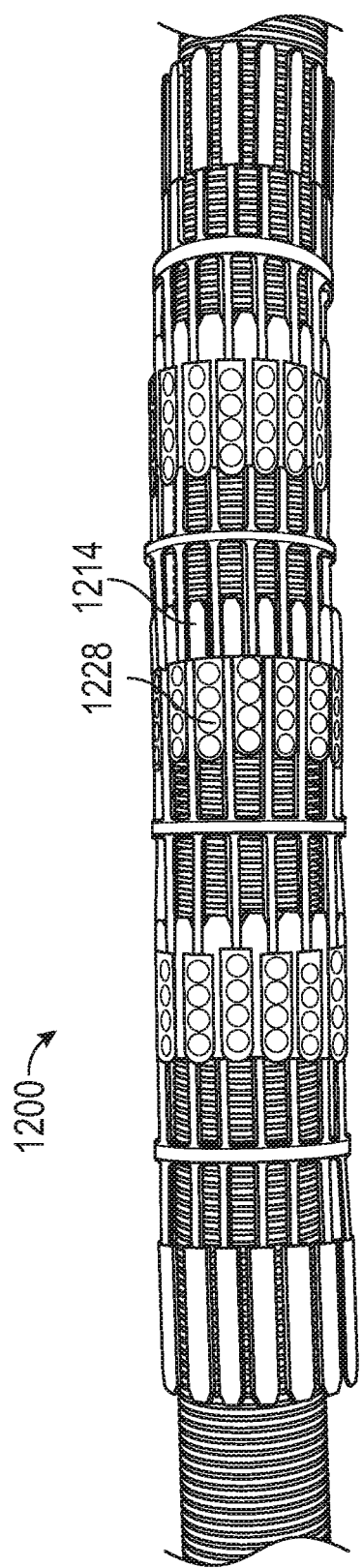
FIG. 12 shows another exemplary embodiment of a dynamically rigidizing overtube, in which I-beam caps are added to plastic I-beam structures.

Another embodiment of an overtube 1200 is shown in FIG. 12. In this embodiment, the links include plastic male engagers 1214 and female engagers 1228 that are a hybrid of both metal and plastic elements.

Figure 14:
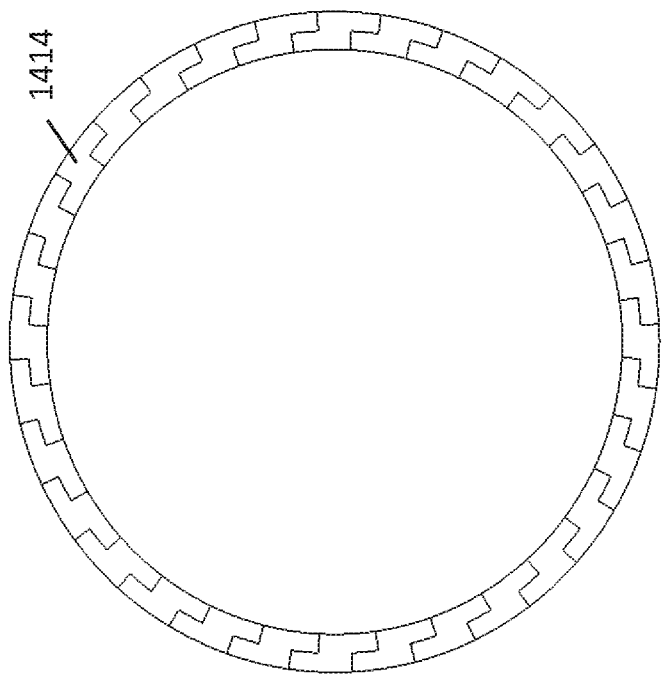
FIG. 14 shows exemplary embodiments of dynamically rigidizing overtubes including ledge-shaped geometries.
Figure 13:
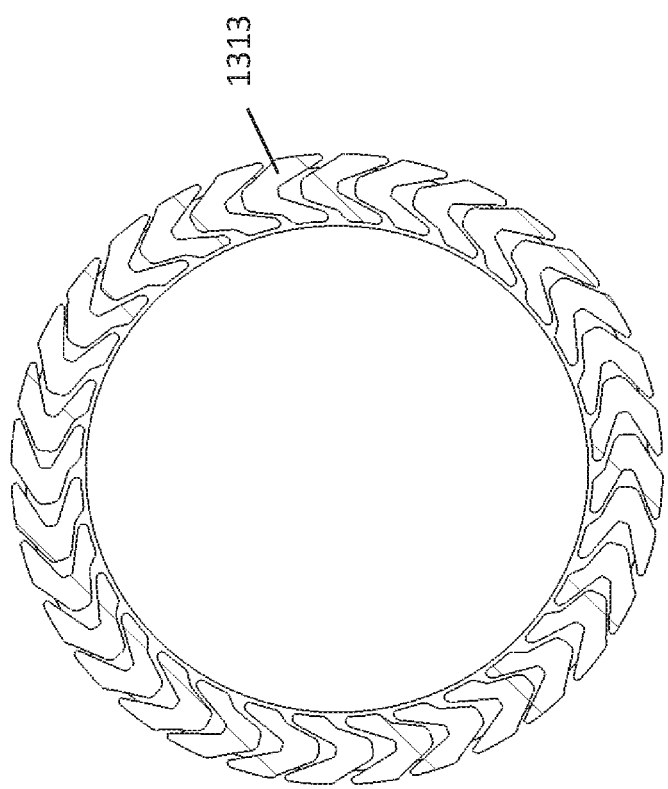
FIG. 13 show exemplary embodiments of dynamically rigidizing overtubes including interlocking wedges.

In some embodiments, rather than including separate male and female engagers, the links can include a plurality of the engagers, where each engager is substantially the same and includes a male portion on one side and a female portion on the other side such that neighboring male and female portions can interlock with one another. For example, FIG. 13 shows a plurality of wedge engagers 1313 that are movable axially relative to one another when not constrained, but lock relative to one another when constrained (e.g., by pulling vacuum). These wedges have mating angulated surfaces that are below the critical locking angles, such that they release when vacuum is released. Similarly, FIG. 14 shows a plurality of engagers 1414 shaped to lock relative to one another when constrained.

Figures 15A, 15B:
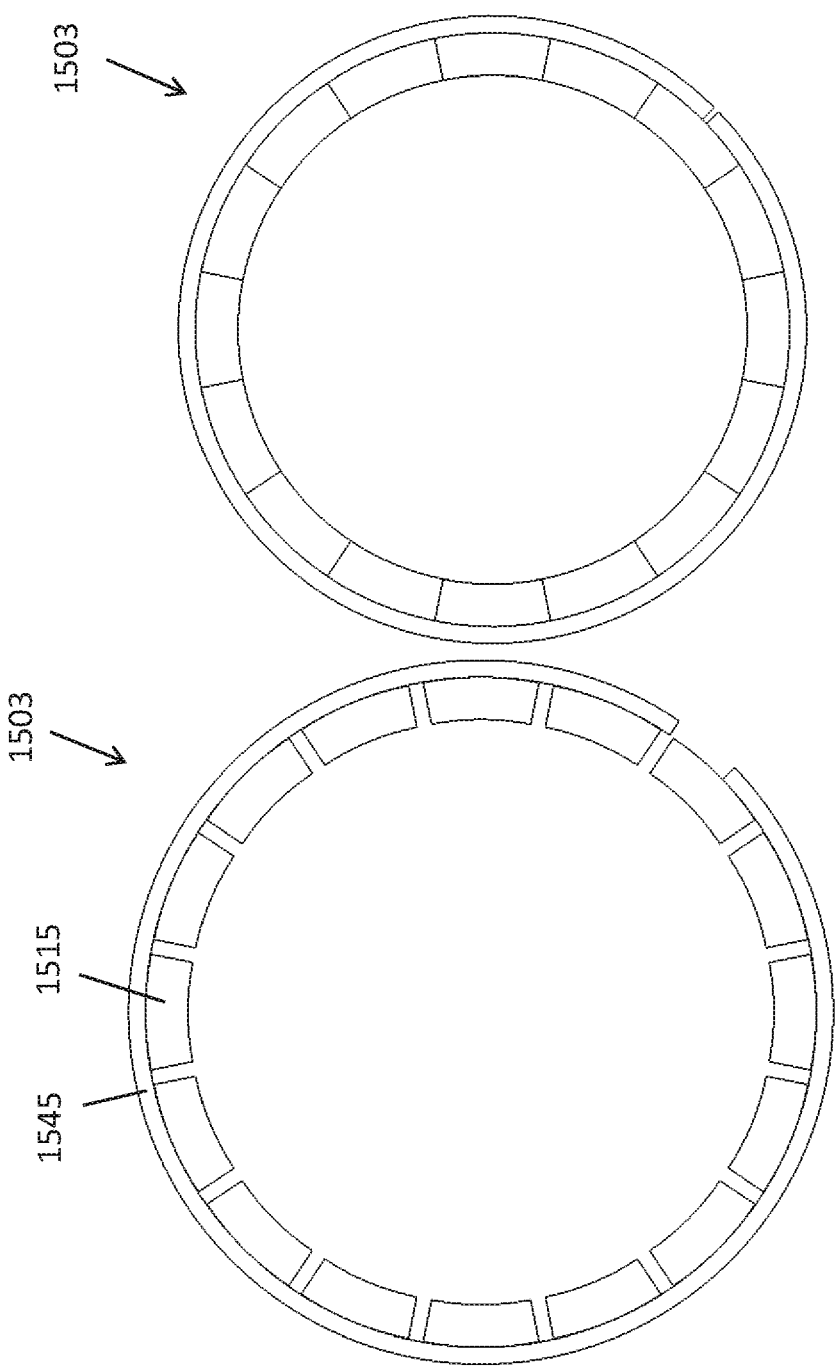
FIGS. 15A-15B show an exemplary embodiment of a dynamically rigidizing overtube including a split ring to hold the engagers in place.
Figure 16:
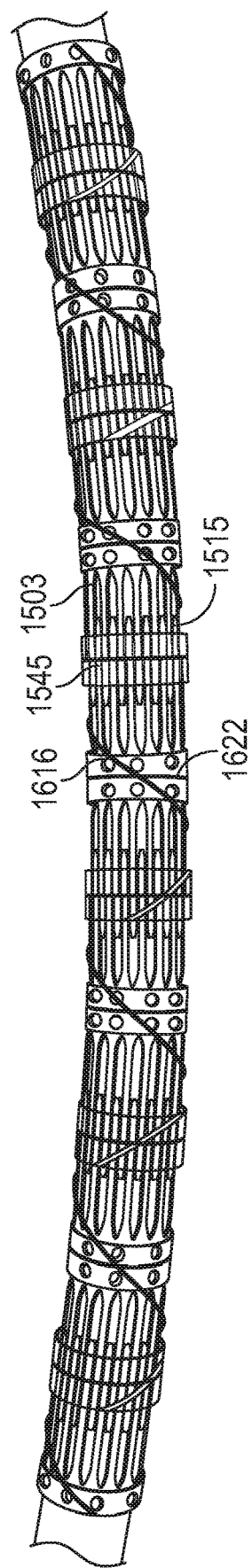
FIG. 16 shows a wire spiraled around the linkages of a rigidizing overtube to keep the split rings in position.
Figure 30:
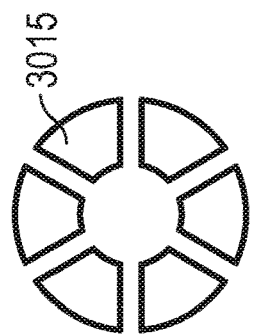
FIG. 30 shows engagers shaped as keystones.

Referring to FIG. 15A-15B, in some embodiments, rather than including separate male and female engagers and/or engagers having interlocking male/female portions, the links 1503 can include a plurality of straight (or otherwise non-interlocking, including keystone) engagers 1515. An outer ring 1545 or sheath can be used to hold the engagers 1515 of each link in-plane (i.e., such that the engagers 1515 do not move out and over one another). The outer ring 1545 can be, for example, a split ring that closes tighter when vacuum is applied (as shown in the transition between FIGS. 15A and 15B). Further, in some embodiments, as shown in FIG. 16, a spiral wire 1616 can extend around the links 1503 and can be attached to each link, for example, over the mounting ring 1622. The spiral wire 1616 can ensure that the outer rings 1545 stay in place (i.e., don't move axially). Referring to FIG. 30, in some embodiments, the straight or non-interlocking engagers 3015 can be shaped like keystones, i.e., can form a substantially solid annular member when vacuum is fully applied.

Figure 17:
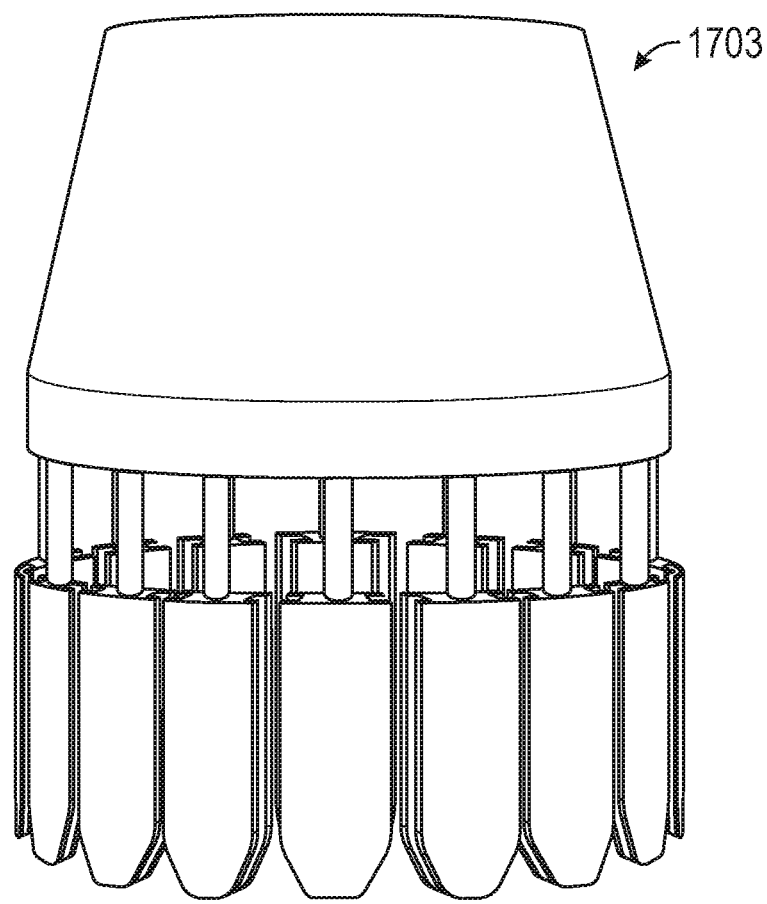
FIG. 17 shows a taper on the end linkage of a rigidizing overtube.

Referring to FIG. 17, in some embodiments, the end link 1703 can include a taper configured to create an atraumatic end for the overtube. This tapered tip region could be elastomeric, so that it tracks easily as the system advances around torturous shapes.

Figure 18:
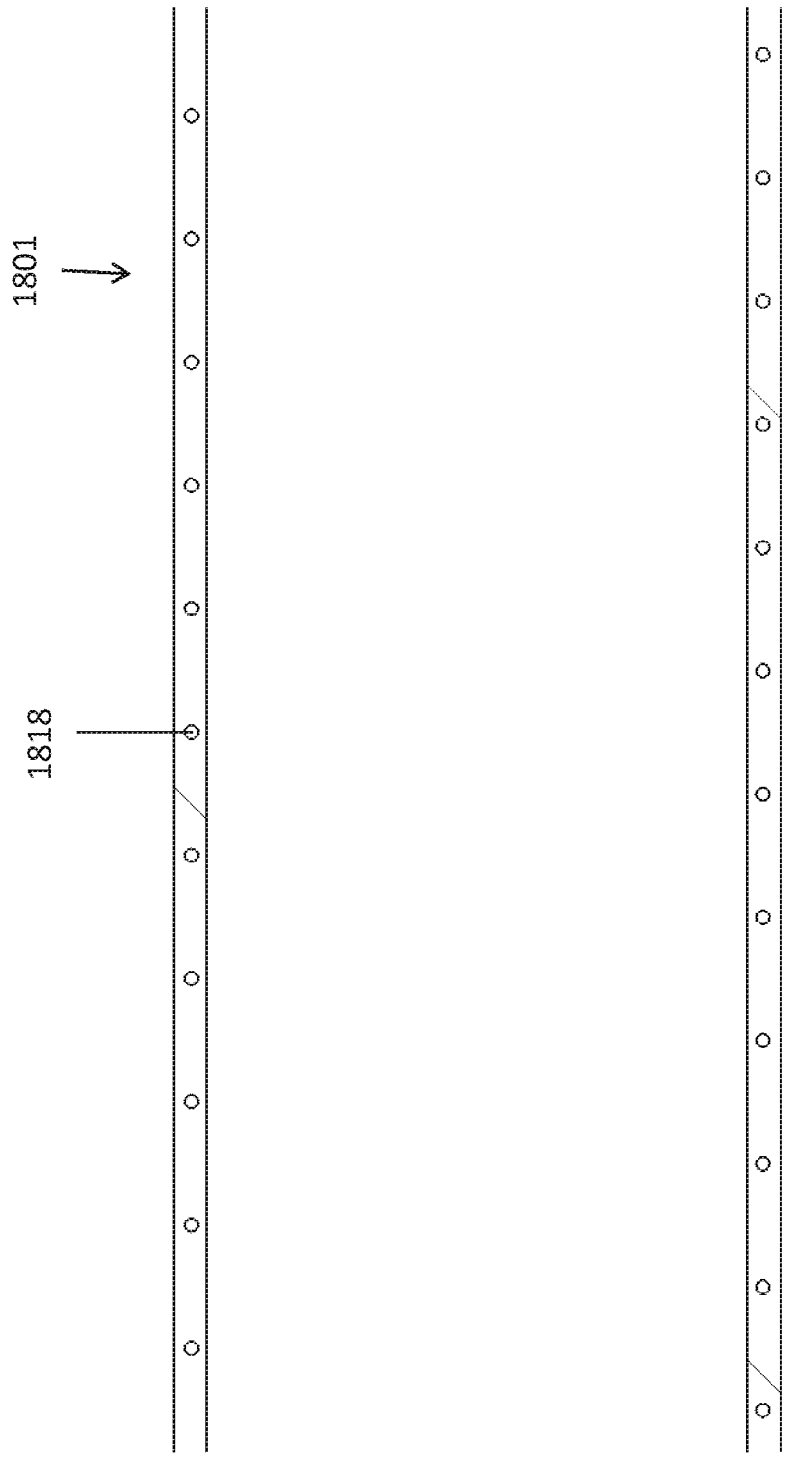
FIG. 18 shows an inner tube of a rigidizing overtube including a wire reinforcement.

Referring to FIG. 18, in some embodiments, the inner tube 1801 can be reinforced with a metal, plastic, or fiber. It can be a braid or a spiraling coil 1818 extending therethrough. This reinforcement different cross-sections, including circular, square, elliptical, or rectangular.

In some embodiments, the links for the overtubes described herein can be manufactured in an annular configuration, e.g., by insert molding. In other embodiments, as shown in FIGS. 9B and 9C, the linkage 903 can be built flat and then wrapped to form the assembled annular linkage.

Figure 22B:
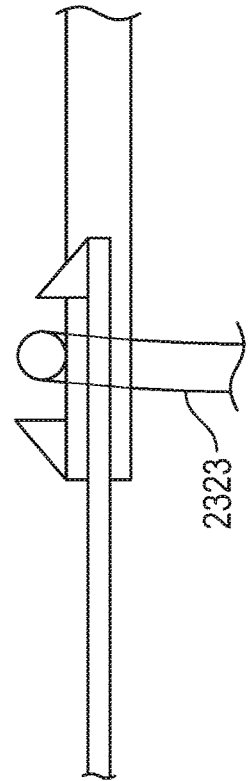
FIGS. 22A-22B show limit stops on engagers.
Figure 22A:
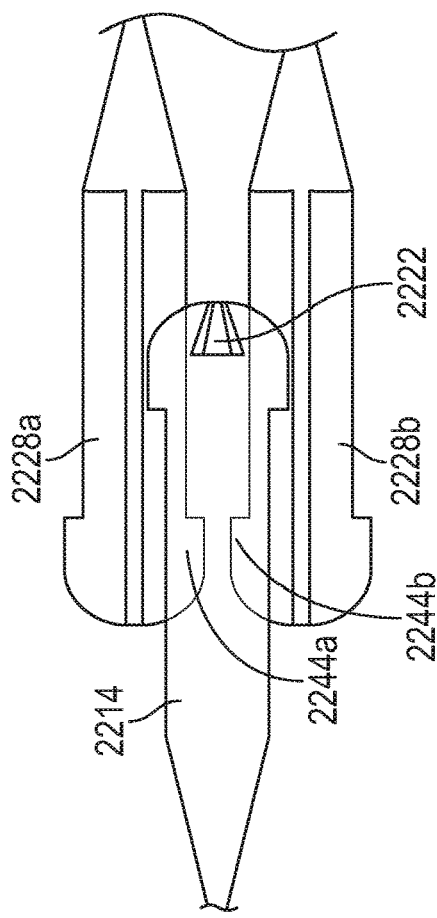

In any of the embodiments described herein, engager limit stops can be included so as to prevent the engagers from pulling too far axially and disengaging from one another. For example, referring to FIGS. 22A-22B, each male engager 2214 can include a bump 2222 or extension extending radially therefrom and positioned near the free end of the male engager 2214. Further, each female engager 2228 can include tabs 2244*a,b* extending laterally or circumferentially therefrom. As the male engager 2214 is pulled axially out of the female engagers 2228*a,b*, the bump 2222 can hit the tabs 2244*a,b* to prevent the male engagers 2214 from pulling too far axially out of alignment with the female engagers 2228*a,b*. FIGS. 38A-D and 39A-B show similar engager limit stops.

Figure 23B:
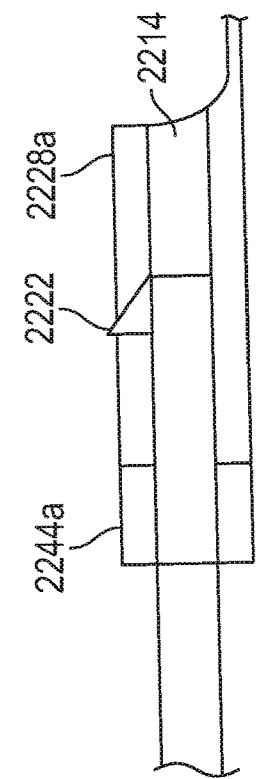
FIGS. 23A-23B show another embodiment of limit stops on engagers.
Figure 23A:
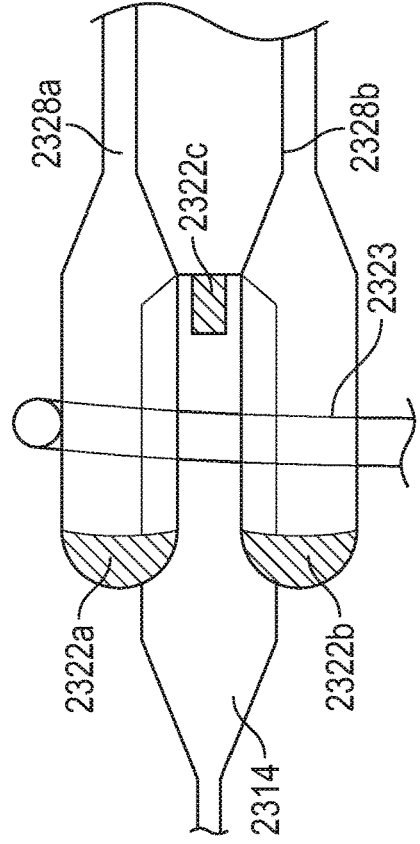

In another example, referring to FIGS. 23A-23B, both the male engagers 2314 and the female engagers 2328 can include bumps 2322*a,b,c* or extensions extending radially therefrom and positioned near the free end of the engagers 2314, 2318. An o-ring 2323 can be positioned between the bumps 2322*a,b* on the female engagers 2328*a,b* and the bump 2322*c* on the male engager 2314 such that the bumps 2322*a,b,c* will hit the o-ring 2323 when the engagers 2314, 2328 have been pulled axially apart by a set distance, thereby preventing the male engagers 2314 from pulling too far axially out of alignment with the female engagers 2328*a,b*.

Figure 38A:
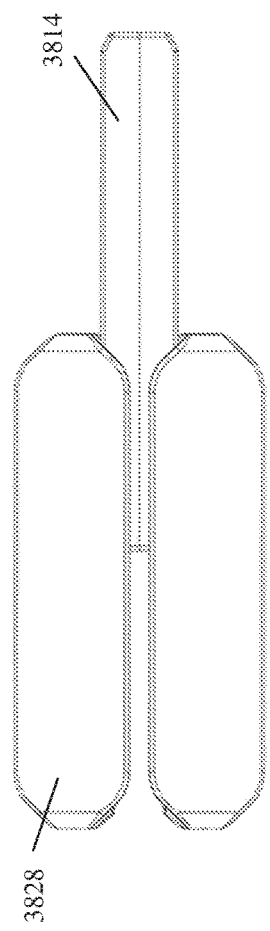
FIGS. 38A-38D show another embodiment of exemplary limit stops on engagers.
Figure 38B:
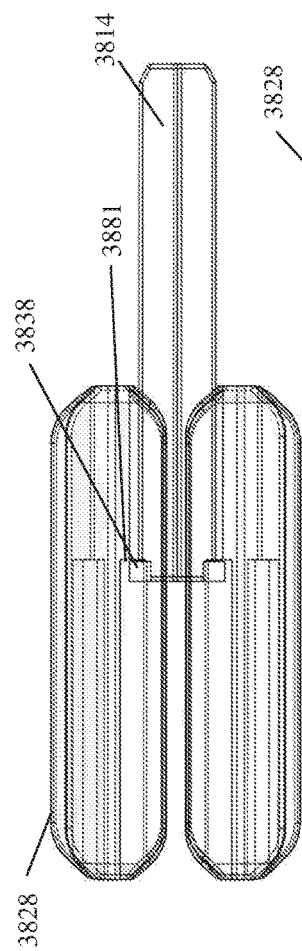
Figure 38C:
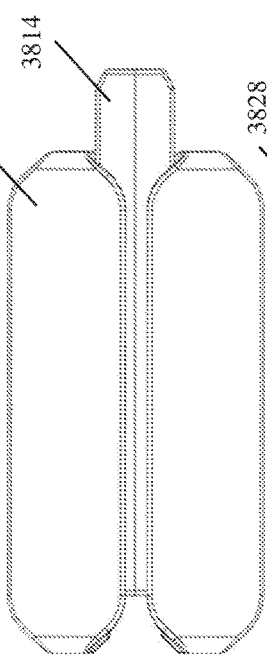
Figure 38D:
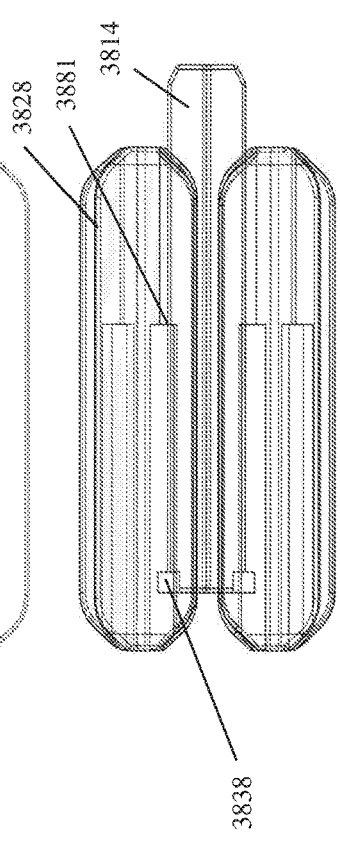

In another example, referring to FIGS. 38A-38D (FIGS. 38A and 38C are shown solid while 38B and 38D are see-through for clarity), each male engager 3814 can include a flange 3838 extending laterally or circumferentially from the free end of the engager 3814. Further, each female engager 3828 can include a cut-away at the proximal end thereof (i.e., at the end connected to the pivot) in the radial center of the engager 3828 such that an inner ledge 3881 is formed. Thus, the male engager 3814 and female engager 3828 can slide relative to one another (e.g., be pulled axially relative to one another) until the flange 3838 hits the ledge 3881 (shown in FIGS. 38A-38B), thereby preventing the male engager 3814 from pulling out of alignment with the female engager 3828.

Figures 39A, 39B:
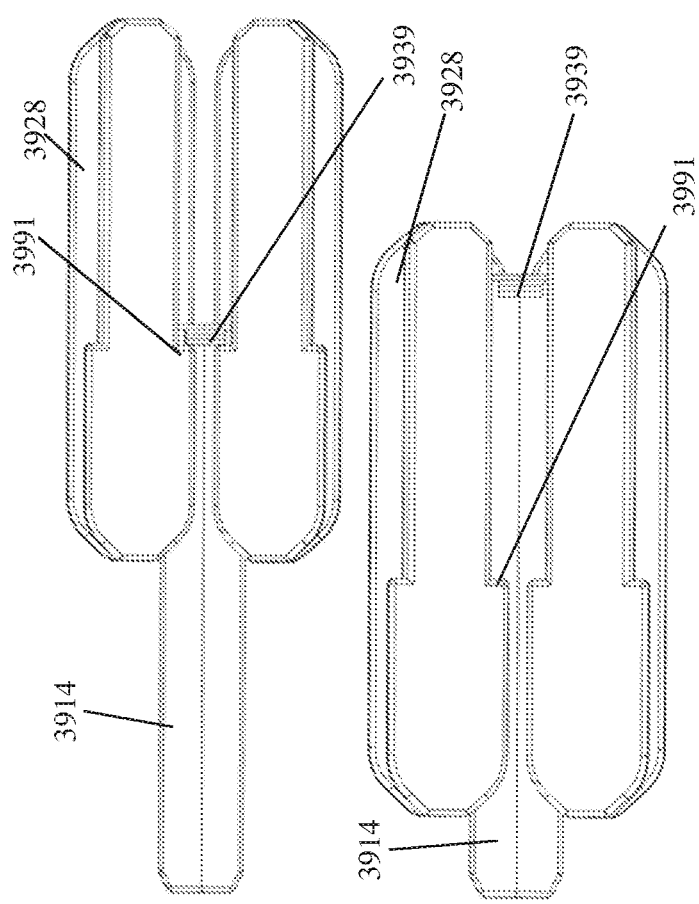
FIGS. 39A-39B show another embodiment of exemplary limit stops on engagers.

In another example, referring to FIGS. 39A-39B, each male engager 3914 can include a flange 3939 extending radially from the free end of the engager 3914. Further, each female engager 3928 can include a cut-away at a proximal end thereof (i.e., at the end connected to the pivot) in the inner or outer surface such that an inner or outer ledge 3991 is formed. Thus, the male engager 3914 and the female engager 3928 can slide relative to one another (e.g., be pulled axially relative to one another) until the flange 3939 hits the ledge 3991 (shown in FIG. 39A), thereby preventing the male engager 3914 from pulling out of alignment with the female engager 3928.

Figure 26:
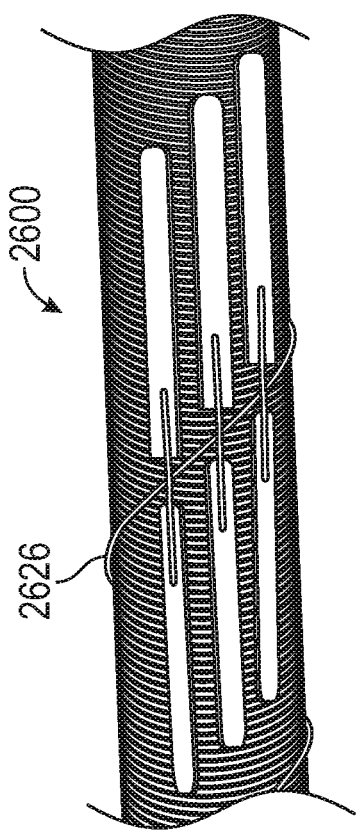
FIG. 26 shows an embodiment of a rigidizing overtube with a spiral mounting ring.

Referring to FIG. 26, in some embodiments, a mounting spiral 2626 can be used to mount the linkages and/or engagers as opposed to a plurality of individual mounting rings. The mounting spiral 2626 can extend substantially the entire length of the overtube 2600.

Figure 28B:
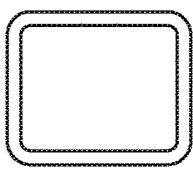
FIGS. 28A-28B show plated engagers.
Figure 28A:
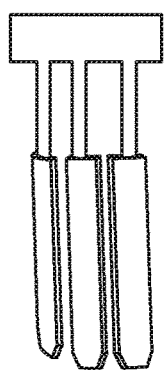
Figure 40:
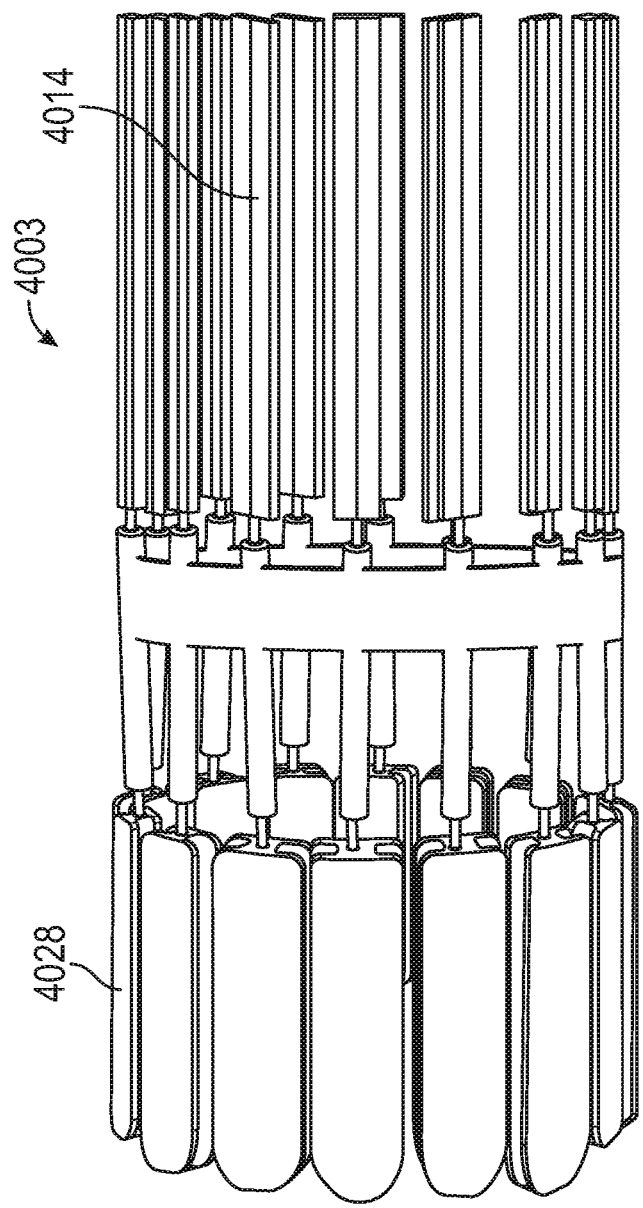
FIG. 40 shows an exemplary linkage including a metal coating.

Referring to FIGS. 28A-28B, any portion of the linkages described herein, including the engagers, can be plated. For example, referring to FIG. 40, a metallic coating can cover all or part of the linkage 4003 (or any linkage described herein). The metallic coating can enhance the stiffness and provide enhanced engagement between engagers 4014, 4028. In some embodiments, the metallic coating can be aluminum, stainless steel, or titanium. The coating can be, for example, 1000-2000 angstroms thick, such as around 1500 angstroms thick In some embodiments, the engagers can include a friction enhancing plastic to aid in engagement. For example, the engagers can include styrene butadiene block copolymer (SBC) with an impact modifier. The use of SBC could advantageously combine the appropriate balance of strength and stiffness while maintaining high material-on-material grabbing or engagement.

The pivots described herein can advantageously provide an engineered combination of high axial tensile and compression stiffness and high resistance to shear loads while providing a low bending force. This enables the links to conform to the bending of the inner tube, such that the entire system maintains the requisite high flexibility when it is not in the rigidized condition.

For example, the pivots can exhibit bending force of less than or equal to 35 grams, 20 grams, 10 grams, 5 grams, or even 1 gram. These values are attained wherein the bending force is the load required to deflect the element 45 degrees and the load is applied 1 cm from its attachment.

Figure 27B:
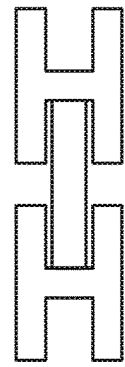
FIGS. 27A-27B show the reduction of space between engagers upon application of vacuum.
Figure 27A:
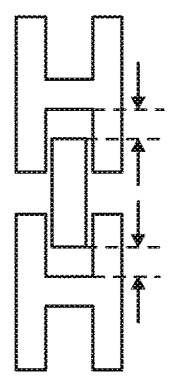

Referring to FIGS. 27A-27B, the male and female engagers described herein can work by having a gap therebetween when no vacuum is applied (FIG. 27A) and little or no gap when vacuum is applied (FIG. 27B).

In some embodiments, a rigidizing overtube can include links with extendable locking pivots in place of the engagers described herein.

Figure 32A:
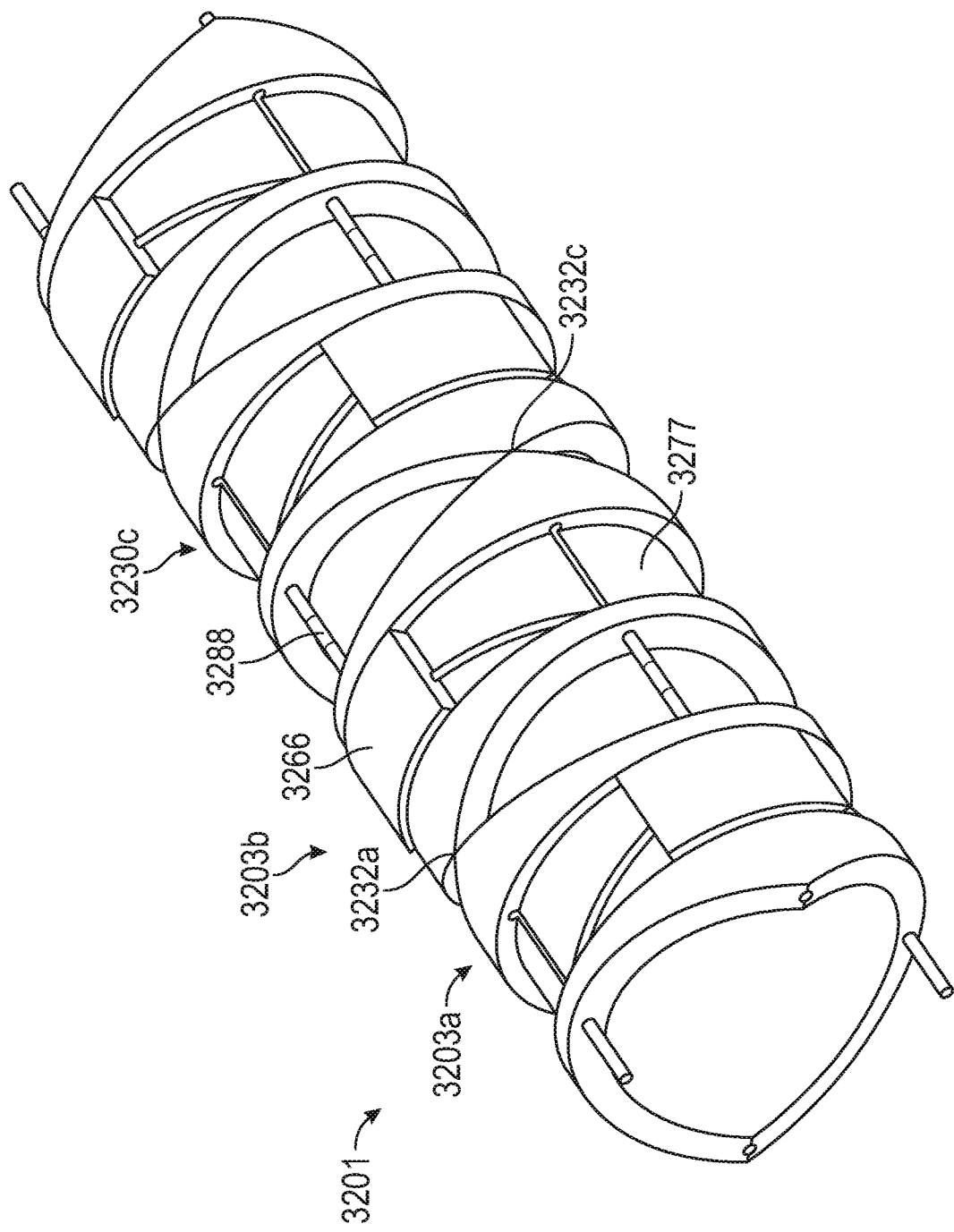
FIGS. 32A-32F show a dynamically rigidizing system that includes extendable locking pivots.
Figure 32B:
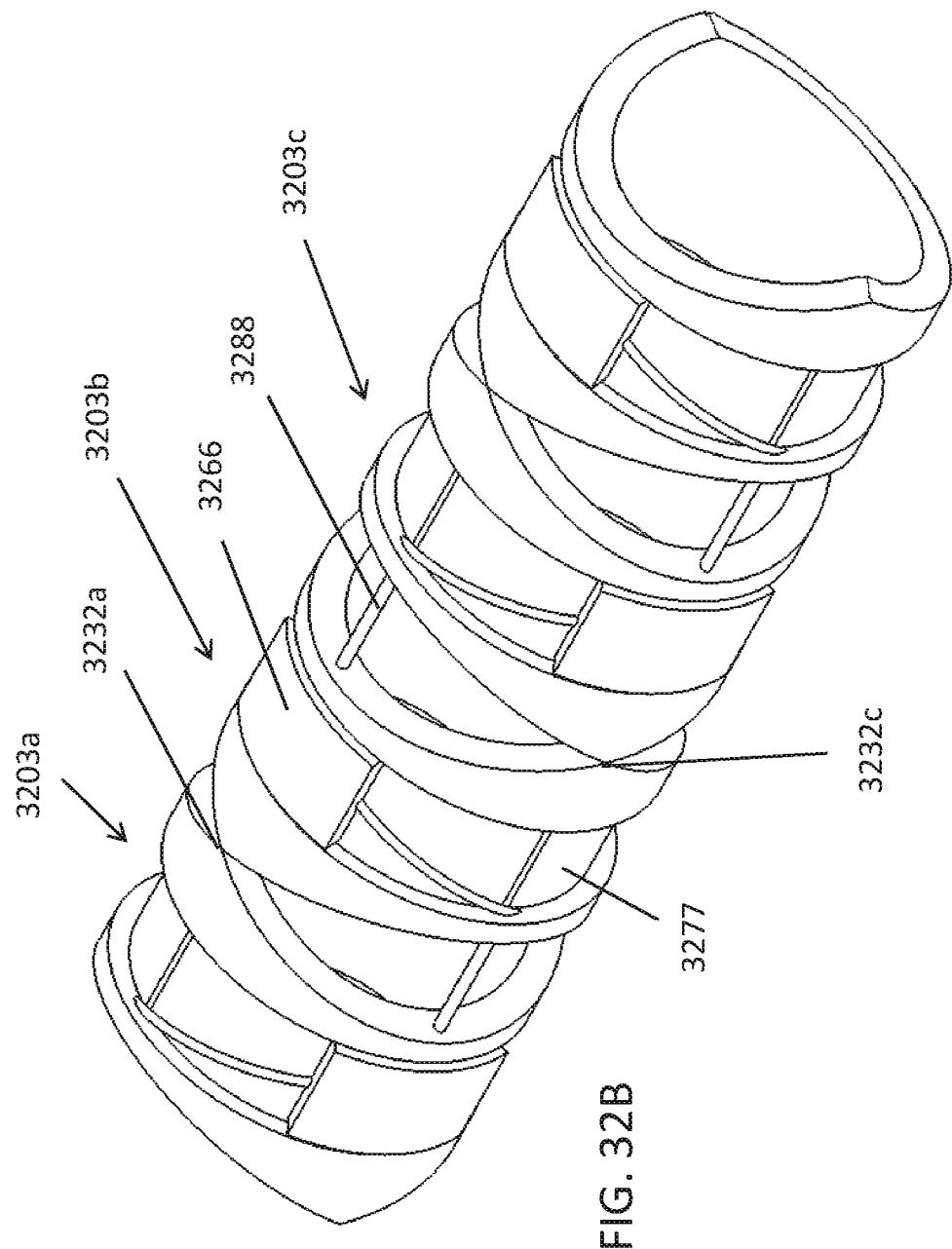
Figure 32D:
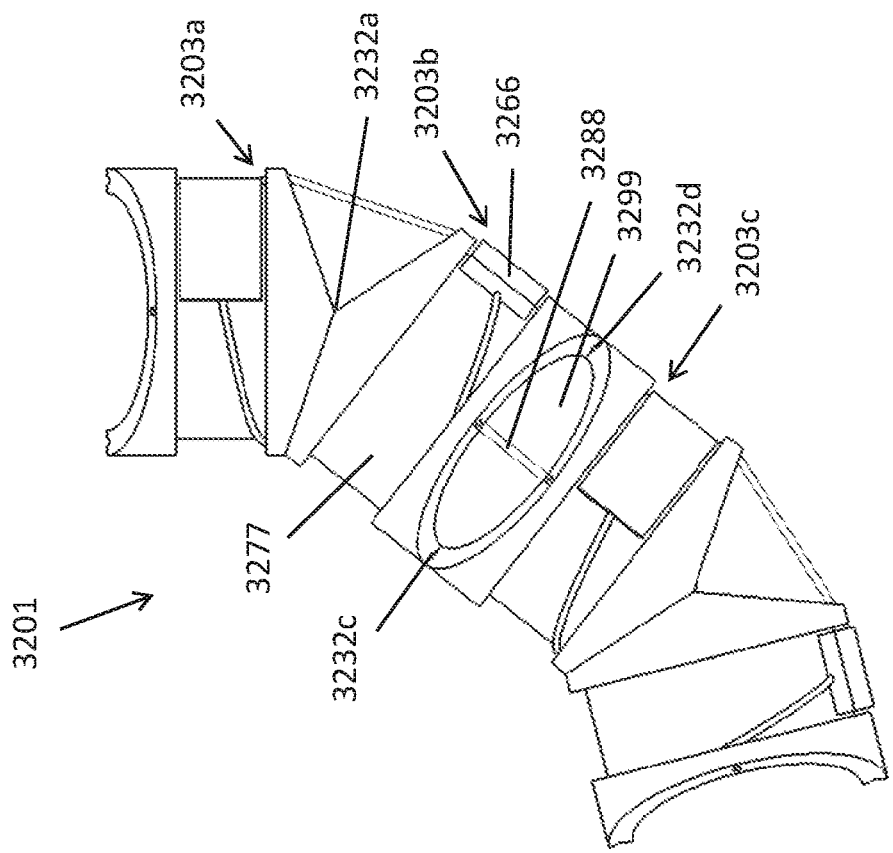
Figure 32C:
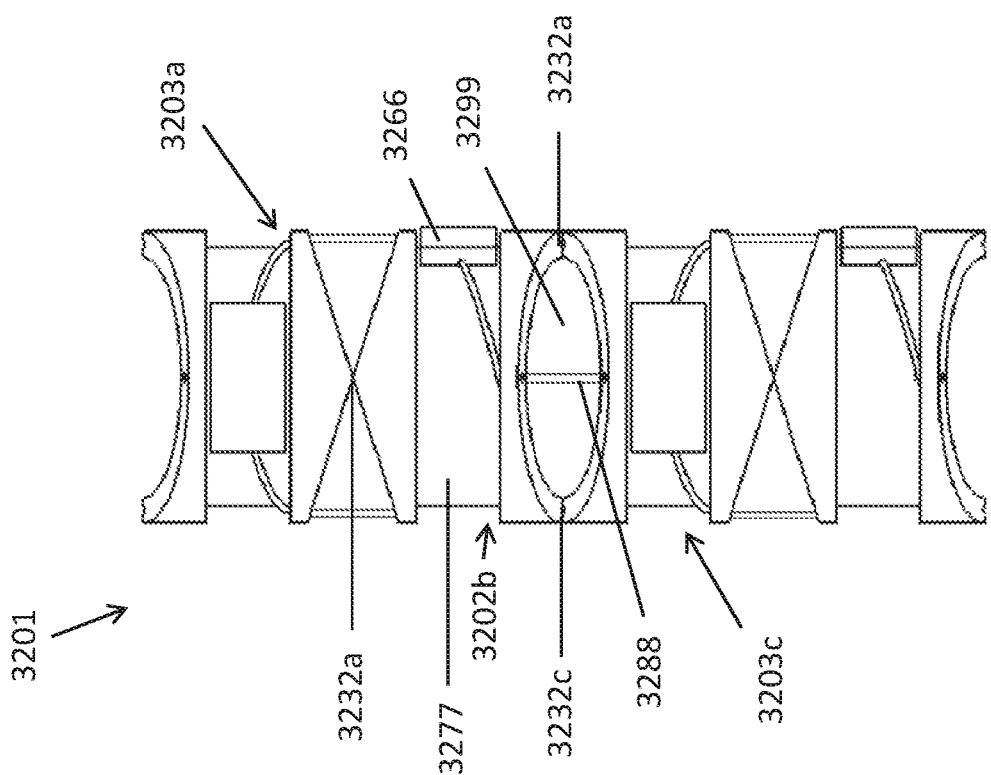
Figure 32F:
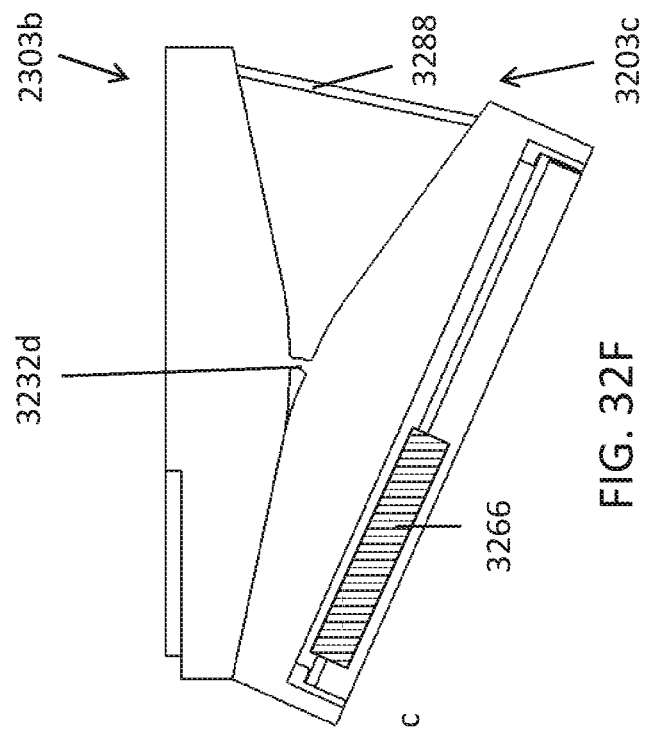
Figure 32E:
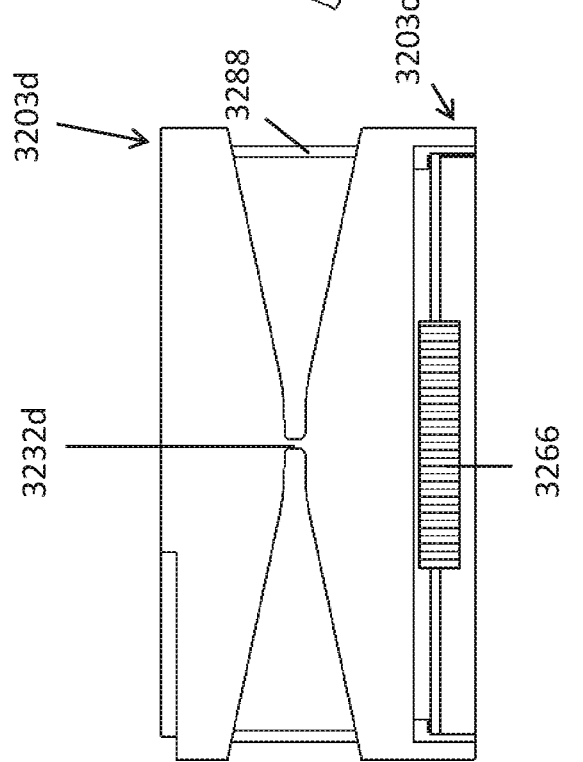

For example, referring to FIGS. 32A-32F, the linkage system 3201 (for use as part of an overtube with an inner tube, outer tube, vacuum pump, etc. as described above) can include a plurality of linkages 3203*a,b,c*. The linkages 3203*a,b,c* can be connected to each other through a pivot point 3232 or pivot points 3232*a,b,c,d* (which can be, for example, wire pivot points). Each pivot point 3232 can allow bending with one degree of freedom between linkages (FIG. 32D shows the bend at pivot points 3232*a,b* while FIG. 32F shows the bend at pivot points 3232*c,d*). Further, the linkages 3203*a,b,c* can be arranged in alternating fashion with every other linkage connected with the pivot points 3232 positioned 90 degrees away from the previous linkage (see, e.g., pivot points 3232*a,b* connecting linkages 3203*a,b* relative to pivot points 3232*c,d* connecting linkages 3203*b,c*). Each linkage 3203 can have cut-outs at the proximal and distal ends thereof extending from the pivot-points to as to allow bending of the linkages relative to one another (see, e.g., cut-out space 3299 between linkages 3203*c* and 3203*d*). Further, each linkage can be connected to a neighboring linkage by a respective tensile member 3288 (only one tensile member is labeled for clarity). The tensile member 3288 can be fixed relative to one linkage (e.g., linkage 3203c) and movable within a track of the neighboring linkage (e.g., within track 3277 of linkage 3203b). Movement of the tensile member 3288 within the track 3277 allows the tensile member 3288 to lengthen when on the outside of the curve and shorten when on the inside of the curve during bending of the overtube. Further, a clamp 3266 can be attached to the tensile member 3288, which can move within the track 3277 as well. When the vacuum is applied, the outer sleeve compresses the clamp 3266 onto the link 3203b and keeps the clamp 3266, and therefore the tensile member 3288, from moving. Since the tensile member 3288 cannot move upon application of the vacuum, the links 3203c,d cannot bend around the pivots 3232c,d, causing the linkage system 3201 to adopt a fixed or rigid configuration. When vacuum is removed, the clamp 3266, tensile member 3288, and links 3203 are free to move relative to one another.

The linkages 3203 can be shaped to allow for a specific degree of bend before travel is stopped, which can be called angled theta ($\theta$). Theta can be allowed to change freely when the overtube is in the flexible configuration and can become fixed when the overtube is in the rigid configuration (i.e., when vacuum is pulled). When flexible, the tensile member 3288 can slide relative to one or both links 3203c,d. When rigid, the tensile member 3288 is fixed relative to both links 3203c,d.

The tensile member 3288 can bridge the gaps on both sides of the device (e.g., can run along one gap and then 180 degrees along the opposite gap). In some embodiments, however, the member can be a rigid member that is configured to handle both compression and tension. In such embodiments, the compression/tensile member need only run along one side of the gap. When bending loads are applied in one direction, the member will be under compression but will not buckle. When bending loads are applied in the other direction, the member will be in tension but will not buckle. In one exemplary embodiment, male/female engagers as described herein can bridge the gap, moving axially relative to each other without vacuum and locking in place when vacuum is applied.

Another exemplary linkage system 5501 is shown in FIGS. 55A-55E. The linkage system 5501 similarly include a plurality of linkages 5503a,b,c,d connected to each other with tensile members 5588 and pivot points 5533. The tensile members 5588 of system 5501 are each flexible and can bend 180 degrees to allow for bending over the linkage system 5501 in all directions. The tensile member 5588 can be fixed at one end (i.e. relative to one linkage (e.g., at location 5555)) and movable at the opposite end with respect to a neighboring linkage. In contrast to linkage system 3201, the linkage system 5501 can include engagers at the movable end of each tensile member 5588 that allow movement of the tensile members 5588 (and thus bending/movement of neighboring linkages 5503 relative to one another). That is, each tensile member 5588 can be connected to (or formed from) a male engager 5514 (which can be any of the male engagers described herein). The connection point of the tensile member 5588 to the neighboring linkage 5503 can be via a female engagers 5528 (which can be any of the female engagers described herein) that are configured as part of the clamps 5566. For example, the male engagers 5514 can be wedge-shaped on either side while the female engagers 5528 can include corresponding wedge-shaped cut-outs. Movement of the tensile member 5588 using the engagers allows the tensile member 5588 to lengthen when on the outside of the curve and shorten when on the inside of the curve during bending of the overtube.

When the vacuum is applied, the outer sleeve compresses the clamp 5566 onto the tensile member 5588 to prevent the tensile member 5588 from moving. Since the tensile member 5588 cannot move upon application of the vacuum, the links 5503 cannot bend, causing the linkage system 5501 to adopt a fixed or rigid configuration. When vacuum is removed, the clamp 5566, tensile member 5588, and links 5503 are free to move relative to one another.

In some embodiments, the linkages of the pivot locking systems can be 0.4 inches long with a maximum bend angle of +/−40 degrees from neutral (roughly 1.5" bend radius). The tension member can be a UHMWPE fiber bundle. The tensile member can be wrapped within the track 1.5 times to provide capstan drag and boost the clamping force. The clamp can have a surface area of roughly 0.15"×0.4" to maximize vacuum force while allowing for +/−40 degrees of bending. The clamp can be smooth and rely solely upon friction to hold the tensile member in place. The inner sleeve can be 50 A urethane 0.010" thick and is bonded periodically to the inner surface of the links. Further, the outer sleeve can be 50 A urethane 0.010" thick and is a clearance fit on the outside of the links with no attachment to the links. The clamp described herein can be attached to the tensile member or can clamp down onto the tensile member. Further, the clamp may push down radially or axially onto the tensile member. In some embodiments, the clamp can include serrations on the bottom thereof to mate with the link. The tensile member can be fiber, string, thread, wire, or cable. In some embodiments, the tensile member can be a continuation of the pivot cable or thread. Further, in some embodiments, there can be two tensile members that undergo axial translation instead of rotation. In such an embodiment, two clamps can be used on each link to clamp both tensile members down.

The extendible locking pivot design, such as that described with respect to FIGS. 32A-32F, can advantageously have high torsional stiffness, high compression stiffness, and high tensile stiffness with or without vacuum. Further, such designs can have high flexibility for small bend radii, can have a small diameter, and can have a substantially circular cross-section.

Figure 36A:
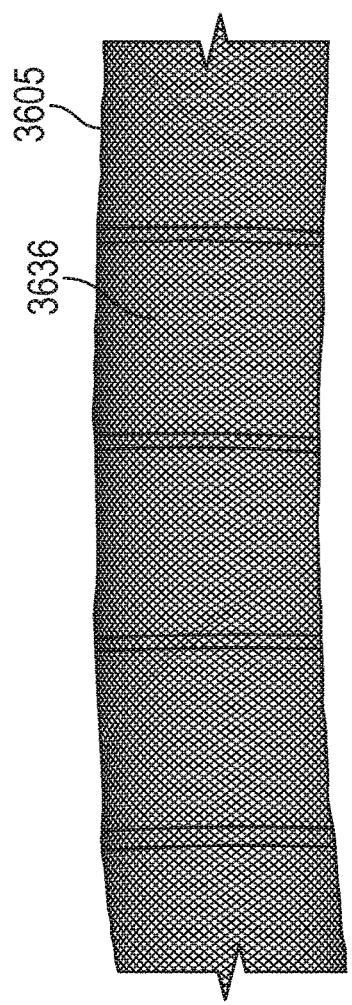
FIGS. 36A-36B show exemplary braids for use with a dynamically rigidizing overtube.
Figure 36B:
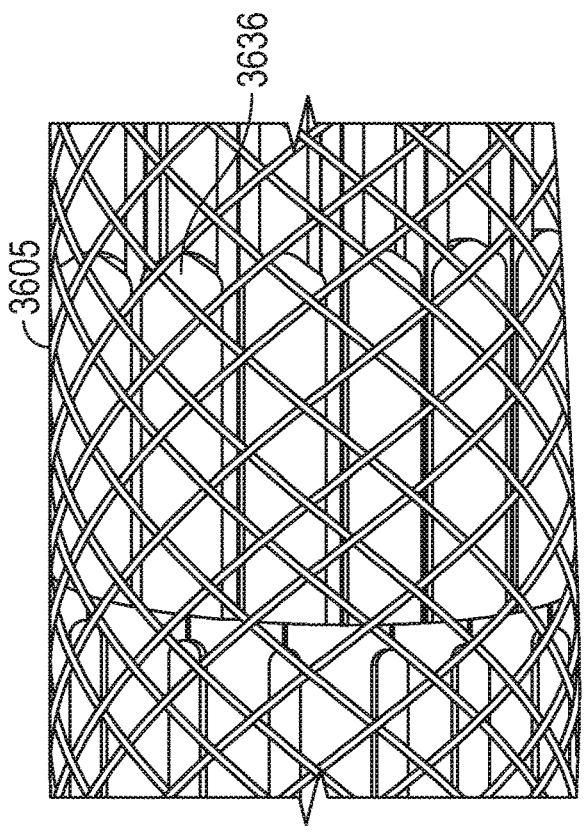
Figure 37:
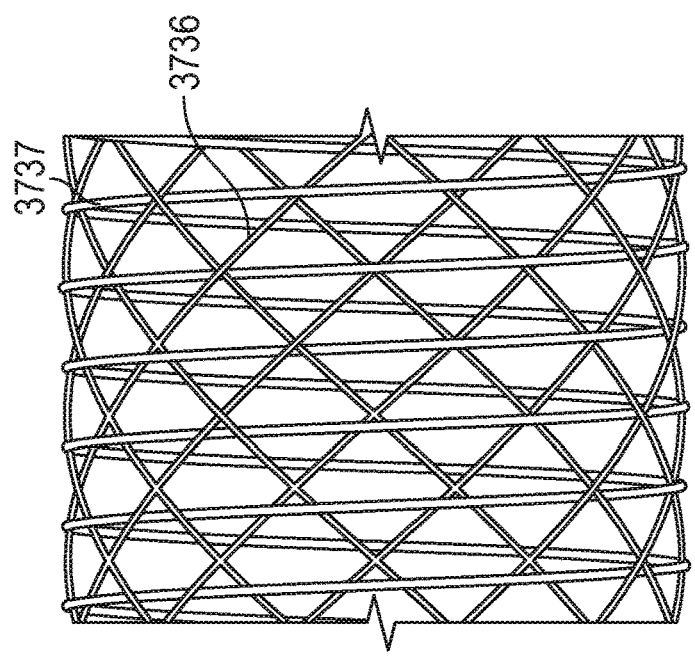
FIG. 37 shows hoop strands incorporated into a braid for use with a dynamically rigidizing overtube.

Referring to FIGS. 36A-37, in some embodiments, the outer layer of the overtubes described herein can include a braid therein or therearound. For example, as shown in FIGS. 36A-36B, the outer layer 3605 can include a braid 3636 therein to provide greater torsional stiffness, shear stiffness under vacuum, and tension without vacuum without substantially affecting the unvacuumed bending stiffness of the overall device. Additionally, the braid 3636 can advantageously help smooth over the outside of the engagers to make the device more patient-friendly. The braid 3636 can be made, for example, of fiber, metal, or plastic. Further, the braid 3636 can include round strands, flattened strands, or a combination of the two.

In some embodiments, the braid can be layered on top of other layer(s) of braid. Braid angles can be precisely engineered, for example, to 10 to 30 degrees, with zero degrees being in-line with the major tube axis and 90 degrees being orthogonal to that access.

Braid filaments can be of plastic or metal, such that it exhibits good tensile and compression properties. The filaments can be homogenous, or they can have a base material coupled with a surface treatments, for example for enhanced gripping. Fibers can be utilized for enhanced tensile properties. Cross sections can be multiple geometries, including round, square, or rectangular.

In one embodiment, the braid can include 48 strands of 0.002" by 0.02" PET flat filaments braided with a 0.7" nominal diameter at a 45 degree braid angle.

In some embodiments, referring to FIG. 37, hoop strands 3737 can be incorporated into a braid 3736 to provided increased stiffness when loaded in compression. The hoops strands 3737 can be, for example, woven through the strands of the braid 3736 (e.g., alternately over two strands of the braid and under two strands of the braid). Additionally, the presence of an undersurface (e.g., the links) enables the braid 3736 to resist torsion in both twisting directions and to resist tensions when there is no vacuum on the system.

In some embodiments, there can be one or more slip layers in the overtube to help the various layers (braid and/or engagers) move relative to one another. The slip layer can advantageously enhance the baseline flexibility of the overtube to allow the layers to move relative to one another. In one embodiment, the slip layer(s) can be made of low coefficient of friction materials, such as thin film fluoropolymers (FEP, chemfilm, PTFE, with thicknesses as low as 2, 4, 6 microns). In one embodiment, the slip layer(s) include powders, such as talcum or cornstarch. In one embodiment, the slip layer(s) can be a coating. In one embodiment, the slip layer(s) can be slip additives added to an elastomer. In one embodiment, the slip layer(s) can be sheaths of thin plastic films that are inherently lubricious, such as low-density polyethylene (LDPE). In one specific example, the slip layer is made of a thin spiral-wrapped film, such at 0.0005" FEP or 0.00025" Chemfilm (St. Gobain).

In some embodiments, engagers can be photo-etched. In some embodiments, engagers can be etched down, welded, or vacuum furnace diffusion bonded.

In some embodiments, the wire pivots can be spot welded to the engager and/or the mounting ring.

Any of the links described herein can advantageously be thin and made of a high-modulus material (i.e., a material with a modulus over 200 ksi. They could be made of a material of very high modulus, for example LCP (Liquid Crystal Polymer), or stainless steel. Should the links be comprised of lower modulus materials, their stiffness could be augmented through the selective insertion of members of higher stiffness (i.e., insert molded cables or wire).

The links can be relatively short, for example, for a colonoscopy application with a pitch length of 0.8, 1 1.2, or 1.4" long. For a colonoscopy application, the overtube length can be approximately 95 cm long. Being short helps the system to not suffer from capstan drag effects, i.e., the cumulative exponentially-rising drag that occurs when long members accumulative successive wraps. Moreover, because this design does not suffer from capstan drag, it does not lose stiffness as a function of increasing length from the base handle. Thus, the overtube can have, for example, a length of 95 cm to accommodate a colonoscope, but the relatively short links allow the bend differential to be taken up locally, allows bending easily and smoothly (i.e. the circumferential difference between the inner and outer bend radius can be realized locally at each individual link as the engagers move past each other). The links (or series of engaged links) described herein can further be configured so as to effectively carry both tensile and compressive loads without deforming, deflecting, or buckling when a load is applied.

Figure 24A:
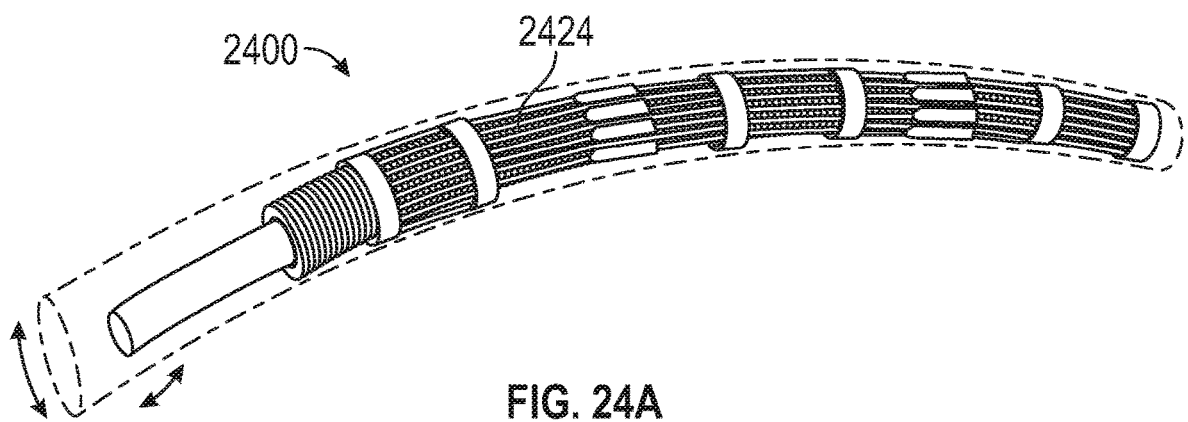
FIGS. 24A-24B show a steerable rigidizing overtube.
Figure 24B:
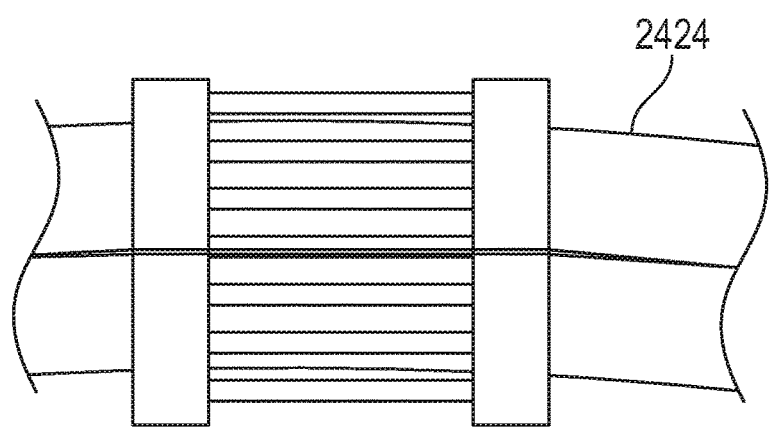

In some embodiments, the overtubes described herein can including steering elements to aid in moving the overtube through the body lumen when the overtube is in the flexible configuration. For example, referring to FIGS. 24A-24B, the overtube 2400 (which can include any of the rigidizing and other features described herein) can include cables 2424 extending therethrough that can be connected, for example, through anchoring rings. Applying tension on the cables 2424 when the overtube 2400 is in the flexible configuration can create compression in the overtube 2400, thereby causing it to bend in the direction of the applied compression.

Figure 25:
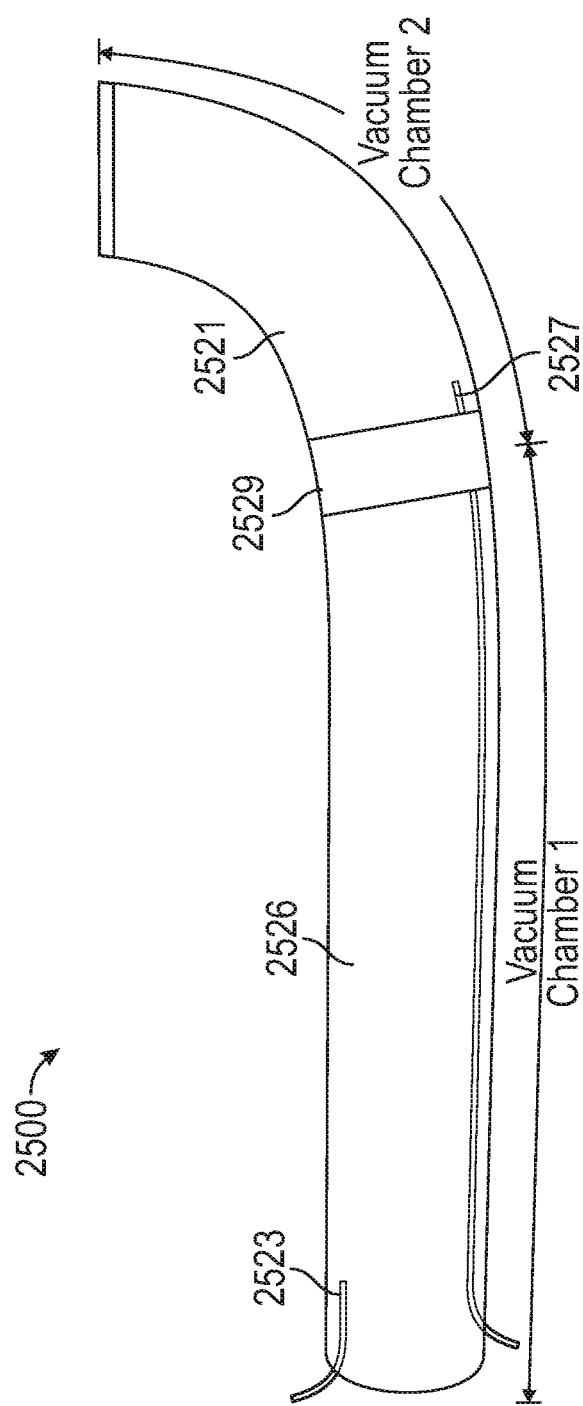
FIG. 25 shows a rigidizing overtube with selectively rigidizing zones.

Referring to FIG. 25, in some embodiments, the overtube 2500 can be separable into chambers. Each chamber can be controlled by a separate vacuum (and/or without vacuum) to allow independent rigidizing of chambers. That is, as shown in FIG. 25, there can be a first vacuum chamber (with its own vacuum line 2523) that controls the proximal portion 2526 and a second vacuum chamber (with its own vacuum line 2527) that controls the distal portion 2521. A pressure seal 2529 can separate the two chambers of proximal portion 2526 and distal portion 2521.

Figure 57A:
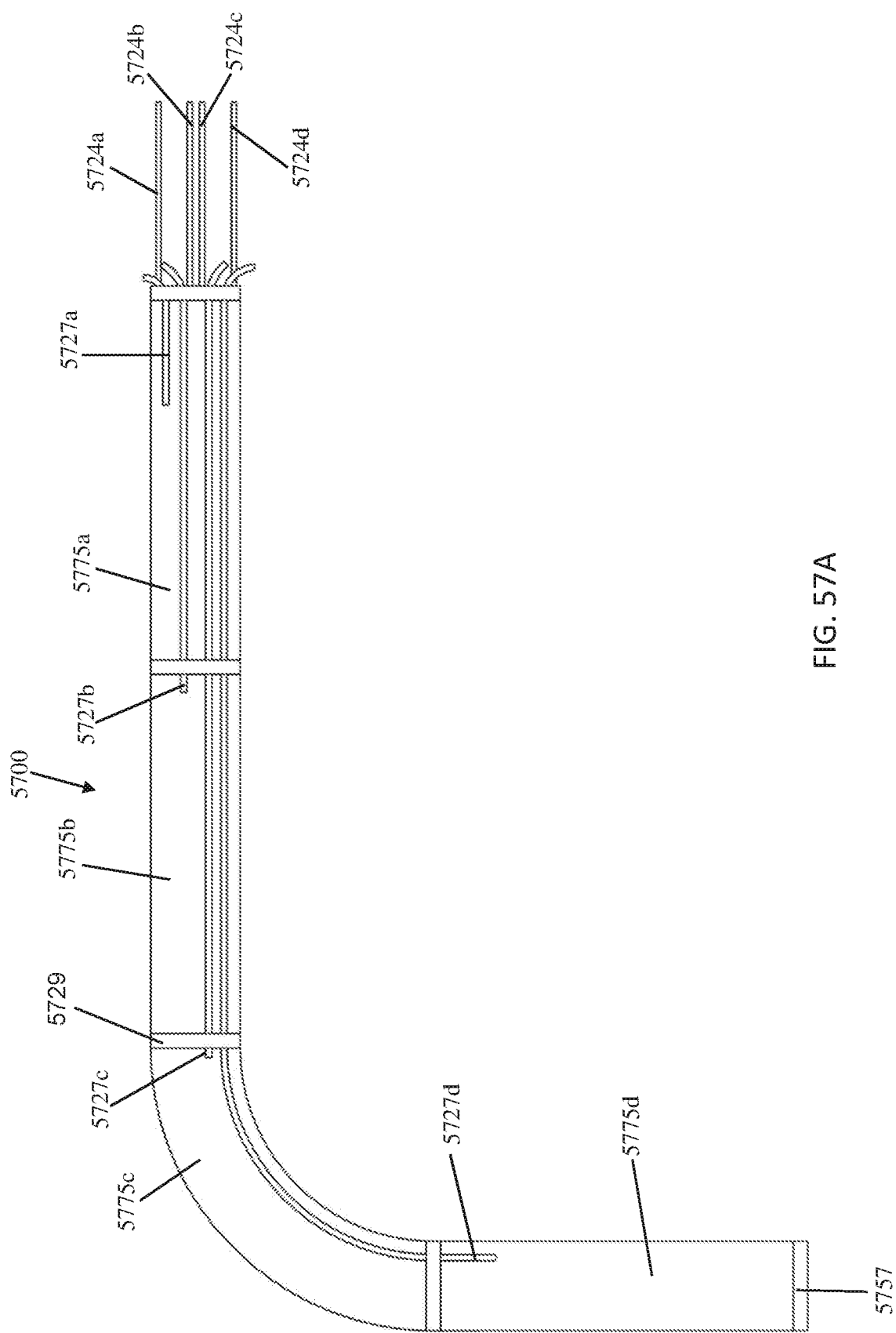
FIGS. 57A-C show an exemplary rigidzing overtube with separate vacuum chambers and steering along the length thereof.
Figure 57C:
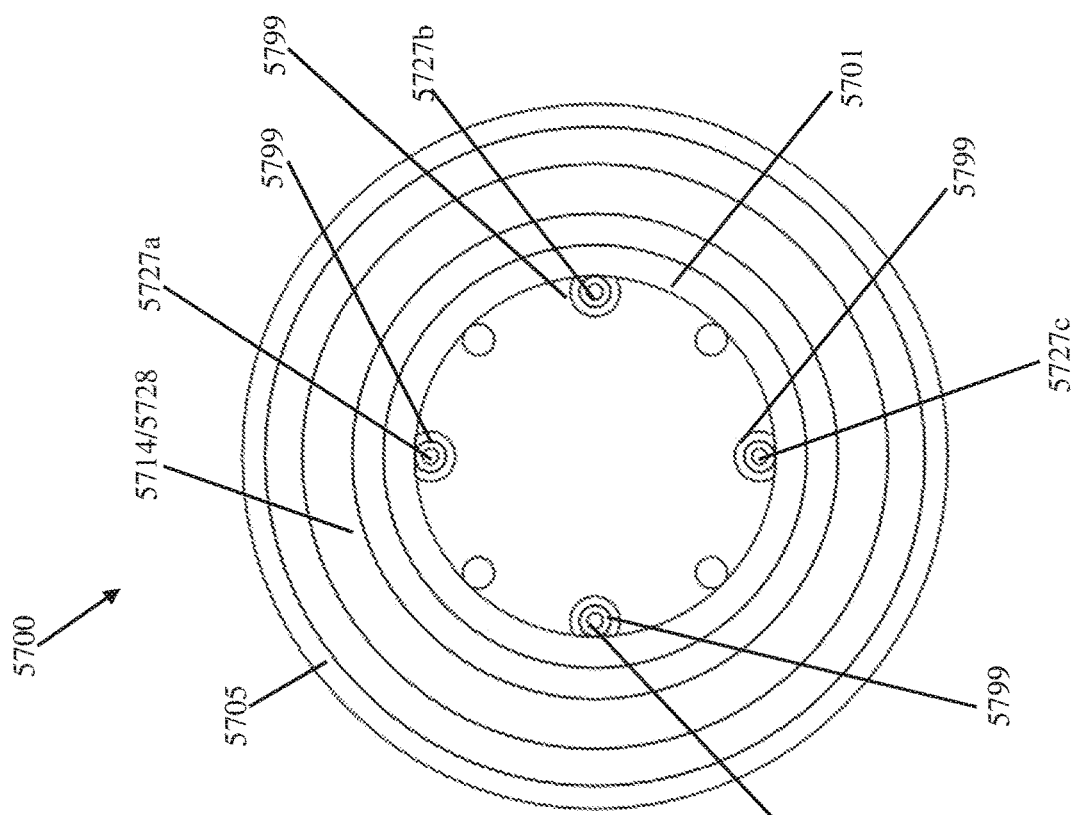
Figure 57B:
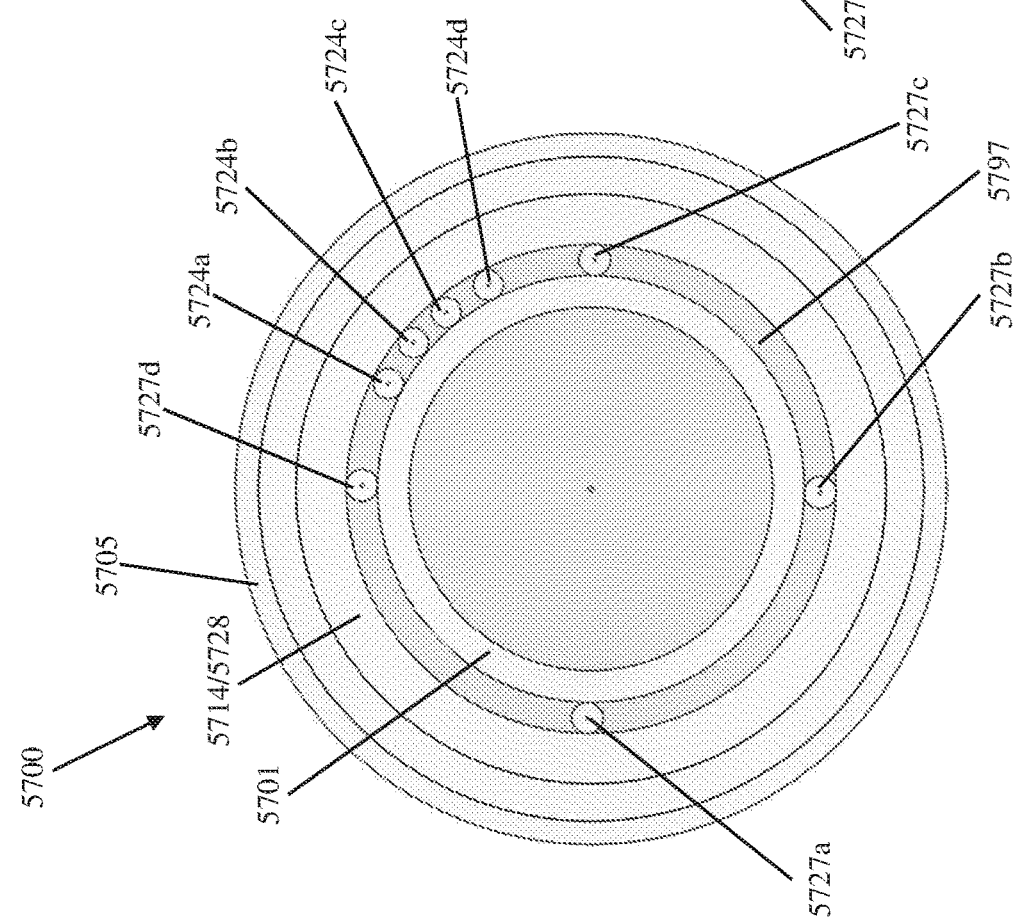

Referring to FIGS. 57A-57C, in some embodiments, the overtube 5700 can have both separate chambers and a steerable distal end. Referring to FIG. 57A, there can be a plurality of cables 5724a,b,c,d that extend from the proximal end to a distal anchor point 5757 (cables are not shown extending the length of the overtube 5700 for clarity purposes only). Further, there can be a plurality vacuum chambers 5775a,b,c,d (e.g., four vacuum chambers), each with its own vacuum line 5727a,b,c,d. Pressure seals 5729 can extend between each chamber. Further, the distal anchor point 5757 can also include a pressure seal. The cables 5724 can be managed using cable guides (e.g., at least one, such as 1-4 cable guides in each vacuum chamber 5775). The overtube 5700 thus includes multiple zones of rigidization (via chambers 5775) and cables 5724 that extend the entire length of the overtube 5700, but are anchored only at the tip 5757. Any vacuum zones that are in the flexible state can be steered or deflected in the direction of cable tension while the zones that are rigidized will remain in their position and not be deflected. Advantageously, this design allows alternating of which zones are under vacuum and/or direction of steering to form very complex shapes and provide navigation through the anatomy with minimal looping. A cross-section of the overtube 5700 is shown in FIG. 57A. As shown, the cables 5727 and/or vacuum lines 5724 can extend, for example, in a radial gap 5797 or space between the inner tube 5701 and the engagers 5714/5728 (and thus can also extend beneath the vacuum sheath 5705). In some embodiments, as shown in FIG. 57C, the cables 5727 and vacuum lines 5724 can extend within the central opening of the overtube 5700 (cable guides 5799 are also shown in FIG. 57C). It should be understood that the overtube 5700 can also be part of a scope.

Another steering mechanism is shown in FIG. 42A. The overtube 4200a can include an outer coil 4241a wound therearound (e.g., at the distal end of the overtube 4200a). Axially aligned loops 4261a can be positioned at each wind of the coil 4241a. A pull-cable 4262a can be routed through each loop 4261a. As tensile load is applied to the pull-cable 4262a, the tube 4200a can bend into an arc, thereby providing steerability of the overtube 4200a.

As another example, as shown in FIG. 42B, the overtube 4200b can include rigid links 4263b connected together via pivots 4264b (e.g., a wire pivot). A pull-cable 4262b can be attached to the links such that as a tensile load is applied to the pull-cable 4262b, the tube 4200b can bend into an arc, thereby providing steerability of the overtube 4200b.

In some embodiments, the overtube can include motors or other features (e.g., sensors, communication, computation, illumination) for steering or stabilizing individual links or segments.

When the overtubes described herein are in the rigid configuration can advantageously maintain shape despite loads being placed therein. For example, in the rigid configuration, the overtube can hold its shape or angles against applied torque of greater than 1 Nm, 2 Nm, or 3 Nm.

Figure 31:
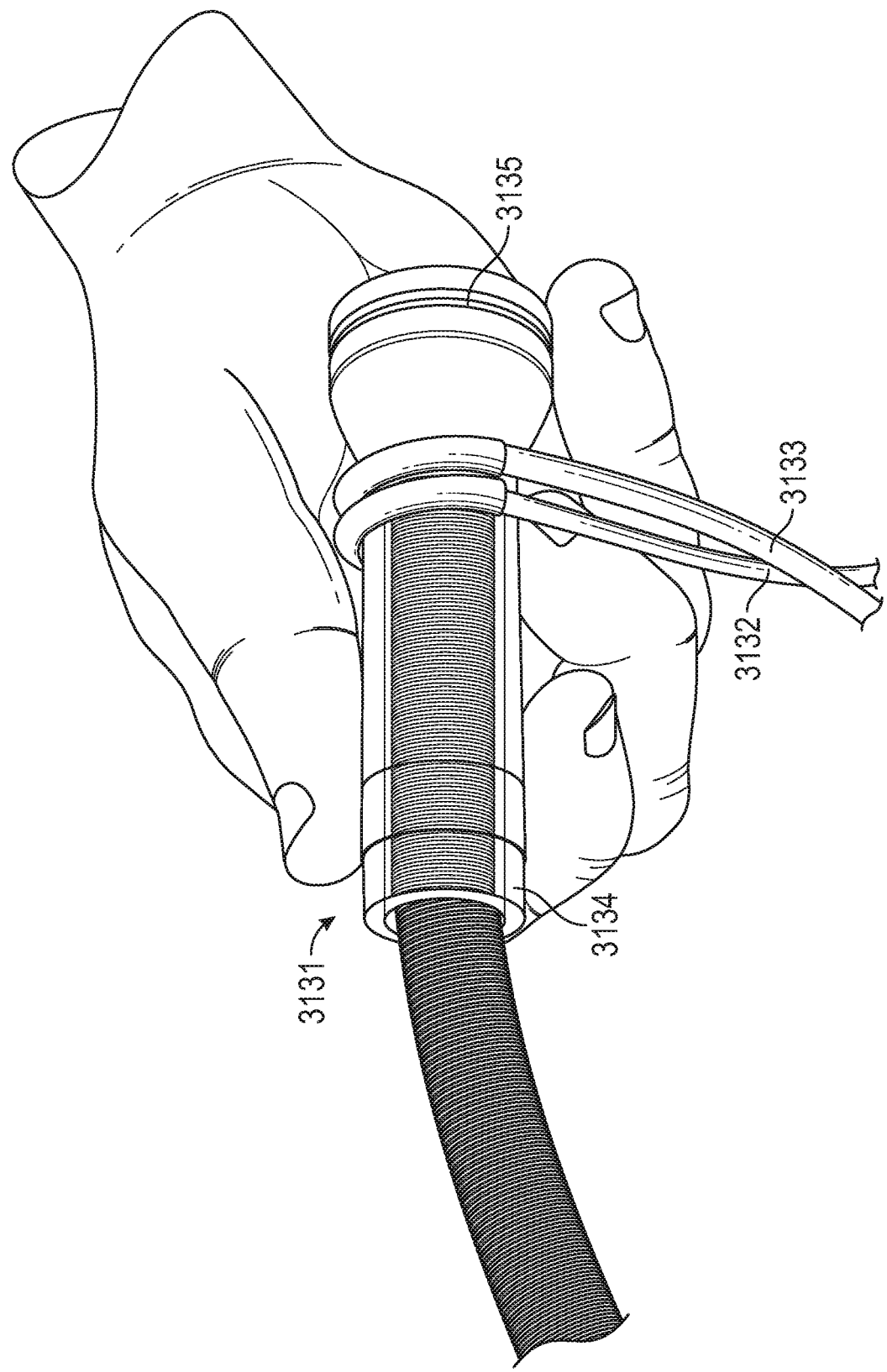
FIG. 31 shows an exemplary handle for use with a dynamically rigidizing overtube.

Any of the overtubes described herein can be used with a handle configured to allow manual manipulation of the device. An exemplary handle 3131 is shown in FIG. 31. The handle 3131 includes a vacuum line 3132 for providing vacuum to rigidize the overtube, a lubrication line 3133 to provide lubrication between the overtube and the scope, a vacuum seal bond 3134, and a lubrication seal 3135.

A similar handle 4831 is shown in FIGS. 48A-48D. The handle 4831 includes an activation element (button 4848) configured to activate the vacuum (the button is shown off in FIGS. 48A and 48C and on in FIGS. 48B and 48D). Further, flow path within the handle 4831 can include a vacuum input port 4849 configured to be attached to the vacuum source, an overtube port 4850 that connects to the overtube via output 4853, and a vent port 4851 that connects to atmosphere. As shown in FIG. 48A, when the button 4848 is in a distal "off" position (i.e., such that vacuum to the overtube is supposed to be off), the vent port 4851 and overtube port 4850 are in communication with one another. As shown in FIG. 48B, when the button 4848 is in a proximal "on" position (i.e., such that vacuum to the overtube is supposed to be on), the overtube port 4850 and the vacuum port 4849 are in communication with one another. The handle 4831 can be configured to be bonded to the overtube (e.g., to an inner coil wound tube over the overtube) at bonding region 4853. As shown in FIGS. 48C-D, the handle includes a status indicator to indicate whether the overtube is in the flexible or rigid configuration. In this embodiment, the status indicator is such that the word "on" shows when the button is placed in the "on" position, and the word "off" shows when the button is placed in the "off" position. In other embodiments, the status indicator can be a symbol, color, light, or moving indicator.

The activation element can be a button, switch, toggle, slider, screwed connection, squeeze handle, or stop-cock. Further, the activation element can be planar, a sector, or omnidirectional. Further, the indicator element can include words, lights, or an element that spins with flow of vacuum.

In some embodiments, rather than including the activation element and indicator element on the handle, one or both can be on separate elements. For example, the activation element can be positioned along the vacuum line between the handle and the vacuum pump, can be actuated by a foot pedal, can be on the scope umbilical, or can be clipped on the patient's bed. Having the indicator element and/or activation element separate from the handle can advantageously allow the actuator and indicator to be seen more clearly (i.e., not be obstructed by the person's anatomy) and/or can allow the actuator and indicator to be controlled/used more easily by an additional person (e.g., a procedural assistant).

FIGS. 56A-D show a handle 5631 that is designed to allow manipulation of an overtube, but that does not include an activation element or an indicator element. The handle 5631 includes a large flange 5661 at the distal end thereof that can prevent the handle 5631 to act as an insertion blocker (i.e., to stop the handle from moving into the anatomy) and to act as a face against which the operator can push during use. The overtube can connect at bond region 5663. Further, the handle 5631 can include an input 5665 from the actuator connected to an output 5667 to the overtube.

Figure 50B:
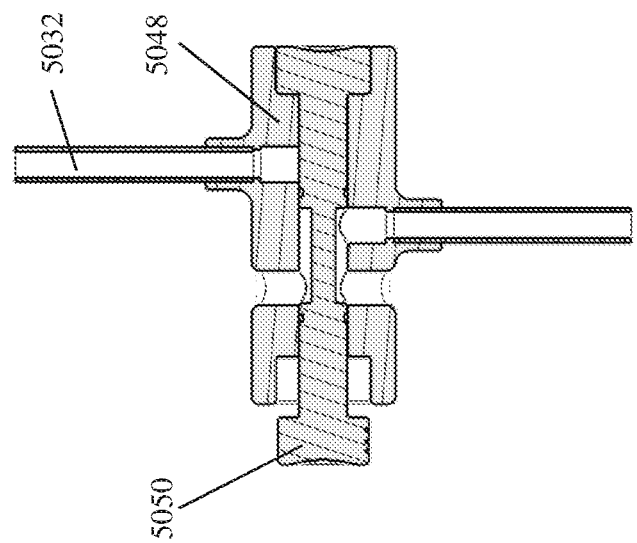
FIGS. 50A-50B show one embodiment of an activation element with an indicator thereon.
Figure 50A:
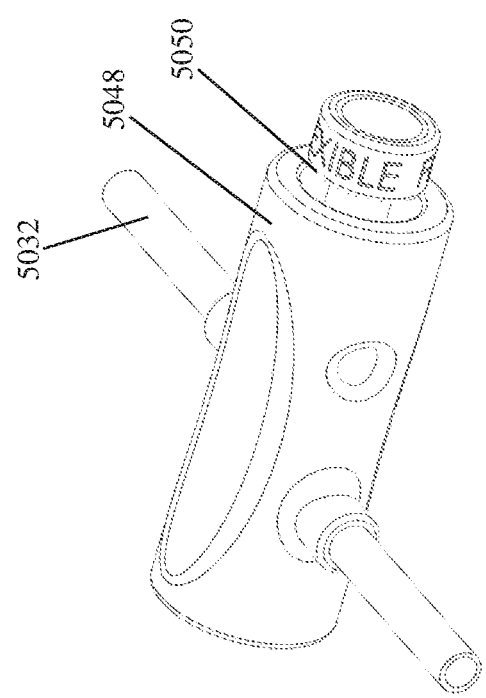

Referring to FIGS. 50A-50B, the activation element 5048 can be a spool valve that is shuttled in one direction to activate the vacuum in the overtube and can be shuttled in the opposite direction deactivate the vacuum. When preventing vacuum to the overtube, the activation element 5048 can provide venting. The actuator 5048 can be positioned on the vacuum line 5032 leading to the handle, such as 4'-8", e.g., 6" away from the handle. As shown in FIG. 50A, the spool valve with end button indicator element 5050 can indicate that the overtube is in the flexible configuration (as shown) or the rigid configuration (when pushed in the opposite direction).

Figure 51B:
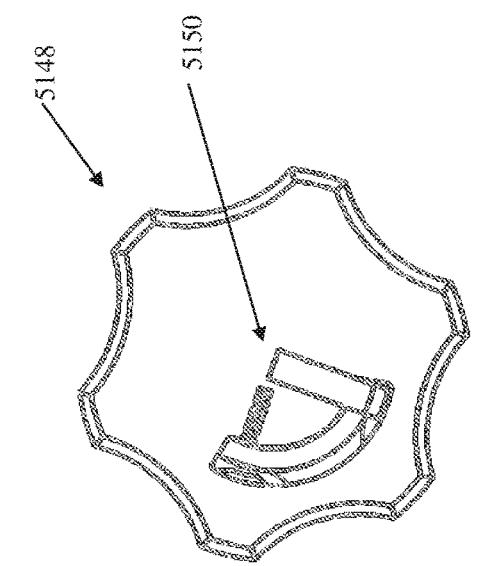
FIGS. 51A-51C show another embodiment of an activation element with an indicator thereon.
Figure 51A:
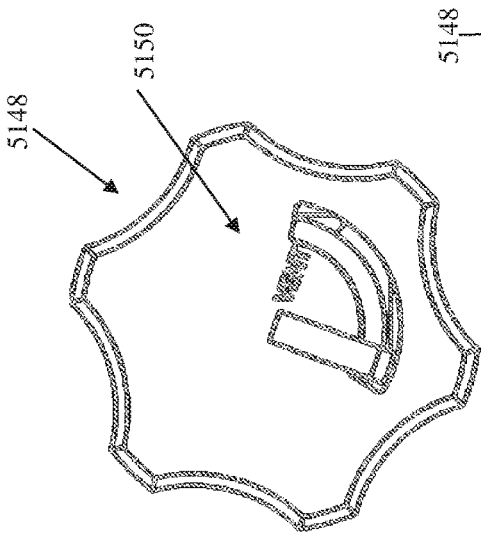
Figure 51C:
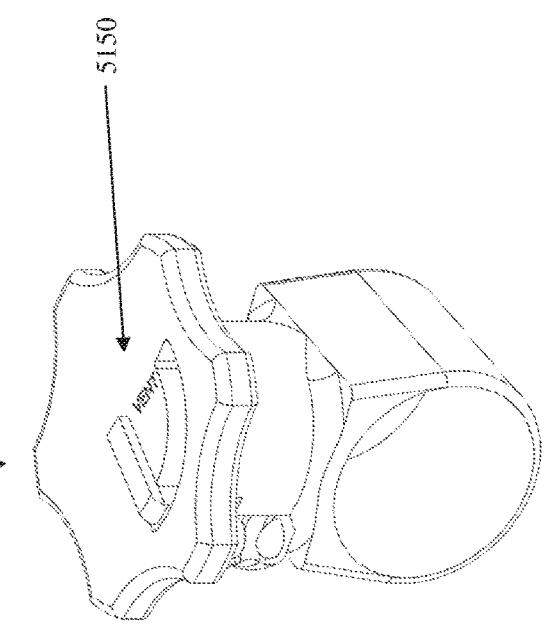

Referring to FIGS. 51A-51C, in some embodiments, the activation element 5148 can be a rotary valve (e.g., connected to the handle or elsewhere as described herein). Further, a sliding indicator 5150 can show that the vacuum is on (as shown in FIGS. 51A and 51C) or off (as shown in FIG. 51B).

Figure 52A:
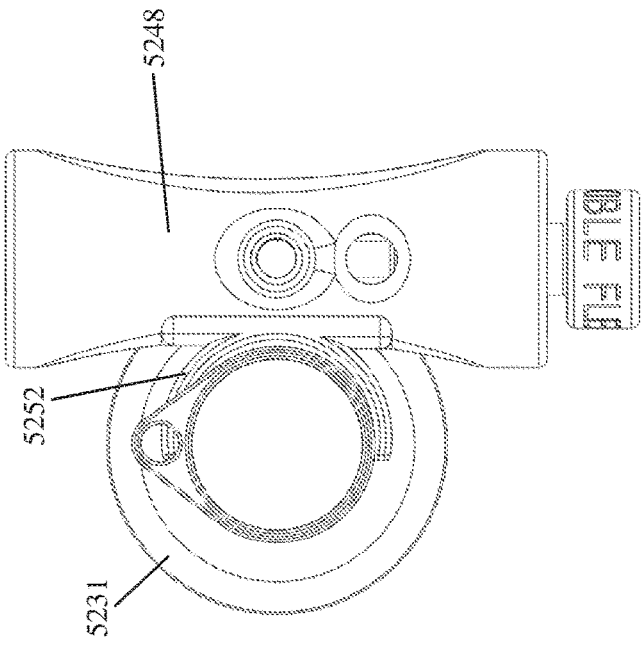
FIGS. 52A-52C show another embodiment of an activation element with an indicator thereon and the connection thereof to a handle.
Figure 52B:
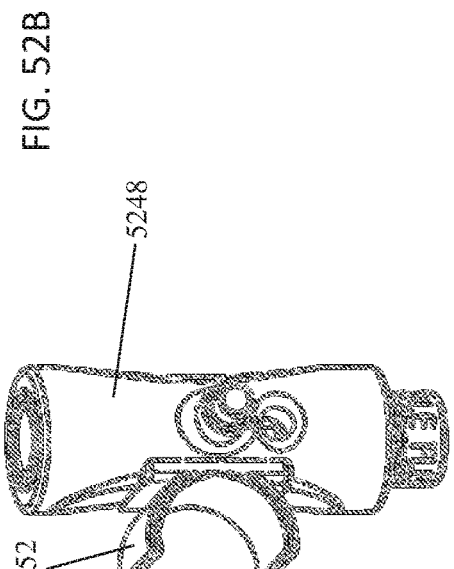
Figure 52C:
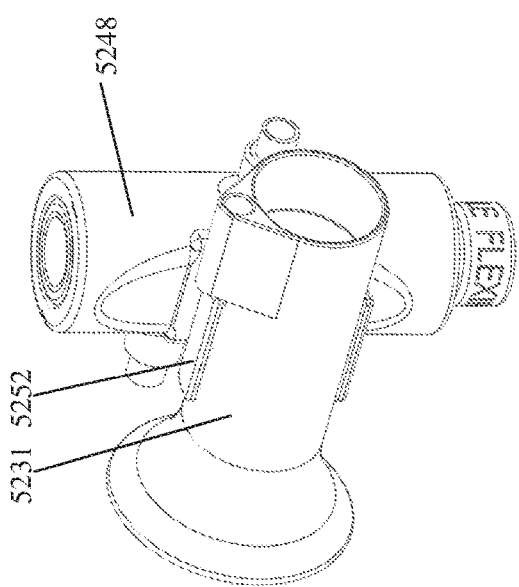

Another spool valve actuation element 5248 is shown in FIGS. 52A-52C. The element 5248 can be similar to element 5048 except that it can include an attachment mechanism 5252 (e.g., a c-shaped clip) for detachable coupling to a handle 5231.

Figure 53B:
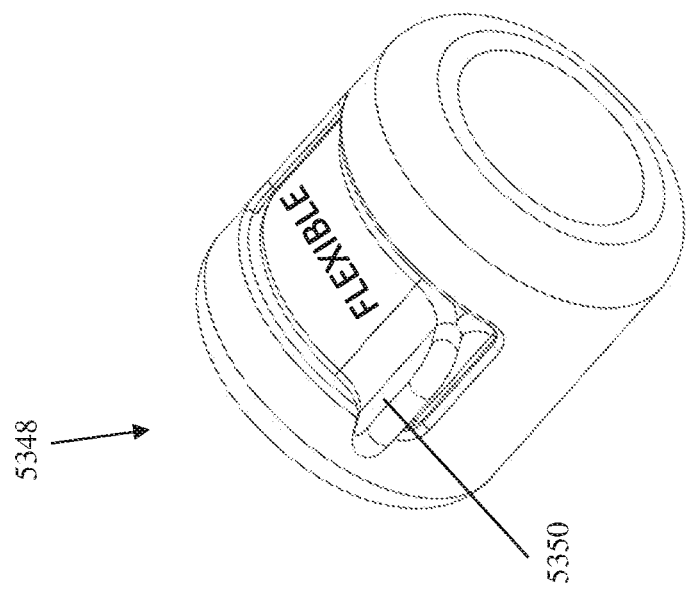
FIGS. 53A-53B show another embodiment of an activation element with an indicator thereon.
Figure 53A:
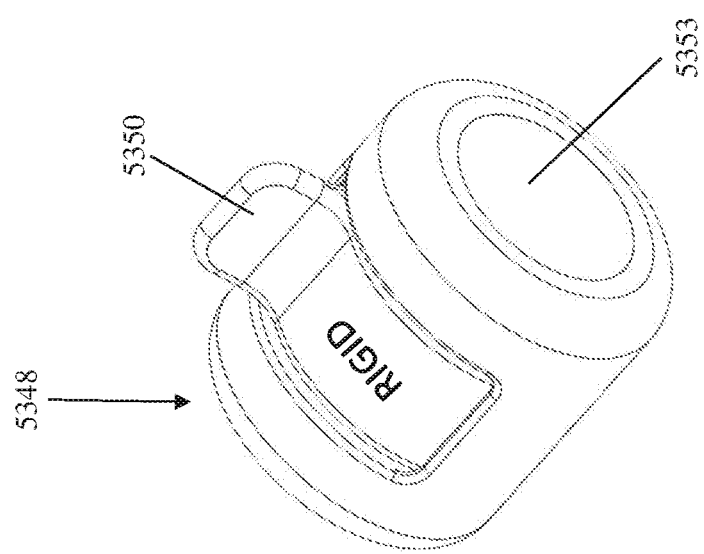
Figure 54A:
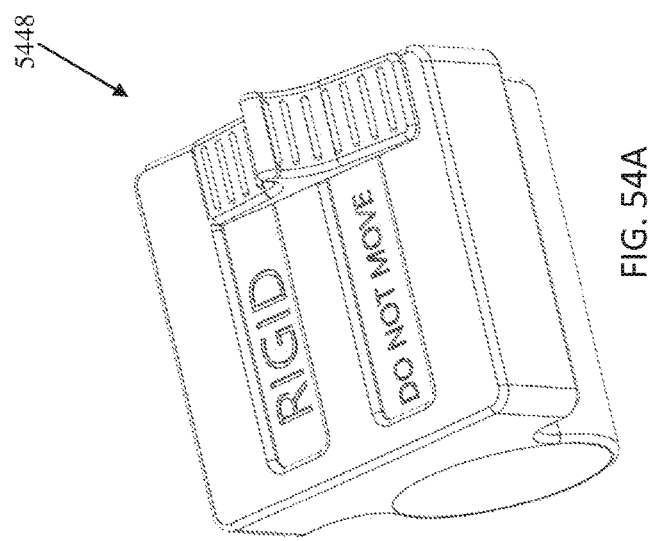
FIGS. 54A-54C show another embodiment of an activation element with an indicator thereon.
Figure 54B:
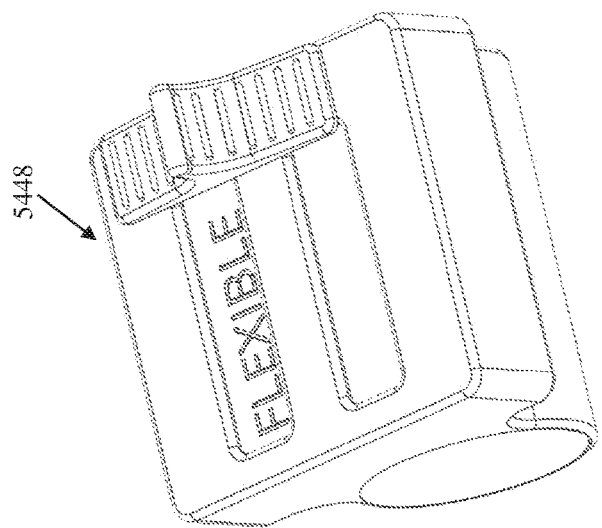
Figure 54C:
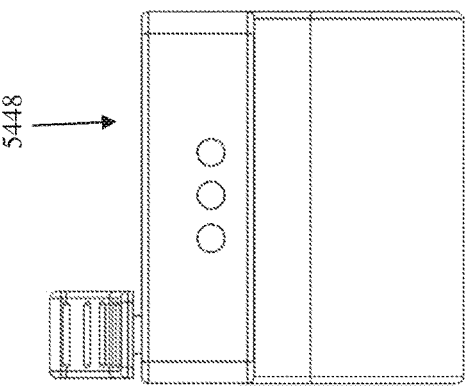
Figures 55A, 55B:
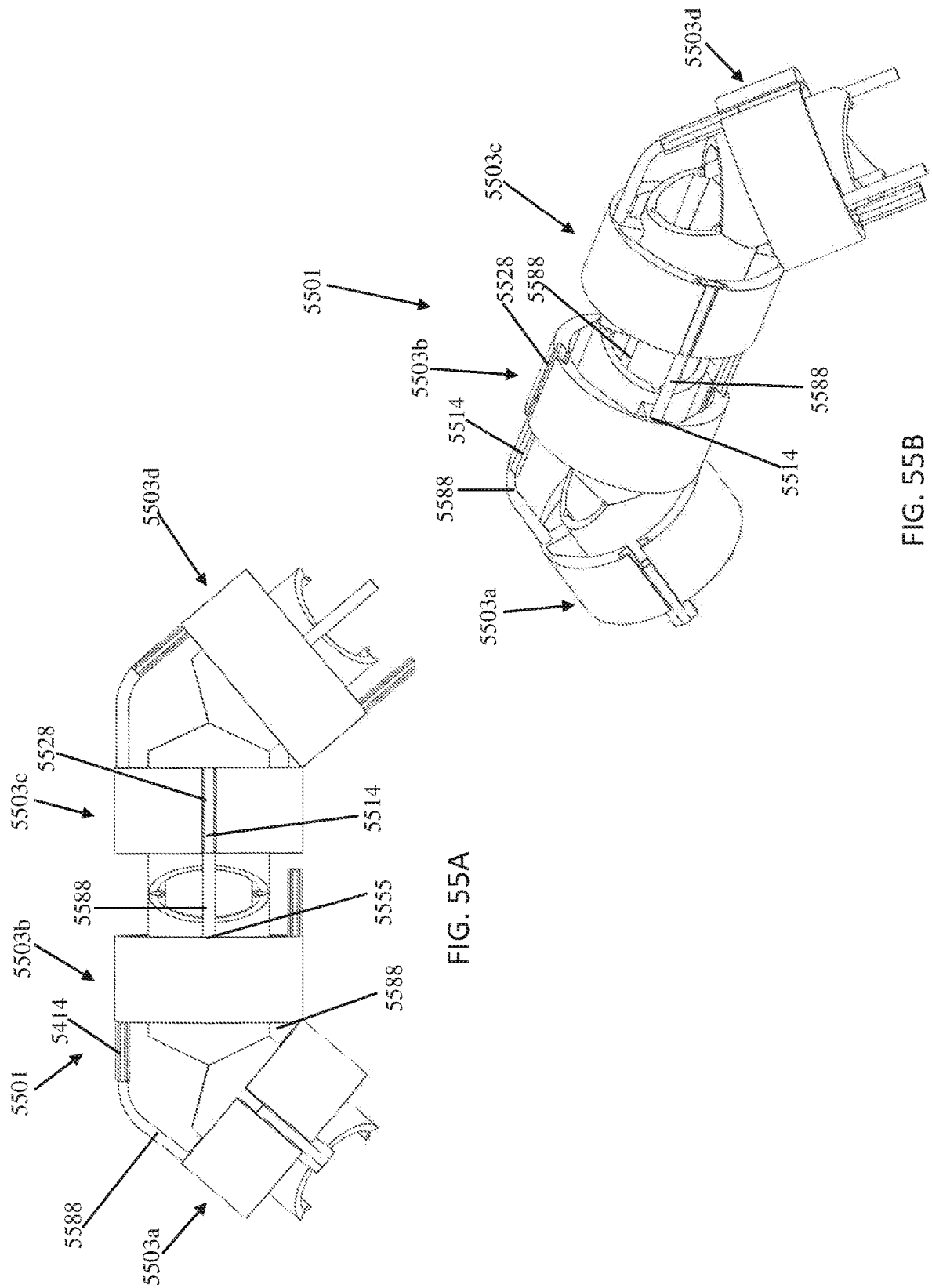
Figure 55E:
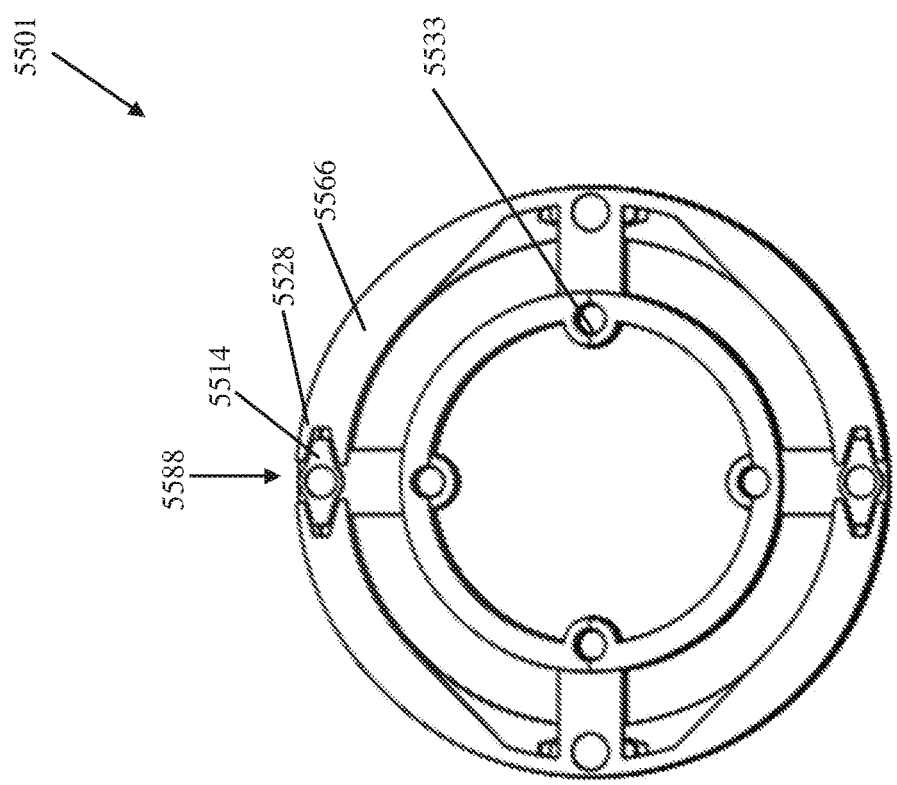
Figure 56B:
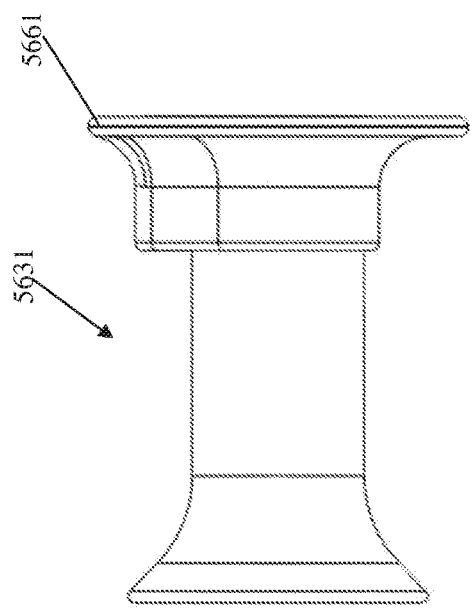
FIGS. 56A-56D show an exemplary handle for use with an overtube.
Figure 56D:
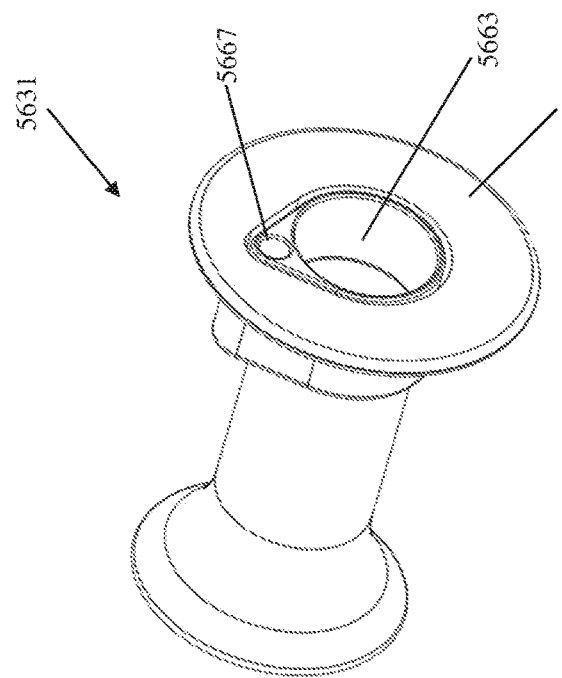
Figure 56A:
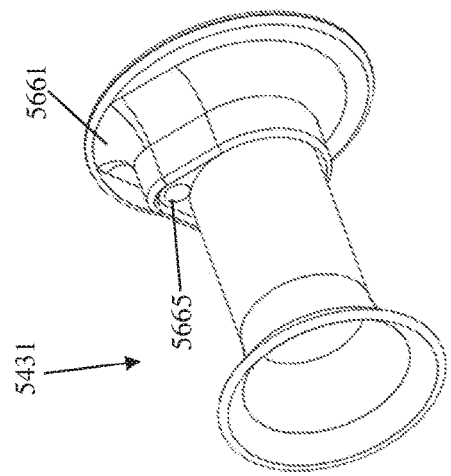
Figure 56C:
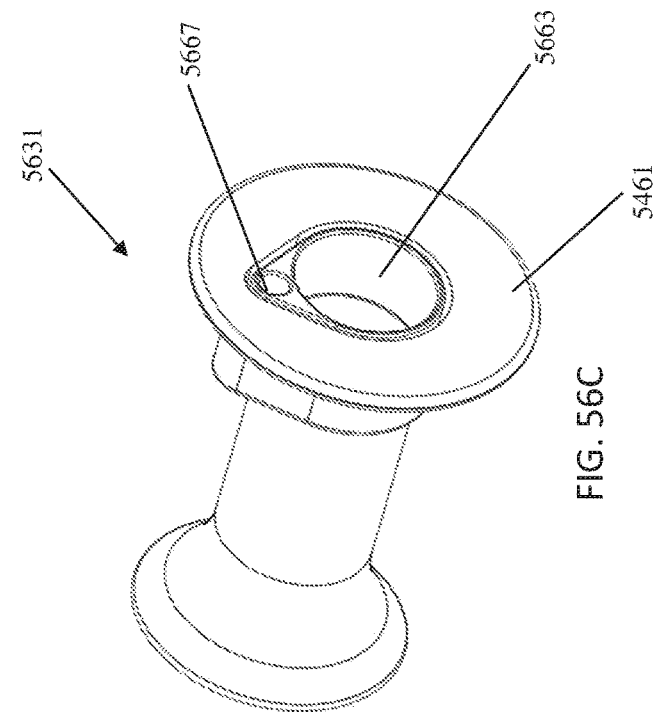

Referring to FIGS. 53A-53B, in some embodiments, the actuation element 5348 can be a slider element. The actuation element 5348 can include a connection element 5353 (e.g., a hollow tube or snap-fit element) configured to slide over a handle. The indicator element 5350 can be built into the slider (e.g., indicate "rigid" when the slider is in one position and "flexible" when the slider is in another position). A similar slider actuation element 5448 (this one orthogonal) can be seen in FIGS. 54A-54C.

In some embodiments, the vacuum can be applied through a manual pump and valve system rather than through an automated vacuum pump or wall vacuum source. The manual pump can be part of the overtube. In some embodiments, the handle can include a vacuum indicator.

In some embodiments, a handle for the overtube can be bonded to the midsection of the proximal most link. Strain relief heat shrink or an elastomer can be placed over the joint.

Figure 19:
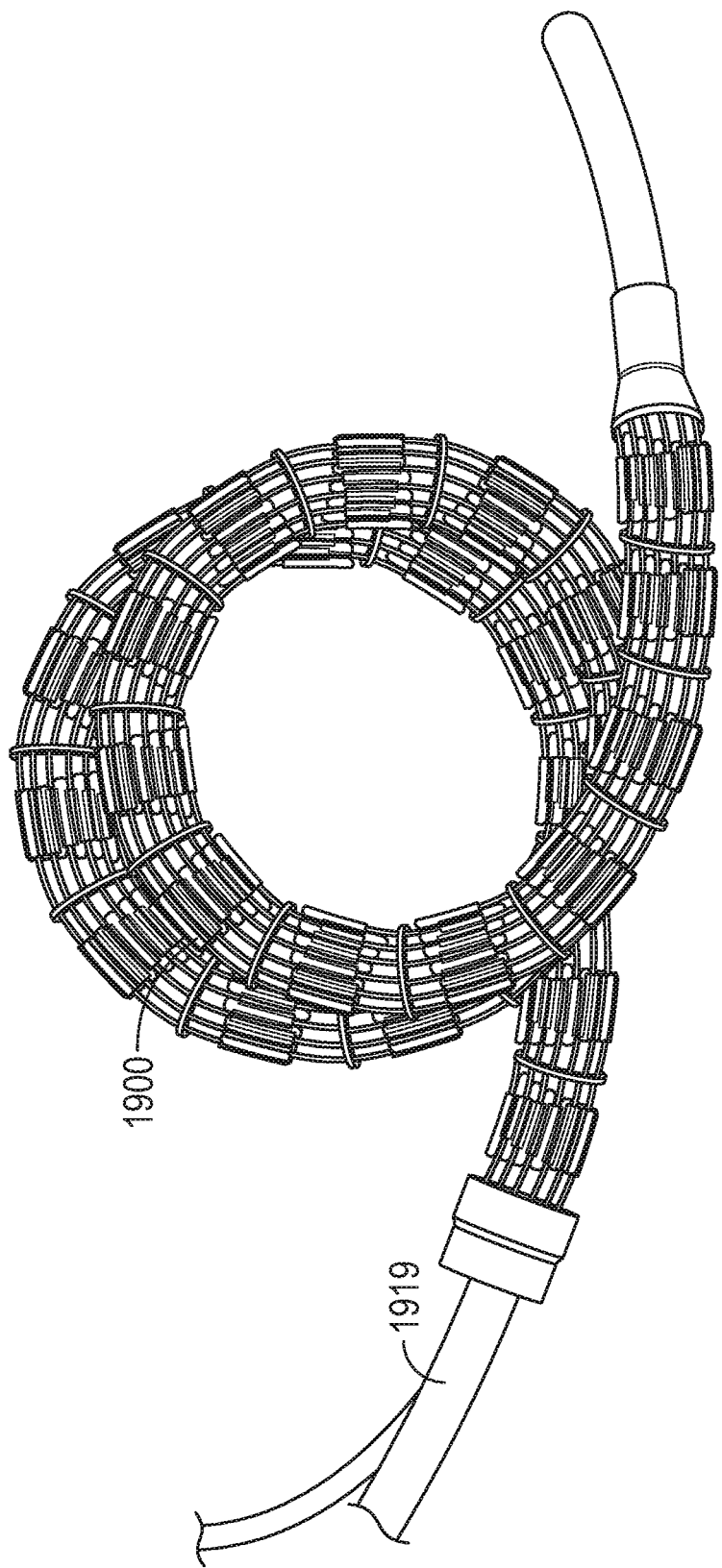
FIG. 19 shows coiling of an exemplary rigidizing overtube.

The overtubes described herein can advantageously be used to help navigate an endoscope through looping anatomy. FIG. 19 shows an endoscope 1919 extending through an overtube 1900 (without an outer sheath for clarity) that is in a rigid configuration (here, shown as a looped configuration). Because the overtube 1900 is rigid, the endoscope 1919 can easily move or slide therethrough. Thus, the rigid overtube 1900 can be used to counteract the reactive forces that would otherwise occur on the scope as the scope moves through the anatomy.

The overtubes/rigidizing devices described herein can toggle between the rigid and flexible configurations quickly, and in some embodiments with an indefinite number of transition cycles. As interventional medical devices are made longer and inserted deeper into the human body, and as they are expected to do more exacting therapeutic procedures, there is an increased need for precision and control. Selectively rigidizing members or overtubes as described herein can advantageously provide both the benefits of flexibility (when needed) and the benefits of stiffness (when needed).

In one method of use, during a surgical procedure, an overtube as described herein can be introduced to the patient in the flexible configuration over the endoscope, then steered towards the desired anatomy. Once the distal end of the overtube is positioned past the challenging anatomy (i.e., that portion that tends to cause looping), the overtube can be transitioned to the rigid configuration. The scope or other instrument can then be advanced through the challenging or looped anatomy.

Figure 20:
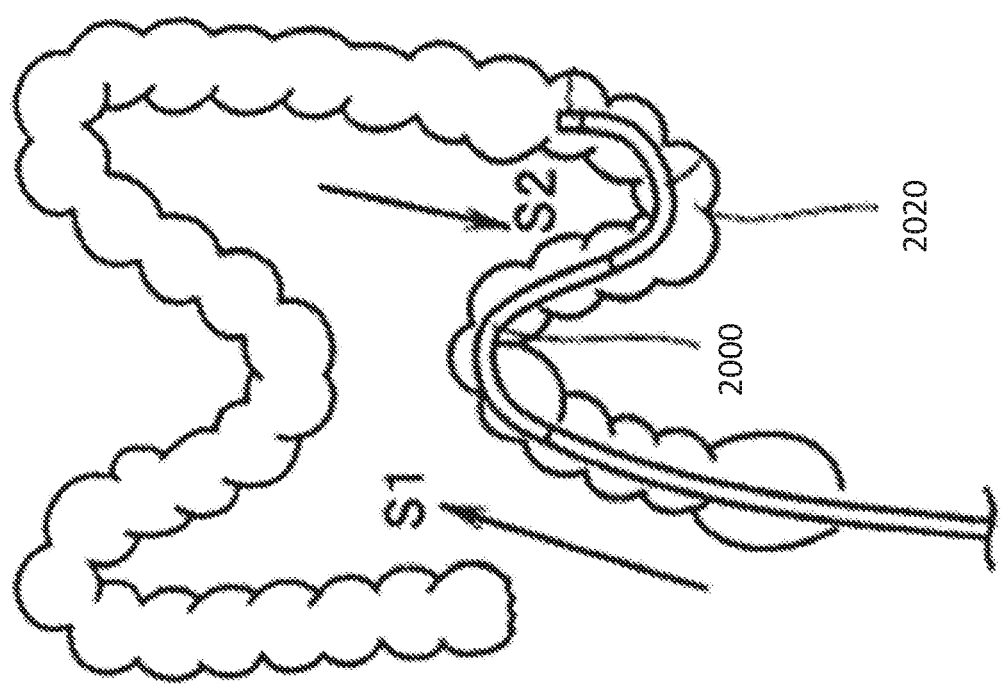
FIG. 20 shows use of an endoscope in the colon.
Figure 21C:
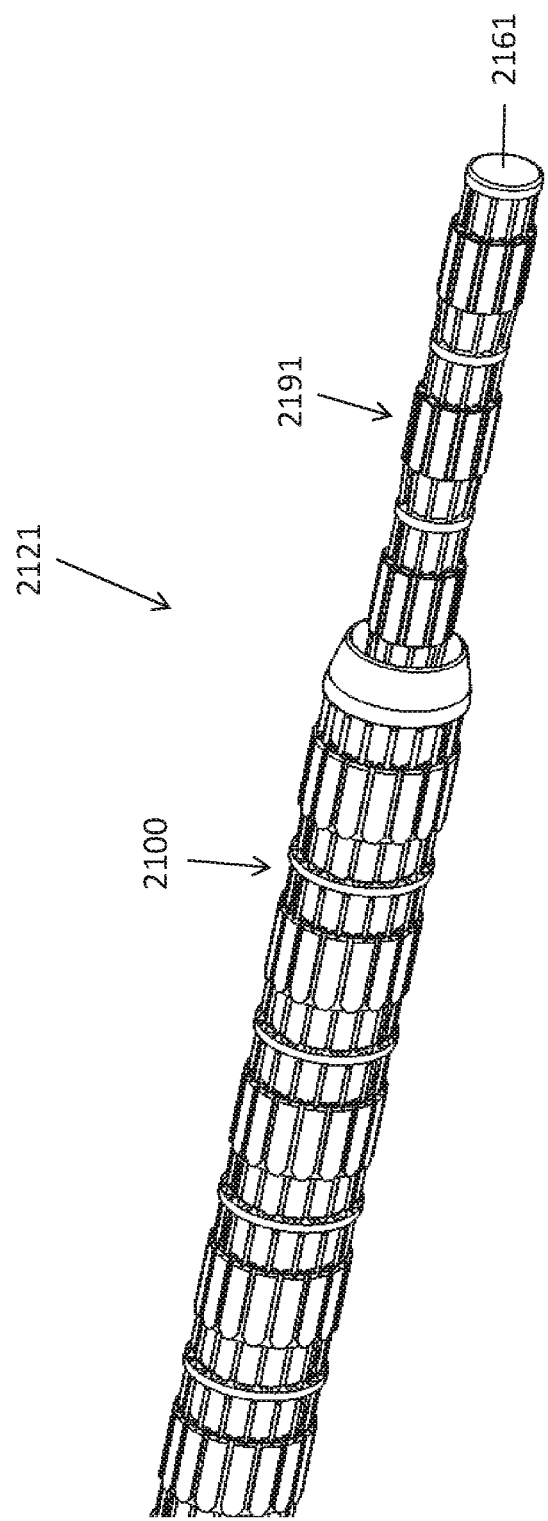
Figure 21D:
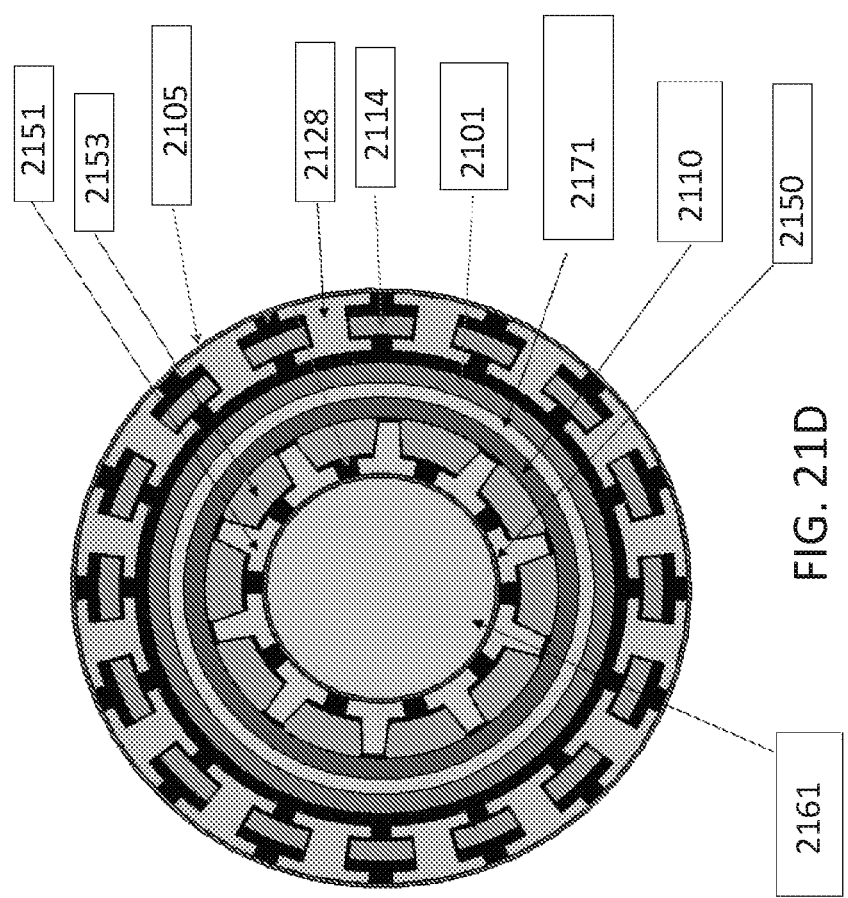

Referring to FIG. 20, for example, the overtube 2000 can be used to extend through the sigmoid colon 2020. In use, for example, the overtube 2000 can be extended past the curves S1 and S2 in the flexible configuration. Vacuum can then be pulled to transition the overtube 2000 to the rigid configuration, allowing the endoscope to be passed therethrough. This could be performed with or without a sigmoid reduction. The overtubes described herein can also be used, for example, elsewhere in the gastrointestinal tract, in the vascular system (including over the aortic arch), or into the peritoneal cavity.

Although described as being used as part of an overtube, the dynamically rigidizing mechanisms described herein can be used with other medical technologies as well. For example, the dynamically rigidizing mechanisms can be incorporated directly into the shaft of an endoscope and/or can be used as part of a catheter, probe, or surgical guide.

In some embodiments, the overtubes/rigidizing devices described herein can be used to stiffen a guide sheath in interventional cardiology or structural heart cases. For example, the overtubes/rigidizing devices can be used to provide a "rail" for the transcatheter aortic valve replacement (TAVR) device, thereby keeping the tip of the TAVR catheter from scraping and skiving the top of the aortic arch where there is often thrombus burden (current systems tend to ride the outside of the arch, rubbing against plaques, creating embolic storms). The overtubes/rigidizing devices can help enable superior alignment and placement as well as lower paravalvular leakage and optimal placement relative to pacing nodes.

In some embodiments, the overtubes/rigidizing devices described herein can be used to deliver a mitral valve replacement. That is, crossing the septal wall during mitral valve replacement can be particularly difficult, as it involves multiple curves, a beating heart, and the need for precisely aligned entry and stabilization before delivery of the implant. Current valve delivery platforms can be quite rigid, which can be dangerous for anatomy that it straightens (such as the femoral artery, which can be highly calcified and friable). The overtubes/rigidizing devices described herein can advantageously create a conduit that goes in flexibly, then rigidizes in whatever shape the particular person's anatomy provided, such that the overtube/rigidizing device conforms to the entire anatomical track. As a result, the overtubes/rigidizing devices described herein can allow the clinician to create a stable mechanical lumen leading directly to the anatomy, to locate it without significant local anatomical load, then to stabilize rigidly in that shape as a device is delivered through it.

In some embodiments, the rigidizing devices can be incorporated into catheters for interventional cardiology, such that they track very easily (flexible), then can be rigidized for instances when the device is used to push through locally anatomy, including CTOs (Chronic Total Occlusions).

In some embodiments, the overtubes/rigidizing devices described herein can be used to stiffen an overtube for gastroenterology, such as to stiffen an endoscope.

As another example, the overtubes/rigidizing devices described herein can be integrated into an endoscope such that the endoscope can be selectively rigidized.

In some embodiments, the overtubes/rigidizing devices described herein can be utilized to perform therapies during esophagogastroduodenoscopy (EGD), for example, on the roof of the stomach.

In some embodiments, the overtubes/rigidizing devices described herein can be used to create more optimal access and stabilization during ERCP (Endoscopic Retrograde Cholangiopancreatograpy), including the kinematically and clinically challenging tasks of cannulating the ampulla.

In some embodiments, the overtubes/rigidizing devices described herein can be used to create an overtube for enteroscopy. Enteroscopy is kinematically challenging for several reasons, including because the scopes are relatively small diameter (9 mm), they are very long (2 meters), and they frequently loop as they navigate the gastrointestinal tract to get to the small intestine starting line (either the pylorus or the terminal ileum).

In some embodiments, the overtubes/rigidizing devices described herein can be used in conjunction with other versions of the product. For example, an endoscope can include the rigidizing mechanisms described herein, and an overtube can include the rigidizing mechanisms described herein. Used together, they can create a mother-daughter system that can advance, one after the other, allowing one of the elements to always remain stiffened, such that looping is reduced or eliminated.

In some embodiments, the overtube can have an inner diameter of 0.52" and an outer diameter of 0.71", thereby providing room for a scope to extend therethrough while also allowing the scope to extend through the desired body lumen. In other embodiments, for example in catheter-based systems, the inner diameter can be as low as 0.10"-0.12".

In some embodiments, the overtubes described herein can be in a mother-daughter configuration. Referring to FIGS. 21A-21D, for example, a system 2121 can include an overtube 2100 and a scope 2191 that are axially movable relative to one another, either concentrically or non-concentrically. Further configurations could be constructed, including rigidizing elements, steerable elements, an endoscope, and lumen(s) for instruments. The overtube 2121 can be configured as described elsewhere herein (e.g., with links, engagers, etc.). Further, the scope 2191 can include an outer shaft that includes the rigidizing elements as described herein. Each of the overtube 2121 and the scope 2191 can include an outer layer 2105 and a cover 2110 (such as a coil wound tube), respectively (the outer layer 2105 and cover 2110 have been removed in FIG. 21C for clarity).

The overtube 2100 can include, for example, rigidizing features as described elsewhere, such as male and female engagers 2114, 2128 that can engage and lock when vacuum is pulled on the system. The male and female engagers 2114, 2128 can be positioned around a coiled flexible inner tube 2101. A gap 2171 can be present between the overtube 2121 and the scope 2191 to allow for sliding. Further, the shaft of the scope 2191 can include rigidizing elements, such as inner wedges 2152 and outer wedges 2153 configured to engage and lock when a vacuum is pulled. An inner sheath 2150 can separate and seal the wedges 2152 and 2153 from the inner working 2161 for scope features.

The system 2121 can be used to facilitate movement through a tightly curved body lumen. In use, the scope 2191 can be inserted into the curved area and bent or steered into the desired shape. Vacuum can be applied to the scope 2191 to causes the wedges 2152, 2153 to engage and lock the scope 2191 in the configuration. The overtube 2100 can then be advanced over the rigid scope 2191. When the overtube 2100 reaches the tip of the scope 2191, vacuum can be applied to the overtube 2100 to cause the male and female engagers 2114, 2128 to engage and lock to fix the shape of the overtube. The scope 2191 can be advanced and the process repeated.

Although the system 2121 is described as including an overtube and a scope, it should be understood that other configurations are possible. For example, the system might include two overtubes, two catheters, or a combination of overtube, catheter, and scope.

Referring to FIGS. 41A-41D, in some embodiments, the overtubes described herein can include a built-in working channel to allow the user to perform procedures with additional features, including the use of more tools, traction, enhanced insufflation, suction, or wash. The working channel can be positioned within the vacuum layer or outside of the vacuum layer.

For example, as shown in FIG. 41A, an overtube 4100a can include a plurality of small rings 4124a attached to the link mounting rings 4122a. A tube 4142a can extend the length of the overtube 4200a and can be held by the rings 4124a. In some embodiments, the tube 4142a can be a telescoping tube to provide more flexibility as the overtube 4100a bends. The tube 4142a can thus function as a working channel for the overtube 4100a.

As shown in FIG. 41B, an overtube 4100b can include a bendable layer 4171b (e.g., with linkages as described herein), a tube 4142b attached thereto, and a thin sheet 4172b (e.g., an elastomeric sheath) thereover. The tube 4142b can be, for example, a spiral-slit tube to allow the tube 4142b to bend to a certain radius without substantially stressing the bendable layer 4171b. The thin sheet 4172b can provide vacuum sealing for the overtube 4100b. In some embodiments, bellows can be used for the working channel.

Figure 41C:
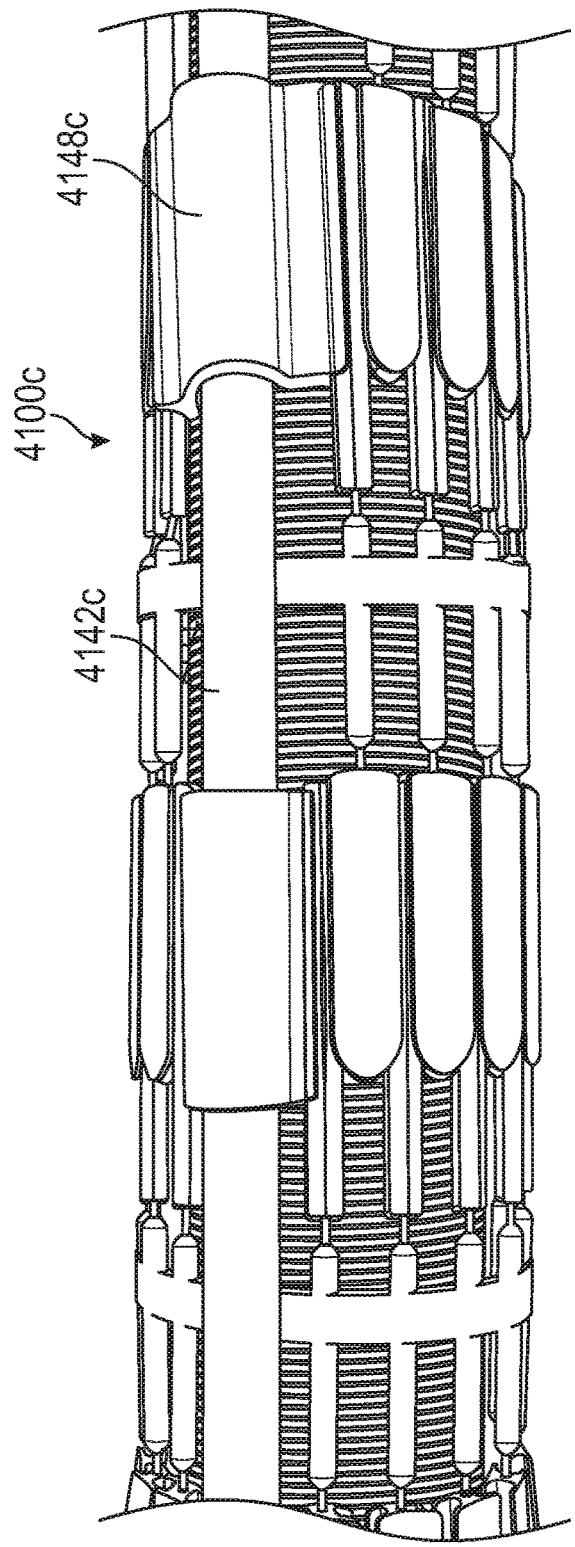

As shown in FIGS. 41C, an overtube 4100c can include a tube 4142c that extends between engagers (e.g., in place of one or more engagers at each linkage). The tube 4142c can be held down, for example, with u-shaped connector 4148c at each linkage.

Figure 41D:
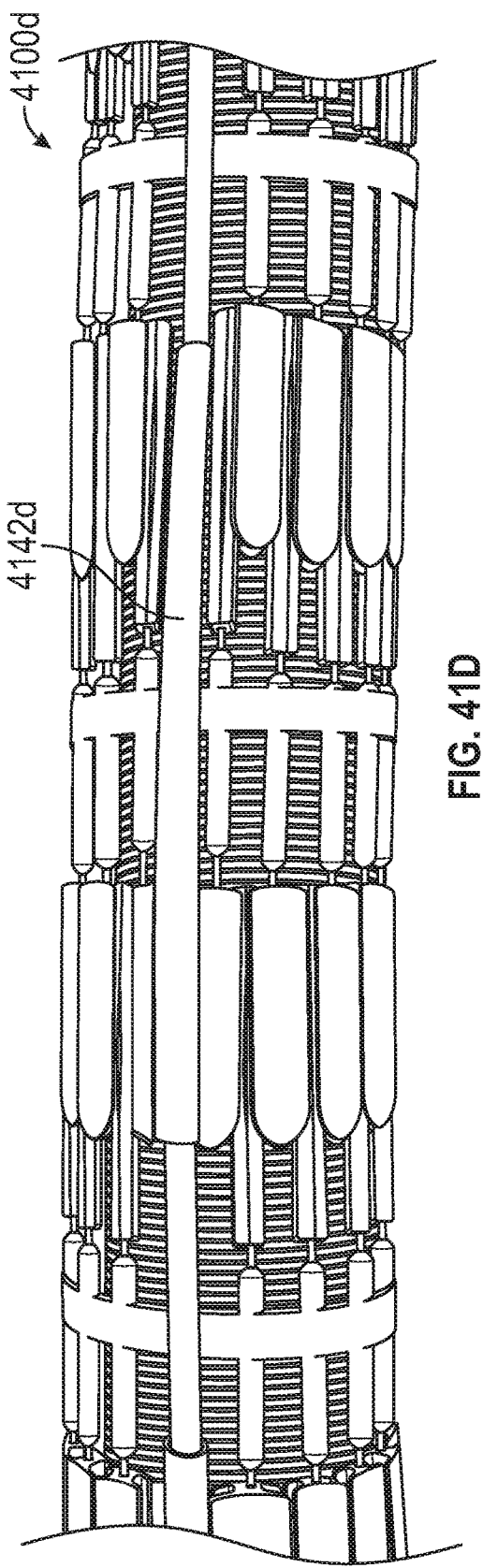

As shown in FIG. 41D, an overtube 4100d can include a tube 4142d that similarly extends between engagers (e.g., in place of one or more engagers at each linkage). The tube 4142d can, for example, be a telescoping tube with smaller diameter portions sliding within the larger diameter portions.

Figure 47:
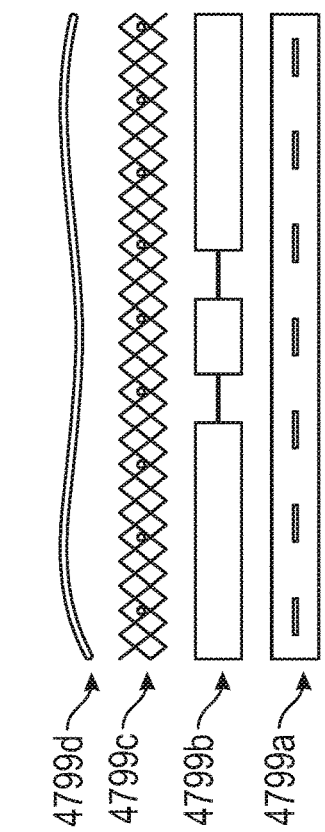
Figure 46:
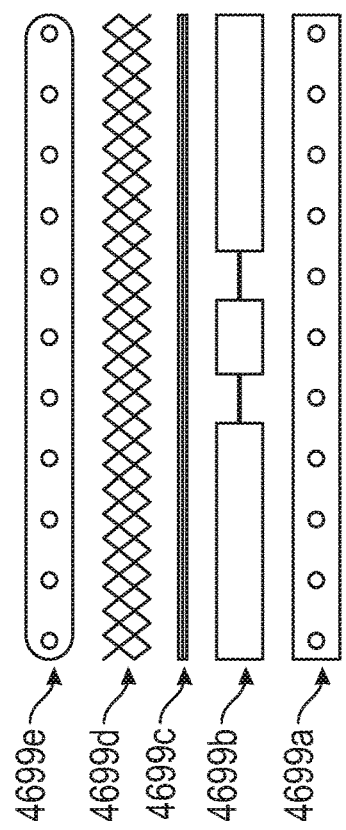

In some embodiments, the various layers and/or features of the overtubes described herein can be combined, substituted, and/or rearranged relative to other layers. FIGS. 43-47 show various layered embodiments. For example, FIG. 43 shows the wall of an overtube that includes layers 4399a-f. Inner layer 4399a can be a coil-wound tube or extrusion, layer 4399b can be a slip layer, layer 4399c can be a braid, layer 4399d can be fiber-wound hoops (either woven in or on top of the braid of layer 4399c), layer 4399e can be the linkages, and outer layer 4399f can be an outer sheath (e.g., made of urethane). As another example, FIG. 44 shows the wall of an overtube that that includes layers 4499a-d. The inner layer 4499a can be a coil wound tube, layer 4499b can be the linkages, layer 4499c can be a braid, and outer layer 4499d can be fiber-wound hoops. As another example, FIG. 45 shows the wall of an overtube that includes layer 4599a-c. Inner layer 4599a can be a coil-wound tube, layer 4599b can be the linkages, and outer layer 4599c can be an outer sheath. As another example, FIG. 46 shows the wall of an overtube that includes layers 4699a-e. Inner layer 4699a can be a coil wound tube, layer 4699b can be the linkages, layer 4699c can be a thin sheath, layer 4699d can be a braid, and outer layer 4699e can be fiber-wound hoops (e.g., embedded in polymer). As another example, FIG. 47 shows the wall of an overtube that includes layers 4799a-4799d. Inner layer 4799a can be a coil wound tube, layer 4799b can be the linkages, layer 4799c can be a braid, and outer layer 4799d can be a sheath. In yet another version, layer 4399a can be followed by slip layer 4399b, one, two, three or four layers 4399c of braid, and an outer layer formed by layer 4399f.

In some embodiments, the male and female engagers can be configured to unlock when vacuum is released. This unlocking can be achieved passively by the proper combination of material and design (e.g., angle of wedges). Alternatively or additionally, the unlocking can be achieved actively by forcing engagers apart when vacuum is removed. For example, a spring-like feature, such as an elastomer, can be placed below the engagers (e.g., radially inward of the engagers) to push the engagers out and away from one another when vacuum is removed.

In some embodiments, rather than fixing the engagers to the mounting ring (e.g., via a pivot), the engagers can be configured to be "floating" or adjustably attached to the mounting ring (e.g., via a spring). Floating engagers can advantageously allow for both strong engagement and the strong release requisite for proper free-sliding between engagers.

In some embodiments, rather then using mounting rings, the engagers can be bonded directly into the underlying tube.

In some embodiments, the friction of the engagers can be increased by using a fiber filled elastomer (e.g., glass or carbon), polystyrene, SBC, metallization (Ti, Al, Copper, SS), physical vapor deposition (PVD) (Au, Ag), adding powder or dust or abrasives. In some embodiments, the COF numbers can range from 0.4 to 2.0.

In some embodiments, the mounting rings can have a modulus of greater than 0.5 msi with inserted molded cable pivots. The cable pivot gaps can be short so that the wire can bend in a cone of motion but not buckle or deform. The engagers can have a modulus of 0.2 msi-0.5 msi, such as 0.4 msi. The female engagers can be I-beams and therefore have high stiffness. The male engagers can be of sufficient stiffness to flex to allow for properly alignment, but stiff enough so as not to buckle. The engagers can be configured so as to not slip under vacuum.

In some embodiments, the tip of the overtube can include a balloon, cage, or suction at the tip for local tissue stabilization.

In some embodiments, the overtube can have a customizable length where by the appropriate number of segments are chosen and assembled.

Figure 49A:
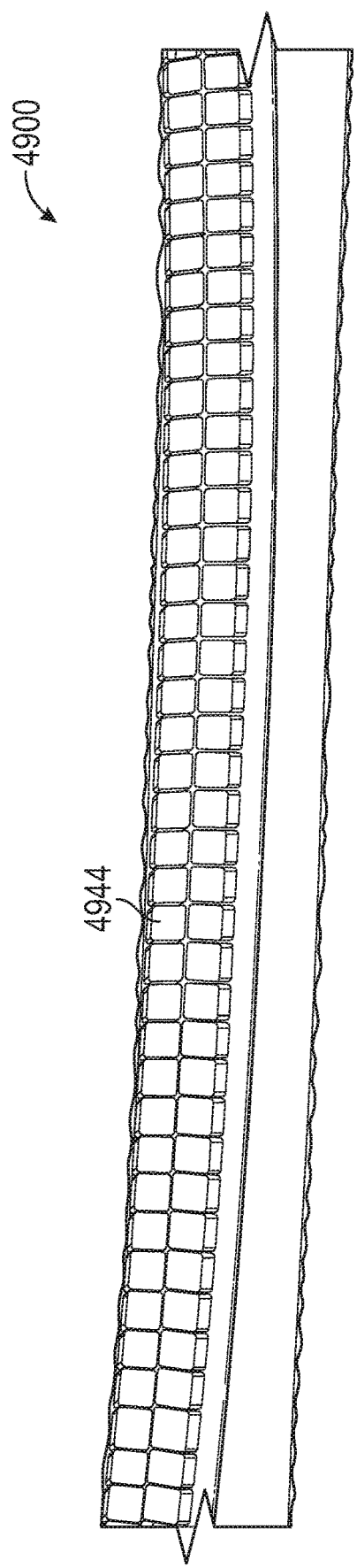
FIGS. 49A-49B show an overtube with a slit therein for side loading over an instrument.
Figure 49B:
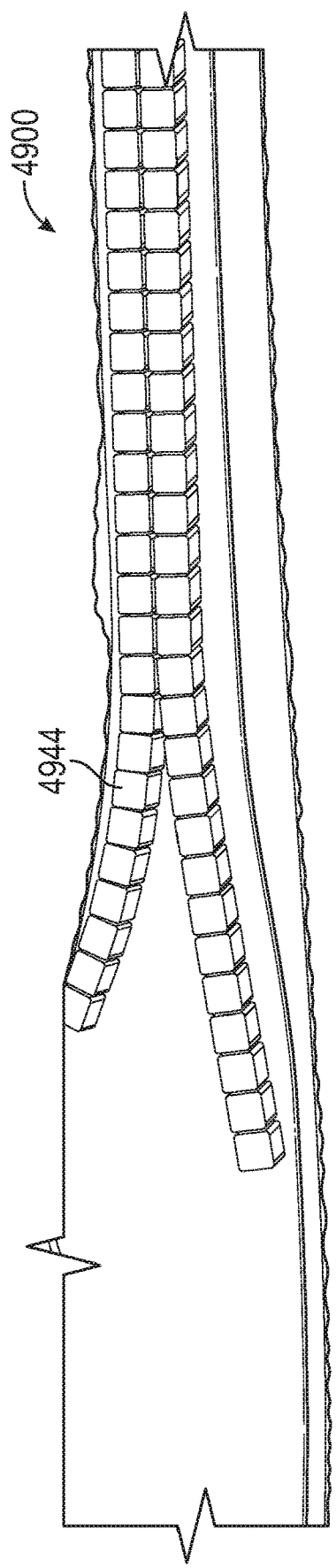

In some embodiments, the overtubes described herein can be configured to be loaded over the side of the scope or other instrument (e.g., rather than requiring insertion of the scope/instrument into the proximal end of the overtube). For example, as shown in FIGS. 49A-49B, the overtube 4900 can be split along the length thereof (i.e., split longitudinally through the wall from the proximal end to the distal end). Further, a connection feature 4944 can connect the split wall together. In some embodiments, the connection feature 4944 can be reusable. For example, the connection feature 4944 can be a series of magnets that can engage (FIG. 49A) to hold the overtube 4900 together and disengage (FIG. 49B) to provide side access for the scope/instrument. Other exemplary reusable connection features include zippers, interlocking zip-lock male and female configuration, or reusable tape. In some embodiments, the connection feature 444 can be permanent and not reusable, such as permanent tape or adhesive.

In some embodiments, to augment the pressure against the engagers and to reduce the propensity to locally buckle, an additional layer can be placed over the outer layer. The additional layer can have a higher modulus material or can be fiber-reinforced relative to the outer layer. In between the outer layer and this additional layer, high pressure can be introduced, which can create an enhanced pressure of the outer layer against the engagers to keep high friction and to help prevent the overtube it from buckling.

The overtubes or rigidizing devices and systems described herein can be used, for example, with classic endoscopes, colonoscopes, robotic systems, and/or navigation systems, such as those described in International Patent Application No. PCT/US2016/050290, filed Sep. 2, 2016, titled "DEVICE FOR ENDOSCOPIC ADVANCEMENT THROUGH THE SMALL INTESTINE," the entirety of which is incorporated by referenced herein.

It should be understood that any feature described herein with respect to one embodiment can be combined with or substituted for any feature described herein with respect to another embodiment.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. A rigidizing overtube comprising:
an elongate flexible tube;
mounting elements attached to the elongate flexible tube;
a plurality of male engagers and a plurality of female engagers connected to the mounting elements, the plurality of male and the plurality of female engagers positioned in an alternating arrangement around a circumference of the rigidizing overtube;

wherein the rigidizing overtube has a flexible configuration in which the plurality of male and female engagers are configured to move axially relative to each other to accommodate bending of the elongate flexible tube;

wherein the rigidizing overtube has a rigid configuration in which the plurality of female engagers are fixed relative to the plurality of male engagers to prevent the elongate flexible tube from bending, wherein the mounting elements is attached to the elongate flexible tube so that axial movement between the mounting elements and the elongate flexible tube is prevented when the rigidizing overtube is in the flexible configuration and the rigid configuration, and wherein the rigidizing overtube is configured such that an application of vacuum between an outer layer and an inner tube of the rigidizing overtube transitions the rigidizing overtube from the flexible configuration to the rigid configuration and fixes the plurality of female engagers relative to the plurality of male engagers by constricting the outer layer around the plurality of female engagers and the plurality of male engagers, further wherein removal of the application of vacuum returns the rigidizing overtube to the flexible configuration.

2. The rigidizing overtube of claim 1, wherein the outer layer is positioned around the plurality of male engagers and the plurality of female engagers.

3. The rigidizing overtube of claim 1, wherein the plurality of male engagers and the plurality of female engagers are connected to the mounting elements with a plurality of pivoting elements, each of the plurality of pivoting elements connected to a male engager of the plurality of male engagers or a female engager of the plurality of female engagers.

4. The rigidizing overtube of claim 1, wherein the plurality of male engagers and the plurality of female engagers are positioned in an alternating arrangement along a longitudinal axis of the rigidizing overtube.

5. The rigidizing overtube of claim 4, wherein the plurality of male engagers have a double-wedge shaped cross section.

6. The rigidizing overtube of claim 1, wherein the plurality of female engagers have an I-shaped cross section.

7. The rigidizing overtube of claim 1, further comprising a plurality of motion stops configured to prevent the plurality of female engagers and the plurality of male engagers from disengaging with one another when pulled apart axially, wherein the plurality of motion stops include serrations on the plurality of female engagers configured to interface with serrations on the plurality of male engagers, and vice versa.

8. A rigidizing overtube comprising:
an elongate flexible tube;
mounting elements attached to the elongate flexible tube;
a plurality of female engagers connected to the mounting elements; and
a plurality of male engagers connected to the mounting elements;
wherein the plurality of male engagers and the plurality of female engagers are positioned in an alternating arrangement around a circumference of the rigidizing overtube;
wherein the rigidizing overtube has a flexible configuration in which the plurality of male engagers are configured to move axially within and relative to the plurality of female engagers to accommodate bending of the elongate flexible tube;

wherein the rigidizing overtube has a rigid configuration in which the plurality of male engagers are fixed relative to the female engagers to prevent the elongate flexible tube from bending, wherein the mounting elements is attached to the elongate flexible tube so that axial movement between the mounting elements and the elongate flexible tube is prevented when the rigidizing overtube is in the flexible configuration and in the rigid configuration, and wherein the rigidizing overtube is configured to attach to a source of vacuum such that an application of vacuum between an outer layer and an inner tube of the rigidizing overtube transitions the rigidizing overtube from the flexible configuration to the rigid configuration, wherein the application of vacuum fixes the plurality of male engagers and the plurality of female engagers relative to other of the plurality of male engagers and the plurality of female engagers via constricting the outer layer around the plurality of male engagers and the plurality of female engagers, wherein removal of the application of vacuum returns the rigidizing overtube to the flexible configuration.

9. The rigidizing overtube of claim 8, wherein the outer layer is positioned around the plurality of male engagers and the plurality of female engagers.

10. The rigidizing overtube of claim 8, wherein the plurality of male engagers and the plurality of female engagers are connected to the mounting elements with a plurality of pivoting elements, each of the plurality of pivoting elements connected to one of the plurality of male engagers or the plurality of female engagers.

11. The rigidizing overtube of claim 8, wherein the plurality of male engagers and the plurality of female engagers are positioned in an alternating arrangement along a longitudinal axis of the rigidizing overtube.

12. The rigidizing overtube of claim 8, wherein the plurality of male engagers have a double-wedge shaped cross section.

13. The rigidizing overtube of claim 8, wherein the plurality of female engagers have an I-shaped cross section.

14. The rigidizing overtube of claim 8, further comprising a plurality of motion stops configured to prevent the plurality of female engagers and the plurality of male engagers from disengaging with one another when pulled apart axially, wherein the plurality of motion stops include serrations on the plurality of female engagers configured to interface with serrations on the plurality of male engagers, and vice versa.

15. The rigidizing overtube of claim 8, wherein the plurality of male engagers or the plurality of female engagers include serrations thereon.

16. The rigidizing overtube of claim 1, wherein the plurality of male engagers and the plurality of female engagers are configured to move relative to each other with respect to a longitudinal axis of the rigidizing overtube.

17. The rigidizing overtube of claim 1, wherein the plurality of male engagers include a plurality of extensions, and the plurality of female engagers include a plurality of inner and outer flanges that define slots that are configured to accommodate the plurality of extensions therein.

18. The rigidizing overtube of claim 1, wherein the mounting elements are shaped as rings.

19. The rigidizing overtube of claim 1, wherein each of the plurality of male engagers engages with two of the plurality of female engagers.

20. The rigidizing overtube of claim 1, wherein the application of vacuum causes the outer layer to radially constrict the plurality of male engagers and the plurality of female engagers, thereby causing the plurality of male engagers and the plurality of female engagers to fix in place in the rigidized configuration.

* * * * *